United States Patent
Kjaerulff et al.

(10) Patent No.: US 11,179,447 B2
(45) Date of Patent: Nov. 23, 2021

(54) MICROBIAL LYSOZYME FOR USE IN THE TREATMENT OF IRRITABLE BOWEL SYNDROME OR INFLAMMATORY BOWEL DISEASE

(71) Applicant: Novozymes A/S, Bagsvaerd (DK)

(72) Inventors: Soeren Kjaerulff, Holte (DK); Marianne Thorup Cohn, Nordhavn (DK); Nanna Ny Kristensen, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 136 days.

(21) Appl. No.: 16/473,201

(22) PCT Filed: Jan. 4, 2018

(86) PCT No.: PCT/EP2018/050189
§ 371 (c)(1),
(2) Date: Jun. 24, 2019

(87) PCT Pub. No.: WO2018/127532
PCT Pub. Date: Jul. 12, 2018

(65) Prior Publication Data
US 2019/0351032 A1 Nov. 21, 2019

(30) Foreign Application Priority Data

Jan. 4, 2017 (EP) ..................... 17150258
Feb. 8, 2017 (EP) ..................... 17155110
Dec. 21, 2017 (EP) ..................... 17209209

(51) Int. Cl.
*A61K 38/47* (2006.01)
*A23L 33/18* (2016.01)
*A61P 1/00* (2006.01)

(52) U.S. Cl.
CPC .............. *A61K 38/47* (2013.01); *A23L 33/18* (2016.08); *A61P 1/00* (2018.01); *C12Y 302/01017* (2013.01)

(58) Field of Classification Search
CPC .. A61K 38/47; A61K 2300/00; A61K 38/465; A61K 9/0053; A61K 9/0056; A61K 9/16; A61K 31/715; A61K 31/716; A61K 31/736; A61K 9/0029; A61K 9/0031; A61K 9/0095; A61K 9/2086; A61K 9/4891; C12Y 302/01017; C12Y 301/03026; A23K 20/189; A23K 50/75; A23K 40/30; A23K 50/30; A23L 33/18; A23L 29/06; A23L 33/195; A61P 1/00; A61P 1/14; A61P 13/12; A61P 1/16; A61P 3/00; A61P 43/00; A61P 9/00; A61P 29/00; A61P 3/04; C12N 9/16; C12N 9/2462; A23V 2002/00; A23V 2200/32

See application file for complete search history.

(56) References Cited

U.S. PATENT DOCUMENTS

| 10,568,344 B2 * | 2/2020 | Aureli ............ C12Y 302/01017 |
| 2010/0003235 A1 | 1/2010 | Hagie et al. |
| 2018/0184688 A1 * | 7/2018 | Aureli ..................... A23K 50/75 |
| 2018/0296475 A1 * | 10/2018 | Sandvang ...... C12Y 301/03026 |

FOREIGN PATENT DOCUMENTS

| GB | 2379166 A | | 3/2003 |
| WO | 2000021381 A1 | | 4/2000 |
| WO | 2004026334 A1 | | 4/2004 |
| WO | WO2007038623 | * | 4/2007 |
| WO | 2013076253 A1 | | 5/2013 |
| WO | 2017001703 A1 | | 1/2017 |

OTHER PUBLICATIONS

Lee et al, 2009, J Agric Food Chem 57(6), 2233-2240.
Masschlck et al, 2002, J Food Protection 65(12), 1916-1923.

* cited by examiner

*Primary Examiner* — Deborah K Ware
(74) *Attorney, Agent, or Firm* — Eric J. Fechter

(57) ABSTRACT

The present invention relates to microbial lysozyme, compositions comprising such and uses thereof.

Figure 1:
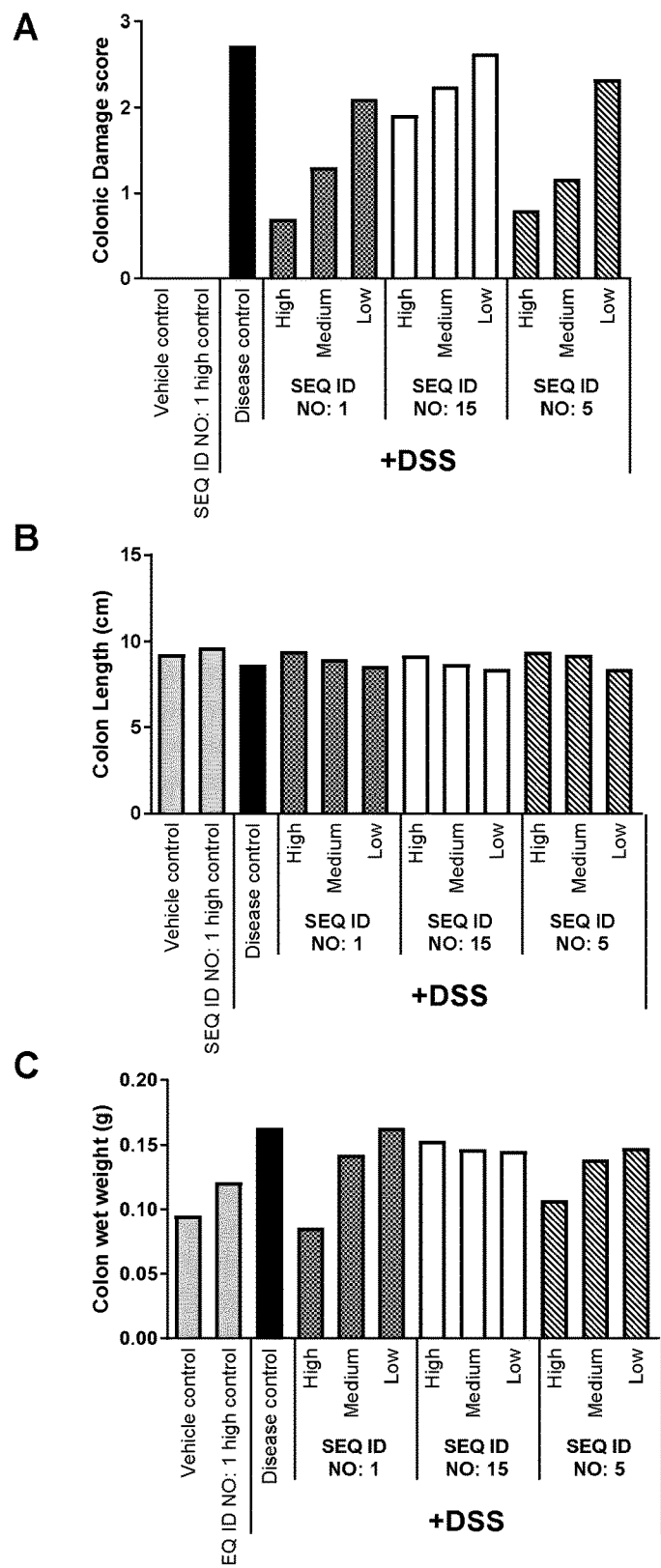

15 Claims, 7 Drawing Sheets
Specification includes a Sequence Listing.

MICROBIAL LYSOZYME FOR USE IN THE TREATMENT OF IRRITABLE BOWEL SYNDROME OR INFLAMMATORY BOWEL DISEASE

CROSS-REFERENCE TO RELATED APPLICATIONS

This application is a 35 U.S.C. 371 national application of PCT/EP2018/050189, filed Jan. 4, 2018, which claims priority or the benefit under 35 U.S.C. 119 of European application no. 17150258.6, filed Jan. 4, 2017, European application no. 17155110.4, filed Feb. 8, 2017, and European application no. 17209209.0, filed Dec. 21, 2017. The contents of these applications are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to microbial lysozyme and compositions comprising such for stabilizing the healthy microbiota and suppressing growth and/or intestinal colonization of bacterial pathogens in the gastrointestinal (GI) tract, and for preventing, alleviating or treating Irritable Bowel Syndrome (IBS) or Inflammatory Bowel Disease (IBD).

BACKGROUND OF THE INVENTION

The intestinal flora of humans contains a large number of bacteria which play an important role in the intestinal health of humans. The distal ileum contains 10e7 to 10e8 primarily anaerobic bacteria/gram of luminal contents, whereas the colon has 10e11 to 10e12 bacterial colonies/gram, with *Bacteroides, Clostridium*, and *Bifidobacterium* species predominating. Chronic intestinal inflammation is the consequence of an overly aggressive cell-mediated immune response to commensal (normal endogenous) enteric bacteria in a genetically susceptible host.

Inflammatory Bowel Disease (IBD) is a debilitating illness characterized by chronic intestinal inflammation that often shows an intermittent course with acute attacks followed by periods of remission. Clinical symptoms during acute attacks include diarrhea, bleeding, abdominal pain, fever, joint pain, and weight loss. IBD can manifest itself in a variety of forms, the most common of which are Crohn's disease (a chronic transmural inflammation of the bowel, which can affect the whole gastrointestinal tract) and ulcerative colitis (a chronic inflammatory bowel disease affecting the colon). Ulcerative colitis and Crohn's disease occur in areas of the gastrointestinal tract with the highest concentrations of luminal bacteria.

Lysozyme is an O-glycosyl hydrolase produced as a defensive mechanism against bacteria by many organisms. The enzyme causes the hydrolysis of bacterial cell walls by cleaving the glycosidic bonds of peptidoglycan. After having their cell walls weakened by lysozyme action, bacterial cells lyse as a result of unbalanced osmotic pressure. In addition, lysozyme can degrade extracellular peptidoglycan into soluble fragments, which seems to limit inflammation.

Lysozyme has been classified into five different glycoside hydrolase (GH) families (CAZy, www.cazy.org): hen egg-white lysozyme (GH22), goose egg-white lysozyme (GH23), bacteriophage T4 lysozyme (GH24), *Sphingomonas* flagellar protein (GH73) and Chalaropsis lysozymes (GH25). Lysozymes from the families GH23 and GH24 are primarily known from bacteriophages and have only recently been identified in fungi. The lysozyme family GH25 has been found to be structurally unrelated to the other lysozyme families.

Lysozyme has traditionally been extracted from hen egg white due to its natural abundance. Lysozyme extracted from hen egg white is the primary product available on the commercial market, but does not cleave N,6-O-diacetylmuramic acid in e.g. *Staphylococcus aureus* cell walls and is thus unable to lyse this important human pathogen among others (Masschalck B, Deckers D, Michiels C W (2002), "Lytic and nonlytic mechanism of inactivation of gram-positive bacteria by lysozyme under atmospheric and high hydrostatic pressure", J Food Prot. 65(12):1916-23).

WO2000/21381, GB2379166 and WO2004/026334 each discloses a composition comprising a GH22 lysozyme from hen egg white. The mature amino acid sequence of a wild type GH25 lysozyme from *Acremonium alcalophilum* is disclosed in WO 2013/076253.

There is a need for a composition which upon administration changes the microbiota to the benefit of humans having an undesirable microbiota such as patients suffering from e.g. IBD and/or IBS. The present invention provides a method for obtaining such changes.

SUMMARY OF THE INVENTION

The invention provides microbial lysozymes and compositions comprising such for various uses. In one aspect, the invention provides for microbial lysozymes and compositions comprising such for use in a method of preventing, alleviating or treating Irritable Bowel Syndrome (IBS) or Inflammatory Bowel Disease (IBD).

In one aspect, the microbial lysozyme or composition comprising such stabilizes the healthy microbiota in the gastrointestinal (GI) tract and suppresses growth and/or intestinal colonization of bacterial pathogens. In a further aspect, the microbial lysozyme or composition comprising such prevents, alleviates or treats inflammation, and in a yet further aspect the microbial lysozyme or composition comprising such reduces ectopic lipid deposition associated with obesity such as e.g. diet induced obesity.

Also described herein is a method of preventing, alleviating or treating Irritable Bowel Syndrome (IBS) or Inflammatory Bowel Disease (IBD).

A method of improving the intestinal health in humans is furthermore describe, where the method comprises reducing the amount of dead *Lactobacillus johnsonii* cells in the digestive tract, comprising providing to said human an isolated polypeptide having lysozyme activity against *Lactobacillus johnsonii*.

Overview of Sequence Listing

SEQ ID NO: 1 is the mature amino acid sequence of a wild type GH25 lysozyme from *Acremonium alcalophilum* as described in WO 2013/076253.

SEQ ID NO: 2 is the gene sequence of the GH24 lysozyme as isolated from *Trichophaea saccata*.

SEQ ID NO: 3 is the amino acid sequence as deduced from SEQ ID NO: 2.

SEQ ID NO: 4 is the mature amino acid sequence of a wild type GH24 lysozyme from *Trichophaea saccata*.

SEQ ID NO: 5 is the mature amino acid sequence of a wild type GH22 lysozyme from *Gallus gallus* (hen egg white lysozyme).

SEQ ID NO: 6 is primer F-80470.

SEQ ID NO: 7 is primer R-80470.

SEQ ID NO: 8 is primer 8643.

SEQ ID NO: 9 is primer 8654.

SEQ ID NO: 10 is the forward primer 27F.

SEQ ID NO: 11 is the reverse primer 534R.

SEQ ID NO: 12 is a sequence representing the 16S rRNA gene classified as *Faecalibacterium prausnitzii* as described in Duncan, S. H. et al., Int. J. Syst. Evol. Microbiol. 52 (PT 6), 2141-2146 (2002) and submitted 19 Sep. 2001 by Hold G. L. to Gut Microbiology and Immunology.

SEQ ID NO: 13 is the genomic DNA sequence of a GH25 lysozyme as isolated from *Myceliophthora fergusii*.

SEQ ID NO: 14 is the amino acid sequence as deduced from SEQ ID NO: 13.

SEQ ID NO: 15 is the amino acid sequence of the mature GH25 lysozyme from *Myceliophthora fergusii*.

SEQ ID NO: 16 is the cDNA sequence of a GH25 lysozyme as isolated from *Lecanicillium* sp. WMM742.

SEQ ID NO: 17 is the amino acid sequence as deduced from SEQ ID NO: 16.

SEQ ID NO: 18 is the amino acid sequence of the mature GH25 lysozyme from *Lecanicillium* sp. WMM742.

SEQ ID NO: 19 is the cDNA sequence of a GH25 lysozyme as isolated from *Zygomycetes* sp. XZ2655.

SEQ ID NO: 20 is the amino acid sequence as deduced from SEQ ID NO: 19.

SEQ ID NO: 21 is the amino acid sequence of the mature GH25 lysozyme from *Zygomycetes* sp. XZ2655.

SEQ ID NO: 22 is the cDNA sequence of a GH25 lysozyme as isolated from *Malbranchea flava*.

SEQ ID NO: 23 is the amino acid sequence as deduced from SEQ ID NO: 22.

SEQ ID NO: 24 is the amino acid sequence of the mature GH25 lysozyme from *Malbranchea flava*.

SEQ ID NO: 25 is the codon optimised DNA the GH25 lysozyme as isolated from *Hypholoma polytrichi*.

SEQ ID NO: 26 is the amino acid sequence as deduced from SEQ ID NO: 25.

SEQ ID NO: 27 is the amino acid sequence of the mature GH25 lysozyme from *Hypholoma polytrichi*.

SEQ ID NO: 28 is the cDNA sequence of a GH25 lysozyme as isolated from *Engyodontium album*.

SEQ ID NO: 29 is the amino acid sequence as deduced from SEQ ID NO: 28.

SEQ ID NO: 30 is the amino acid sequence of the mature GH25 lysozyme from *Engyodontium album*.

FIGURES

FIG. 1 shows for Example 6 the raw colonic damage scores (A), colon length (B) and colon wet weight (C) of mice treated with High, Medium or Low dose of SEQ ID NO: 1, SEQ ID NO: 15 or SEQ ID NO: 5 followed by dextran sulfate sodium (DSS, 3%) treatment compared to vehicle control, SEQ ID NO: 1 treatment without DSS and disease control (DSS treatment without Lysozyme treatment). Each column represents the mean of n=10-12.

Figure 2:
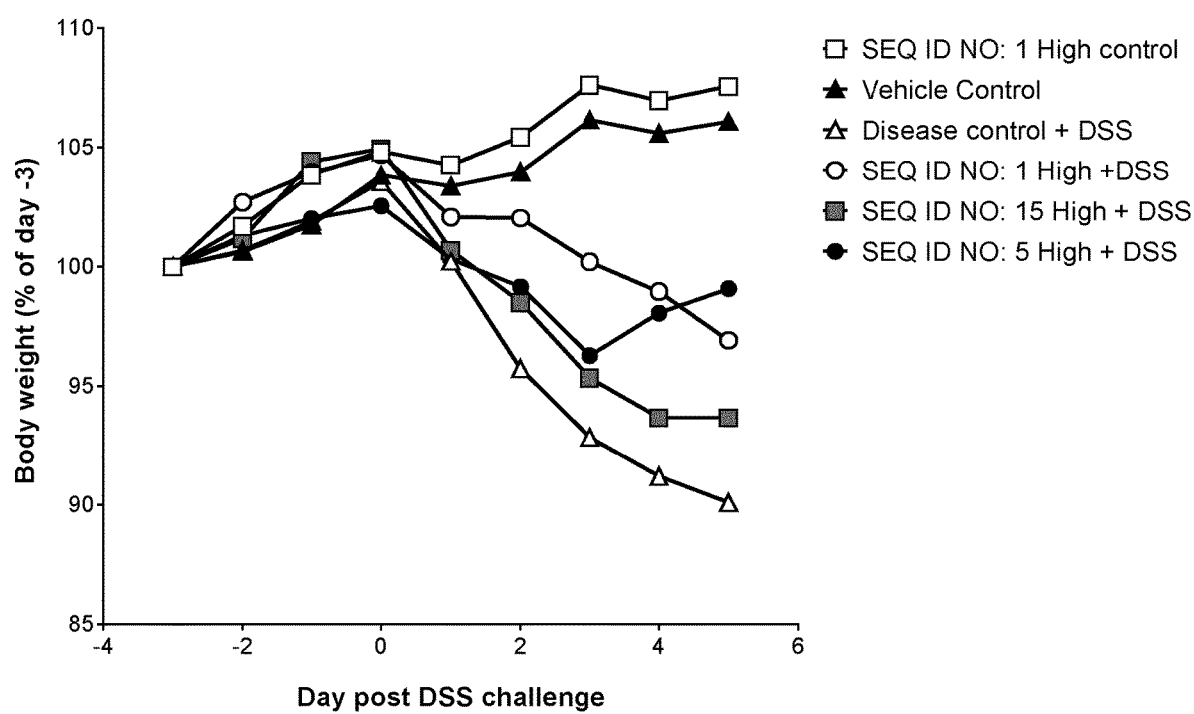

FIG. 2 shows a for Example 6 comparison of weight development following treatment with high dose of SEQ ID NO: 1, SEQ ID NO: 15 and SEQ ID NO: 5 compared to controls. Line graph representing changes in the average body weight of each group relative to the weight at day −3 (where prophylactic treatment started. DSS challenge were started at day 0. Each line corresponds to each of the indicated treatments over the course of the experiment (n=10-12).

Figure 3:
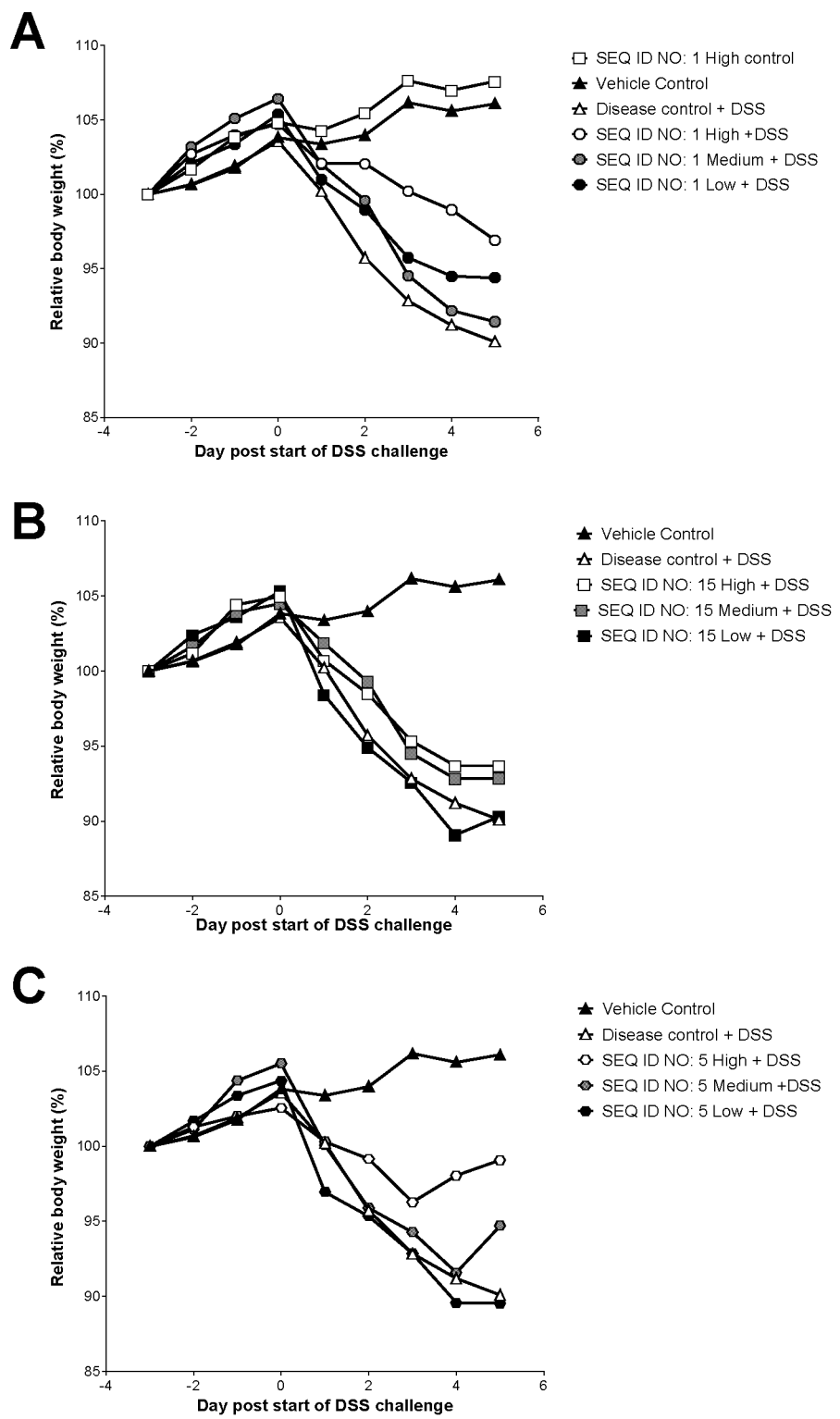

FIG. 3 shows for Example 6 a comparison of weight development following treatment with high, medium and low dose of SEQ ID NO: 1 (A), SEQ ID NO. 15 (B) or SEQ ID NO. 5 (C) compared to controls. Line graph representing changes in the average body weight of each group relative to the weight at day 3. Each line corresponds to each of the indicated treatments over the course of the experiment (n=10-12).

Figure 4:
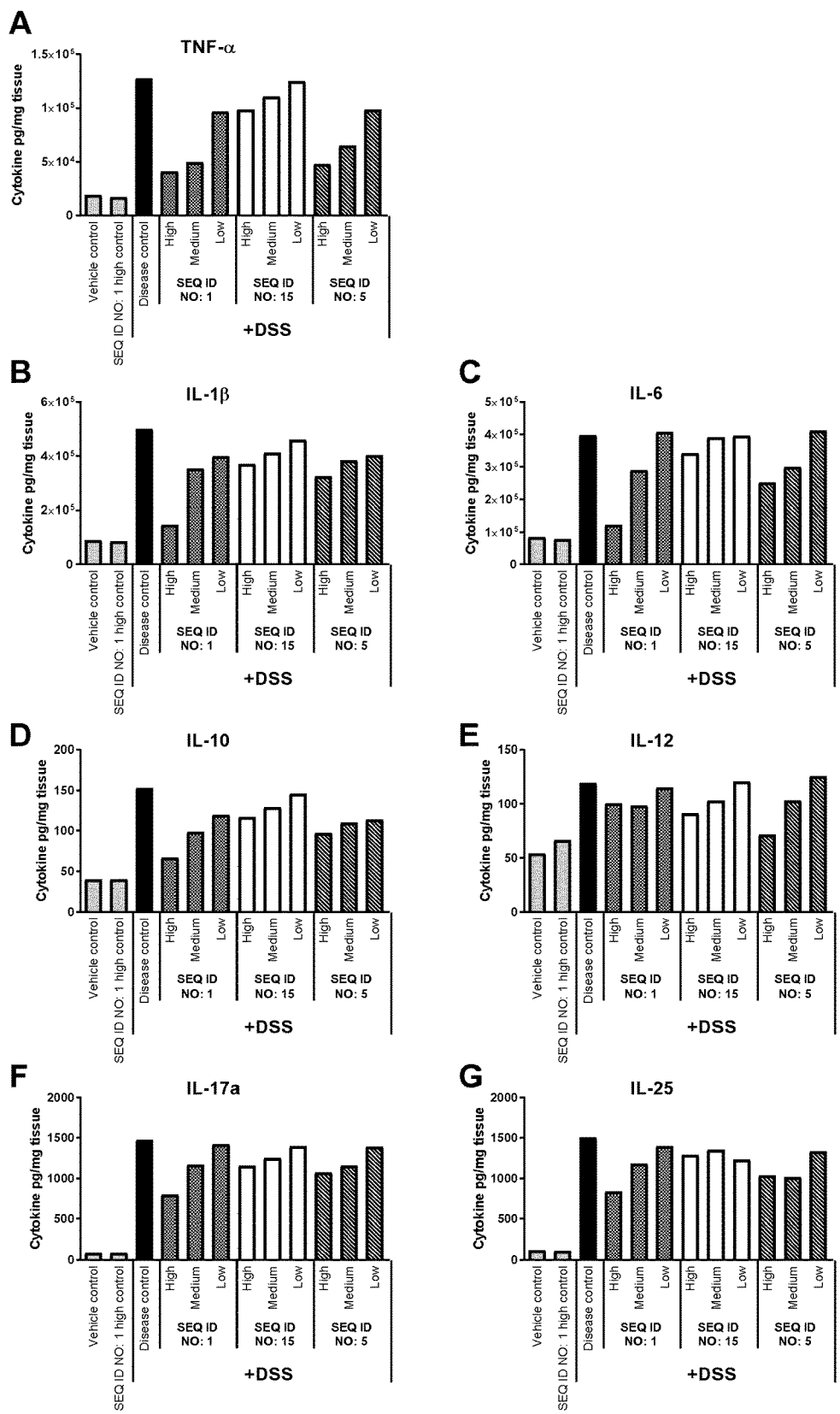

FIG. 4 shows for Example 6 the effect of SEQ ID NO. 1, SEQ ID NO. 15 and SEQ ID NO. 5 on cytokine levels in colon tissue at day 5 post start of DSS challenge. Concentrations of TNFα (A), IL-1β (B), IL-6 (C), IL-10 (D), IL-12 (E), IL-17a (F) & IL-25 (G) pr. mg colon tissue are shown in response to each test compound dosed in High, Medium or Low concentration compared to controls. Each column represents the mean of n=10-12 mice.

Figure 5:
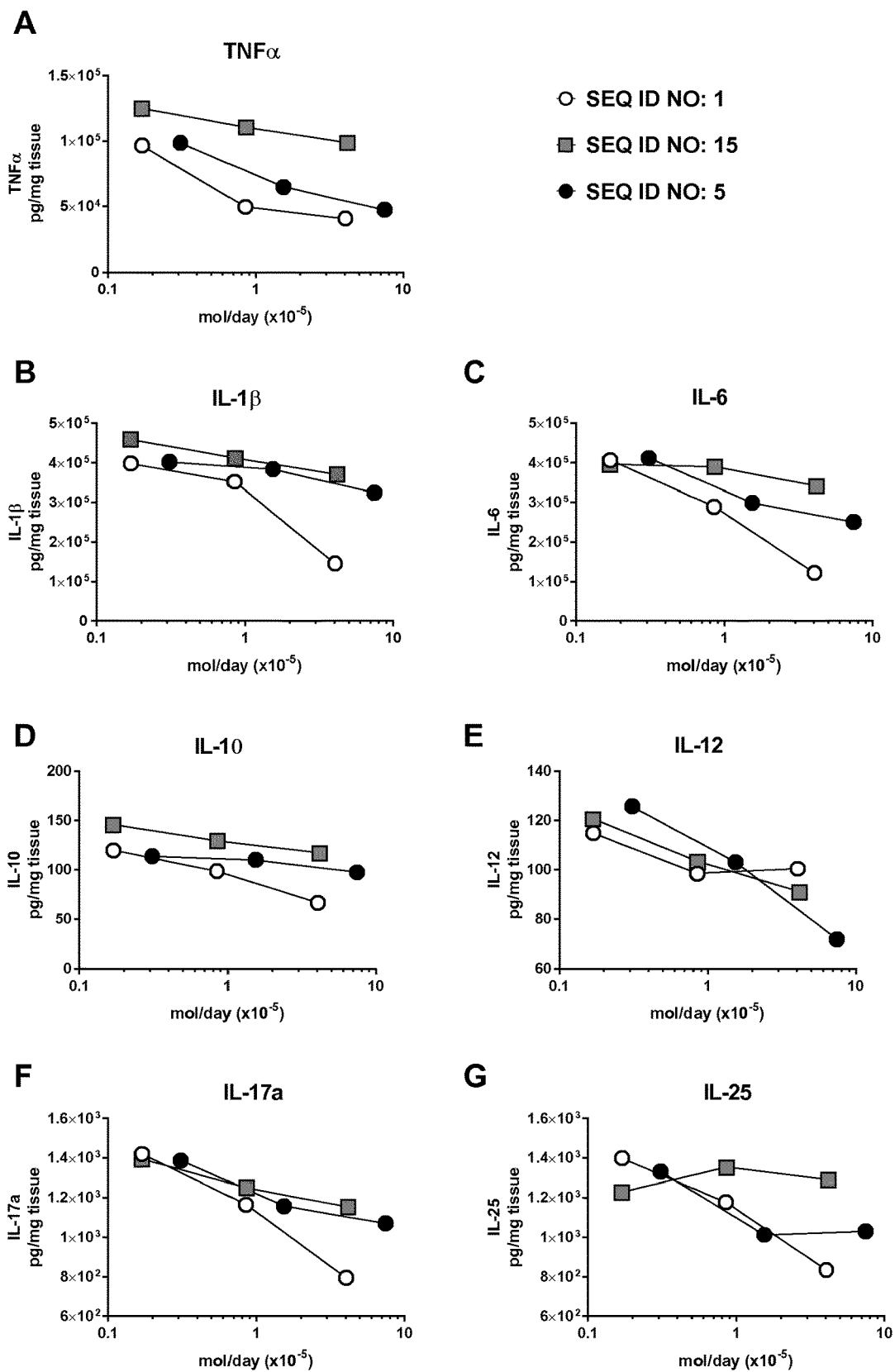

FIG. 5 shows for Example 6 the effect of SEQ ID NO. 1, SEQ ID NO. 15 and SEQ ID NO. 5 on cytokine levels in colon tissue at day 5 post start of DSS challenge. Concentrations of TNFα (A), IL-1β (B), IL-6 (C), IL-10 (D), IL-12 (E), IL-17a (F) & IL-25 (G) pr. mg colon tissue are shown in response to each test compound dosed in mol/day. Each point represents the mean of n=10-12.

Figure 6:
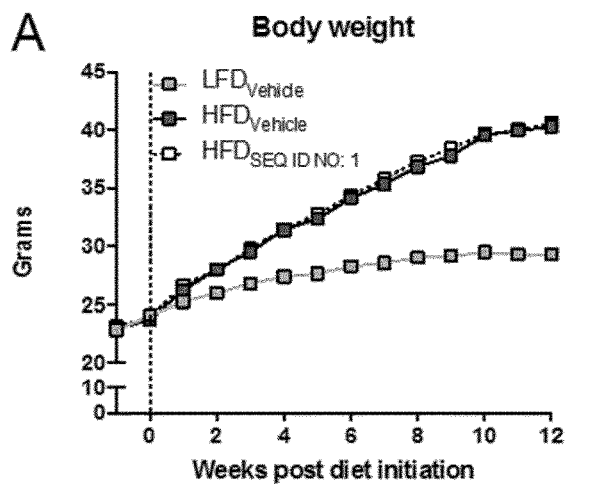
Figure 6:
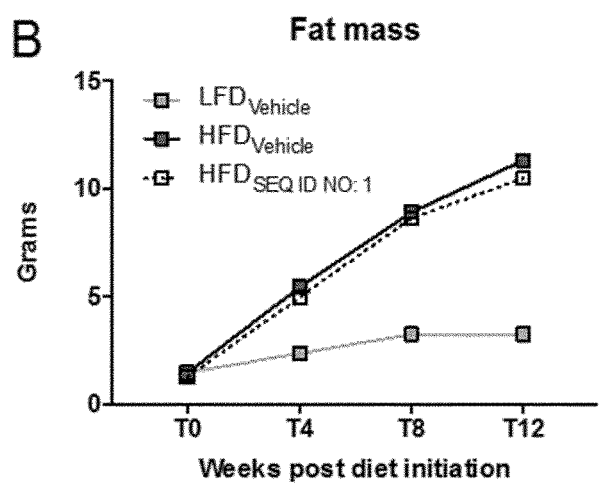
Figure 6:
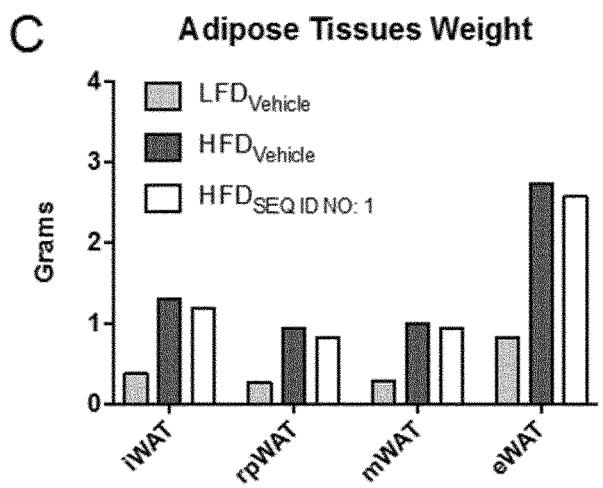

FIG. 6 shows weight development of mice from Example 7 from one week before diet start and throughout the study (A), Fat mass analysed at indicated time points (B) and tissue weight at termination (C). Each column/dot represents the mean of n=10-12.

Figure 7:
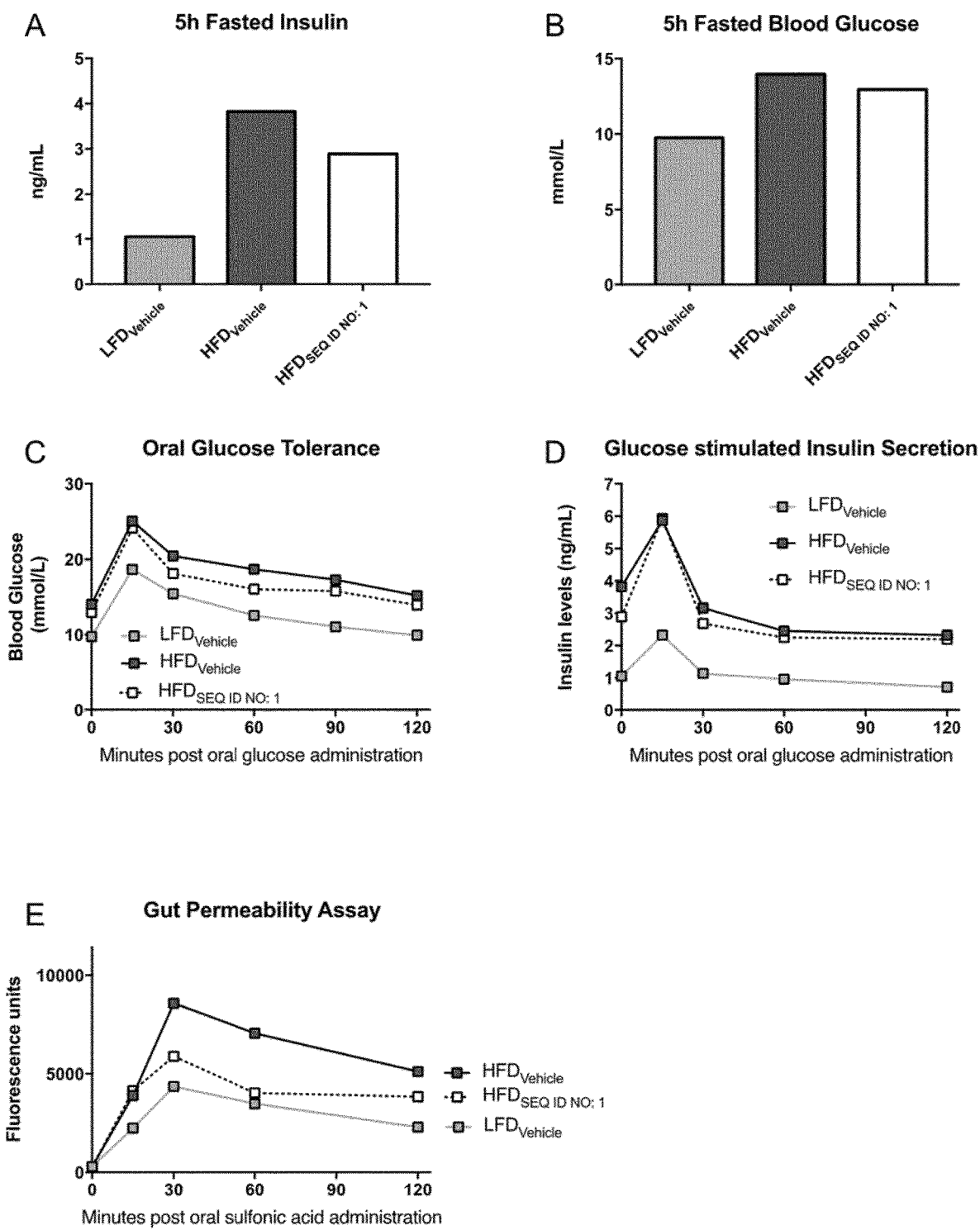

FIG. 7 shows for mice treated as described in Example 7: 5 h fasted Blood Glucose (A) 5 h fasted Insulin (B), Blood glucose levels at indicated time points after Oral challenge with 2 grams glucose per kilo lean mass (C), Plasma levels of the endogenous insulin response to the glucose challenge (D) and Gut permeability (E). All measures were performed after 10 weeks of High Fat Diet (HFD) feeding and daily gavage treatments. Each column/dot represents the mean of n=10-12.

DEFINITIONS

Diet induced obesity: Diet-induced obesity (DIO) is obesity caused by eating (humans) or being fed (animal model) high-fat and/or high-density diets.

Ectopic lipid deposition: The term "lipid deposition" is used for deposition of body fat. Ectopic fat is the storage of triglycerides within cells of non-adipose tissue that normally contain only small amounts of fat such as the liver, skeletal muscle, heart, and pancreas. Thus the term "ectopic lipid deposition" means fat stored in tissues such as the liver, skeletal muscle, heart and pancreas.

*Faecalibacterium*: It is known (Větrovský T, Baldrian P (2013) The Variability of the 16S rRNA Gene in Bacterial Genomes and Its Consequences for Bacterial Community Analyses. PLoS ONE 8(2): e57923. doi: 10.1371/journal.pone.0057923) that the 16S rRNA gene sequence identity varies within a genus. It has been shown that the mean identity is 95.56 with a standard deviation of 3.68. It was also found that 12.2% of genera contain species with mean pairwise 16S rRNA gene similarity below 90%. SEQ ID NO: 12 contains 16S rRNA gene sequences classified as genus *Faecalibacterium prausnitzii* as described in Duncan, S. H. et al., Int. J. Syst. Evol. Microbiol. 52 (PT 6), 2141-2146 (2002) and submitted 19 Sep. 2001 by Hold G. L. to Gut Microbiology and Immunology. Thus strains are hereby defined as *Faecalibacterium* wherein the sequence identity of the V1-V3 region of the 16S rRNA gene of said strain has at least 90% e.g., at least 91%, at least 92%, at least 93%, at least 94%, at least 95%, at least 96%, at least 97%, at least 98%, at least 99%, or 100% sequence identity to SEQ ID NO: 12.

Food composition: A "food composition" is any composition, which can be administered to a human as a food. As used herein, a food composition is the same as a "dietetic composition".

Fragment: The term "fragment" means a polypeptide or a catalytic domain having one or more (e.g., several) amino acids absent from the amino and/or carboxyl terminus of a mature polypeptide or domain; wherein the fragment has lysozyme. In one aspect, a fragment comprises at least 170 amino acids, such as at least 175 amino acids, at least 177 amino acids, at least 180 amino acids, at least 185 amino acids, at least 190 amino acids, at least 195 amino acids or at least 200 amino acids of SEQ ID NO: 1 and has lysozyme activity.

In another aspect, a fragment comprises at least 210 amino acids, such as at least 215 amino acids, at least 220 amino acids, at least 225 amino acids, at least 230 amino acids, at least 235 amino acids or at least 240 amino acids of SEQ ID NO: 4 and has lysozyme activity.

In another aspect, a fragment comprises at least 170 amino acids, such as at least 175 amino acids, at least 177 amino acids, at least 180 amino acids, at least 185 amino acids, at least 190 amino acids, at least 195 amino acids or at least 200 amino acids of SEQ ID NO: 15 and has lysozyme activity.

Glucose dysregulation: The term "glucose dyregulation" is a disorder in the metabolism and regulation of blood glucose levels. Examples of conditions primarily caused by glucose dysregulation include hypoglycemia, hyperglycemia, insulin resistance, hyperinsulinemia, Syndrome X, metabolic syndrome, and diabetes.

Increases the proportion of bacteria of x in the microbiota of the GI tract: The term "increases the proportion of bacteria of x in the microbiota of the GI tract" means that the quantity of bacteria of a specific taxonomic rank (e.g. order or genus) has increased compared to a control sample. Samples of microbiota can be taken from the gut (i.e. gastrointestinal tract) and analysed by examining the sequences (reads) of the 16S rRNA genes in the sample. The reads of the 16S rRNA genes can be clustered together based on sequence identity and each cluster can be compared to a database of known sequences of the 16S rRNA gene to identify the type of bacteria in that cluster. The clusters can be merged at different taxonomic levels (phylum, class, order, family, genus or species) to give a quantitative analysis of the amount of bacteria within each taxonomy level over the entire sample By comparing the clusters from a control person to a person administered with a lysozyme of the invention, differences in the microbiota can be determined. Examples of such determination include differences in e.g. the proportion of bacteria of genus *Faecalibacterium* in the microbiota taken from animals or humans administered with a lysozyme compared to a control not administered with a lysozyme or the proportion of bacteria of order Clostridiales in the microbiota taken from animals or humans administered with a lysozyme compared to control Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Lysozyme activity: The term "lysozyme activity" means the enzymatic hydrolysis of the 1,4-beta-linkages between N-acetylmuramic acid and N-acetyl-D-glucosamine residues in a peptidoglycan or between N-acetyl-D-glucosamine residues in chitodextrins, resulting in bacteriolysis due to osmotic pressure. Lysozyme belongs to the enzyme class EC 3.2.1.17. Lysozyme activity is typically measured by turbidimetric determination. The method is based on the changes in turbidity of a suspension of *Micrococcus luteus* ATCC 4698 induced by the lytic action of lysozyme. In appropriate experimental conditions these changes are proportional to the amount of lysozyme in the medium (c.f. INS 1105 of the Combined Compendium of Food Additive Specifications of the Food and Agriculture Organisation of the UN (www.fao.org)). For the purpose of the present invention, lysozyme activity is determined according to the turbidity assay described in example 5 ("Determination of Lysozyme Activity"). In one aspect, the polypeptides of the present invention have at least 20%, e.g., at least 40%, at least 50%, at least 60%, at least 70%, at least 80%, at least 90%, at least 95%, or at least 100% of the lysozyme activity of SEQ ID NO: 1. In one aspect, the polypeptides of the present invention have at least 20%, e.g., at least 40%, at least 50%, at least 60%, at least 70%, at least 80%, at least 90%, at least 95%, or at least 100% of the lysozyme activity of SEQ ID NO: 4. In one aspect, the polypeptides of the present invention have at least 20%, e.g., at least 40%, at least 50%, at least 60%, at least 70%, at least 80%, at least 90%, at least 95%, or at least 100% of the lysozyme activity of SEQ ID NO: 15.

Mature polypeptide: The term "mature polypeptide" means a polypeptide in its final form following translation and any post-translational modifications, such as N-terminal processing, C-terminal truncation, glycosylation, phosphorylation, etc.

Medical device: A medical device is herein understood as a product which meets the definition for a medical device in section 201(h) of the US Federal Food Drug & Cosmetic (FD&C) Act including an instrument, apparatus, implement, machine, contrivance, implant, in vitro reagent, or other similar or related article, including a component part, or accessory which is recognized in the official National Formulary, or the United States Pharmacopoeia, or any supplement to them, intended for use in the cure, mitigation, treatment, or prevention of disease, in man or other animals, or intended to affect the structure or any function of the body of man or other animals, and which does not achieve its primary intended purposes through chemical action within or on the body of man or other animals and which is not dependent upon being metabolized for the achievement of any of its primary intended purposes."

Microbial lysozyme: The term "microbial lysozyme" means a polypeptide having lysozyme activity which is obtained or obtainable from a microbial source. Examples of microbial sources are fungi; i.e. the lysozyme is obtained or obtainable from the kingdom Fungi, wherein the term kingdom is the taxonomic rank. In particular, the the microbial lysozyme is obtained or obtainable from the phylum Ascomycota, such as the sub-phylum Pezizomycotina, wherein the terms phylum and sub-phylum is the taxonomic ranks.

If the taxonomic rank of a polypeptide is not known, it can easily be determined by a person skilled in the art by performing a BLASTP search of the polypeptide (using e.g. the National Center for Biotechnology Information (NCIB) website http://www.ncbi.nlm.nih.gov/) and comparing it to the closest homologues. An unknown polypeptide which is a fragment of a known polypeptide is considered to be of the same taxonomic species. An unknown natural polypeptide or artificial variant which comprises a substitution, deletion and/or insertion in up to 10 positions is considered to be from the same taxonomic species as the known polypeptide.

Obtained or obtainable from: The term "obtained or obtainable from" means that the polypeptide may be found in an organism from a specific taxonomic rank. In one embodiment, the polypeptide is obtained or obtainable from the kingdom Fungi, wherein the term kingdom is the taxonomic rank. In a preferred embodiment, the polypeptide is obtained or obtainable from the phylum Ascomycota, wherein the term phylum is the taxonomic rank. In another preferred embodiment, the polypeptide is obtained or obtainable from the subphylum Pezizomycotina, wherein the term subphylum is the taxonomic rank. In another preferred embodiment, the polypeptide is obtained or obtainable from the class Eurotiomycetes, wherein the term class is the taxonomic rank.

If the taxonomic rank of a polypeptide is not known, it can easily be determined by a person skilled in the art by performing a BLASTP search of the polypeptide (using e.g. the National Center for Biotechnology Information (NCIB) website http://www.ncbi.nlm.nih.gov/) and comparing it to the closest homologues. An unknown polypeptide which is a fragment of a known polypeptide is considered to be of the same taxonomic species. An unknown natural polypeptide or artificial variant which comprises a substitution, deletion and/or insertion in up to 10 positions is considered to be from the same taxonomic species as the known polypeptide.

Operational taxonomic unit (OTU): The term "Operational taxonomic unit" means a cluster of sequences with a certain degree of similarity. In this case, 97 percent is chosen as the threshold for assigning sequences of the 16S rRNA gene to different OTUs, meaning that all sequences within a single OTU have at least 97 percent sequence identity. At this identity level each OTU is often considered (or assumed) to represent a single bacterial species.

Post-surgery flare up: Means intensification of a disease or condition after surgery. Thus, with the expression "prevent, alleviate or treat post-surgery flare-ups of IBS and/or IBD" is meant that the risk that IBS and/or IBD appears after surgery, is prevented, alleviated or treated.

Preventing: Means stopping or hindering a disease, disorder, or symptom of a disease or condition through some action.

Remission (of a condition): Means a period in the course of a disease when symptoms become less severe. Thus, with the expression "maintain remission of IBS and/or IBD" is meant that the risk of IBS and/or IBD reappearing is prevented or alleviated.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

$$(\text{Identical Residues} \times 100)/(\text{Length of Alignment} - \text{Total Number of Gaps in Alignment})$$

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well known recombinant methods or by classical purification methods.

Therapeutic composition: A "therapeutic composition" is any non-food composition comprising a pharmaceutically active ingredient for administration to a human, which is used for preventing, alleviating or treating a disease. Examples of therapeutic compositions include but are not limited to a powder, tablet, such as a lozenge or effervescent tablet, a capsule, a component of an emulsion or a paste, an individual sachet, chewing gum, or in more general compositions such as oil drops or in any other suitable carrier determined by those of skill in the art to be an effective carrier for microorganisms.

Variant: The term "variant" means a polypeptide having lysozyme activity comprising an alteration, i.e., a substitution, insertion, and/or deletion, of one or more (several) amino acid residues at one or more (e.g., several) positions. A substitution means replacement of the amino acid occupying a position with a different amino acid; a deletion means removal of the amino acid occupying a position; and an insertion means adding 1, 2, or 3 amino acids adjacent to and immediately following the amino acid occupying the position.

In one aspect, a lysozyme variant according to the invention may comprise from 1 to 5; from 1 to 10; from 1 to 15; from 1 to 20; from 1 to 25; from 1 to 30; from 1 to 35; from 1 to 40; from 1 to 45; or from 1-50, i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 alterations and have at least 20%, e.g., at least 40%, at least 50%, at least 60%, at least 70%, at least 80%, at least 90%, at least 95%, or at least 100% of the lysozyme activity of the parent lysozyme, such as SEQ ID NO: 1, SEQ ID NO: 4 or SEQ ID NO: 15.

DETAILED DESCRIPTION OF THE INVENTION

It has been found that a composition such as a food or pharmaceutical composition or a medical device comprising a microbial lysozyme, when provided to a human, results in a change in the microbiota, which may be beneficial for improving the health of humans.

In one embodiment, a method is herein described for preventing, alleviating or treating Irritable Bowel Syndrome (IBS) and/or Inflammatory Bowel Disease (IBD). In one embodiment the method comprises providing and administering a composition such as e.g. a food or pharmaceutical composition or a medical device comprising one or more microbial lysozymes. In one embodiment the microbial lysozyme is obtained or obtainable from the kingdom Fungi.

It has thus been found by the inventors that microbial lysozyme is suitable for administering to patients suffering from Irritable Bowel Syndrome (IBS) and/or Inflammatory Bowel Disease (IBD).

In one embodiment the method is for preventing, alleviating or treating patients suffering from Irritable Bowel Syndrome (IBS) and/or Inflammatory Bowel Disease (IBD) during a period of remission, wherein the period of remission is a period in which the severity of IBS and/or IBD symptoms is temporary diminished. In one embodiment is for preventing, alleviating or treating patients suffering from Crohn's disease or Ulcerative colitis during a period of remission, wherein the period of remission is a period in which the severity of IBS and/or IBD symptoms is temporary diminished.

The microbial lysozyme described herein may also be administered for obtaining weight gain of e.g. people such as elderly people being hospitalized. In one embodiment the method comprises administering one or more microbial lysozymes to patients after operation. In one embodiment the method is for weight management such as e.g. for retaining the weight to a desired level. In one embodiment the method is for weight management of hospitalized patients in risk of losing weight after surgery or during hospitalization in general.

In one embodiment, the invention relates to the use of a composition comprising microbial lysozyme for obtaining weight gain of a person wherein the food or food additive comprises one or more microbial lysozymes.

In one embodiment, the weight is increased by at least 1%, such as by at least 1.5%, at least 2.0%, at least 2.5%, at least 3%, at least 3.5%, at least 4% or at least 5% compared to a control not receiving a composition comprising microbial lysozyme. In another embodiment, the weight is increased by between 1% and 15%, such as between 1% and 12%, between 1% and 10%, 1.5% and 8%, 2.0% and 7% compared to the control, or any combination of these intervals.

The invention furthermore relates to the use of polypeptides which have lysozyme activity against *Lactobacillus johnsonii*. *Lactobacillus johnsonii* is an important bacterium of the intestinal flora of humans. Without being bound to a particular theory, it is believed that removal of dead *Lactobacillus johnsonii* cells from the intestinal flora, by means of enzymatic lyses of the partially degraded bacterial cell wall, to be an important contributor to intestinal health of a human.

In one embodiment of the invention, the polypeptides of the invention have improved lysozyme activity compared to the lysozyme activity of hen eggwhite lysozyme (SEQ ID NO: 5) as determined by Method for the Determination of Lysozyme Activity Against *Lactobacillus johnsonii*.

An aspect of the invention is directed to a method of improving the intestinal health in humans comprising reducing the amount of dead *Lactobacillus johnsonii* cells, or cell wall debris therefrom, in the digestive tract, comprising providing a polypeptide as defined by the invention to a human.

An aspect of the invention is directed to a method of improving the intestinal health in humans comprising reducing the amount of dead *Lactobacillus johnsonii* cells, or cell wall debris therefrom, in the digestive tract, comprising providing a polypeptide selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO: 1.

An aspect of the invention is directed to a method of promoting the elimination of dead *Lactobacillus johnsonii* cells, or cell wall debris therefrom, from the digestive tract comprising providing to a human a polypeptide or source of a polypeptide selected from the group consisting of a polpypeptide having at least 90% sequence identity to the polypeptide of SEQ ID NO: 15, a polpypeptide having at least 90% sequence identity to the polypeptide of SEQ ID NO: 18, a polpypeptide having at least 90% sequence identity to the polypeptide of SEQ ID NO: 21, a polpypeptide having at least 90% sequence identity to the polypeptide of SEQ ID NO: 24, a polpypeptide having at least 90% sequence identity to the polypeptide of SEQ ID NO: 27, and a polpypeptide having at least 90% sequence identity to the polypeptide of SEQ ID NO: 30 or a polypeptide or source of a polypeptide selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO: 1.

Over the past years, an increasing number of studies have clearly described the importance of *Faecalibacterium* as a component of the healthy human microbiota. For example, *F. prausnitzii*, has a low prevalence in many intestinal disorders, particularly in IBD patients (Current Opinion in Microbiology 16(3), pp 1-7, July 2013).

In one embodiment, compositions, methods and uses of the invention are highly efficient in the treatment or prevention of conditions associated with a low abundance of *Faecalibacterium* in the GI tract. In a further embodiment, compositions, methods and uses of the invention provide an increase of *Faecalibacterium* in the GI tract.

In one aspect, the invention relates to one or more polypeptides having lysozyme activity or a composition comprising such as e.g. a food or pharmaceutical composition or a medical device comprising one or more polypeptides having lysozyme activity, wherein the polypeptide is from glycosyl hydrolyase family 24 (GH24) or glycosyl hydrolyase family 25 (GH25) and is obtained or obtainable from the kingdom Fungi.

In one aspect, the polypeptide having lysozyme activity used in the method of the invention is a microbial lysozyme. In one embodiment, the composition used in the invention such as e.g. a food or pharmaceutical composition or a medical device comprising one or more microbial lysozymes may for example be used to stabilize the healthy microbiota of humans by suppressing growth/intestinal colonization of bacterial pathogens such as *Clostridium perfringens, Clostridium difficile, Escherichia coli, Campylobacter coli*, and *Campylobacter jejuni, Yersinia* spp., *Shigella* spp. and *Salmonella* spp., such as *Salmonella enterica* and *Salmonella typhimurium, Listeria monocytogenes, Enterococcus* spp. and *Helicobacter pylori*. In a further embodiment a lysozyme of the present invention provides a positive effect on the microbial balance of the digestive tract.

In one embodiment, the composition used in the invention increases the proportion of bacteria of order Clostridiales in the microbiota of the GI tract. In an embodiment, the proportion of bacteria of order Clostridiales is increased by at least 1%, such as at least 1.5%, at least 2%, at least 2.5%, at least 5% or at least 7.5%. In an alternative embodiment, the proportion of bacteria of order Clostridiales is increased by a factor of at least 1.25, such as at least 1.50, at least 1.75, at least 2.0, at least 2.5 or at least 3.0.

In one embodiment, the microbial lysozyme is of fungal origin. In one embodiment, the microbial lysozyme is obtained or obtainable from the kingdom Fungi. In an embodiment, the microbial lysozyme is obtained or obtainable from the phylum Ascomycota, such as the sub-phylum Pezizomycotina. In one embodiment, the microbial lysozyme is obtained or obtainable from the class Eurotiomycetes. In a further embodiment, the microbial lysozyme is obtained or obtainable from the order Eurotiales. In yet a further embodiment, the microbial lysozyme is obtained or obtainable from the family Aspergillaceae. In yet a further embodiment, microbial lysozyme is obtained or obtainable from the genus *Aspergillus*.

In one embodiment, the microbial lysozyme comprises one or more domains selected from the list consisting of GH24 and GH25. In one embodiment, the microbial lysozyme comprises one or more domains from GH24. In one embodiment, the microbial lysozyme comprises one or more domains from GH25.

In one embodiment, the invention relates to a method of increasing the proportion of bacteria of genus *Faecalibacterium* in the microbiota of the GI tract, wherein the method comprises administration of a composition, such as a food or pharmaceutical composition or a medical device, comprising a microbial lysozyme. In one embodiment, the microbial lysozyme is administered at a level of 8 to 250 ppm enzyme protein per kg composition. In an embodiment, the proportion of bacteria of genus *Faecalibacterium* is increased by at least 1%, such as at least 2%, at least 3%, at least 4%, at least 5%, at least 10%, at least 15% or at least 20%. In an alternative embodiment, the proportion of bacteria of genus *Faecalibacterium* is increased by a factor of at least 1.25, such as at least 1.50, at least 1.75, at least 2.0, at least 2.5 or at least 3.0.

In one embodiment, the method increases the proportion of bacteria of genus *Faecalibacterium* in the microbiota of the GI tract, wherein the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 12. In an embodiment, the proportion of bacteria of genus *Faecalibacterium* is increased by at least 1%, such as at least 2%, at least 3%, at least 4% or at least 5%. In an alternative embodiment, the proportion of bacteria of genus *Faecalibacterium* is increased by a factor of at least 1.25, such as at least 1.50, at least 1.75, at least 2.0, at least 2.5 or at least 3.0.

In a preferred embodiment, the invention relates to a method of preventing, alleviating or treating Irritable Bowel Syndrome (IBS) and/or Inflammatory Bowel Disease (IBD) comprising administering a composition such as e.g. a food or pharmaceutical composition or a medical device comprising one or more microbial lysozymes to a patient, wherein:

(a) the microbial lysozyme is a microbial lysozyme comprising one or more domains selected from the list consisting of GH24 and GH25; and (b) optionally the microbial lysozyme is administered on a daily basis for at least 5 days.

In another preferred embodiment, the invention relates to a method of preventing, alleviating or treating Irritable Bowel Syndrome (IBS) and/or Inflammatory Bowel Disease (IBD) comprising administering a composition such as e.g. a food or pharmaceutical composition or a medical device comprising one or more microbial lysozymes to a patient, wherein:

(a) the microbial lysozyme is a microbial lysozyme comprising one or more domains selected from the list consisting of GH24 and GH25; and (b) the microbial lysozyme is administered during a remission period (c) optionally the microbial lysozyme is administered on a daily basis for at least 5 days wherein the period of remission is a period in which the severity of IBS and/or IBD symptoms are temporarily diminished.

In yet another preferred embodiment, the invention relates to a method of increasing the proportion of bacteria of genus *Faecalibacterium* in the microbiome of the GI tract comprising administering a composition such as e.g. a food or pharmaceutical composition or a medical device comprising one or more microbial lysozymes, wherein:

(a) the microbial lysozyme is a GH24 lysozyme obtained or obtainable from the phylum Ascomycota, preferably the sub-phylum Pezizomycotina; and (b) the proportion of bacteria of genus *Faecalibacterium* in the microbiota of the GI tract of an animal is increased by at least 1%.

In another preferred embodiment, the invention relates to a method of increasing the proportion of bacteria of genus *Faecalibacterium* in the microbiome of the GI tract, comprising administering a composition such as e.g. a food or pharmaceutical composition or a medical device comprising one or more microbial lysozymes, wherein:

(a) the microbial lysozyme is a GH25 lysozyme obtained or obtainable from the phylum Ascomycota, preferably the sub-phylum Pezizomycotina;

(b) the proportion of bacteria of genus *Faecalibacterium* in the microbiota of the GI tract of an animal is increased by at least 1%.

In yet another preferred embodiment, the invention relates to a method of increasing the proportion of bacteria of genus *Faecalibacterium* in the microbiome of the GI tract comprising administering a composition such as e.g. a food or pharmaceutical composition or a medical device comprising one or more microbial lysozymes, wherein:

(a) the microbial lysozyme is a GH24 lysozyme obtained or obtainable from the phylum Ascomycota, preferably the sub-phylum Pezizomycotina;

(b) the proportion of bacteria of genus *Faecalibacterium* in the microbiota of the GI tract of an animal is increased by at least 1%; and (c) the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 12.

In yet another preferred embodiment, the invention relates to a method of increasing the proportion of bacteria of genus *Faecalibacterium* in the microbiome of the GI tract comprising administering a composition such as e.g. a food or pharmaceutical composition or a medical device comprising one or more microbial lysozymes, wherein:
(a) the microbial lysozyme is a GH25 lysozyme obtained or obtainable from the phylum Ascomycota, preferably the sub-phylum Pezizomycotina;
(b) the proportion of bacteria of genus *Faecalibacterium* in the microbiota of the GI tract of an animal is increased by at least 1%; and
(c) the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 12.

In one embodiment, the microbial lysozyme used in the invention is dosed at a level of 0.1 to 1000 ppm enzyme protein per kg food, such as 1 to 1000 ppm or 0.1 to 500 ppm, 1 to 500 ppm, 10 to 500 ppm, 10 to 300 ppm or 10 to 200 ppm enzyme protein per kg food, or any combination of these intervals. In one embodiment, the microbial lysozyme is dosed at a level of 11 to 125 ppm enzyme protein per kg food, such as 12 to 100 ppm, 13 to 75 ppm, 15 to 50 ppm, 17.5 to 40 ppm, 25 to 75 ppm or 30 to 60 ppm enzyme protein per kg food, or any combination of these intervals.

In one embodiment, the microbial lysozyme is of fungal origin. In an embodiment, the microbial lysozyme is obtained or obtainable from the phylum Ascomycota, such as the sub-phylum Pezizomycotina.

In one embodiment, the microbial lysozyme has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1.

In one embodiment, the microbial lysozyme comprises or consists of the amino acid sequence of SEQ ID NO: 1 or an allelic variant thereof; or is a fragment thereof having lysozyme activity, wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids. In another embodiment, the microbial lysozyme comprises or consists of the amino acid sequence of SEQ ID NO: 1 or an allelic variant thereof and a N-terminal and/or C-terminal His-tag and/or HQ-tag. In another aspect, the polypeptide comprises or consists of amino acids 1 to 208 of SEQ ID NO: 1.

In another embodiment, the microbial lysozyme is a variant of SEQ ID NO: 1 wherein the variant has lysozyme activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 1 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 1 is not more than 10, e.g., 1, 2, 3, 4, 5, 6, 7, 8, 9 or 10. In another embodiment, the number of substitutions, deletions, and/or insertions in SEQ ID NO: 1 is not more than 10, e.g., 1, 2, 3, 4, 5, 6, 7, 8, 9 or 10. In a further embodiment, the number of substitutions, preferably conservative substitutions, in SEQ ID NO: 1 is not more than 10, e.g., 1, 2, 3, 4, 5, 6, 7, 8, 9 or 10. In a further embodiment, the number of conservative substitutions in SEQ ID NO: 1 is not more than 10, e.g., 1, 2, 3, 4, 5, 6, 7, 8, 9 or 10.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a polyhistidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly. Other examples of conservative substitutions are G to A; A to G, S; V to I, L, A, T, S; I to V, L, M; L to I, M, V; M to L, I, V; P to A, S, N; F to Y, W, H; Y to F, W, H; W to Y, F, H; R to K, E, D; K to R, E, D; H to Q, N, S; D to N, E, K, R, Q; E to Q, D, K, R, N; S to T, A; T to S, V, A; C to S, T, A; N to D, Q, H, S; Q to E, N, H, K, R.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for lysozyme activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

The crystal structure of the *Acremonium alcalophilum* CBS114.92 lysozyme was solved at a resolution of 1.3 Å as disclosed in WO 2013/076253. These atomic coordinates can be used to generate a three dimensional model depicting the structure of the *Acremonium alcalophilum* CBS114.92 lysozyme or homologous structures (such as the variants of the present invention). Using the x/ray structure, amino acid residues D95 and E97 (using SEQ ID NO: 1 for numbering) were identified as catalytic residues.

In one embodiment, the microbial lysozyme has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4.

In one embodiment, the microbial lysozyme used in the invention comprises or consists of the amino acid sequence of SEQ ID NO: 4 or an allelic variant thereof; or is a fragment thereof having lysozyme activity, wherein the fragment comprises at least 210 amino acids, such as at least 215 amino acids, at least 220 amino acids, at least 225 amino acids, at least 230 amino acids, at least 235 amino acids or at least 240 amino acids. In another embodiment, the microbial lysozyme comprises or consists of the amino acid sequence of SEQ ID NO: 4 or an allelic variant thereof and a N-terminal and/or C-terminal His-tag and/or HQ-tag. In another aspect, the polypeptide comprises or consists of amino acids 1 to 245 of SEQ ID NO: 4.

In another embodiment, the microbial lysozyme is a variant of SEQ ID NO: 4 wherein the variant has lysozyme activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 4 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 4 is not more than 10, e.g., 1, 2, 3, 4, 5, 6, 7, 8, 9 or 10. In another embodiment, the number of substitutions, deletions, and/or insertions in SEQ ID NO: 4 is not more than 10, e.g., 1, 2, 3, 4, 5, 6, 7, 8, 9 or 10. In a further embodiment, the number of substitutions, preferably conservative substitutions, in SEQ ID NO: 4 is not more than 10, e.g., 1, 2, 3, 4, 5, 6, 7, 8, 9 or 10. In a further embodiment, the number of conservative substitutions in SEQ ID NO: 4 is not more than 10, e.g., 1, 2, 3, 4, 5, 6, 7, 8, 9 or 10.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a polyhistidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly. Other examples of conservative substitutions are G to A; A to G, S; V to I, L, A, T, S; I to V, L, M; L to I, M, V; M to L, I, V; P to A, S, N; F to Y, W, H; Y to F, W, H; W to Y, F, H; R to K, E, D; K to R, E, D; H to Q, N, S; D to N, E, K, R, Q; E to Q, D, K, R, N; S to T, A; T to S, V, A; C to S, T, A; N to D, Q, H, S; Q to E, N, H, K, R.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for lysozyme activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

The crystal structure of the Acremonium alcalophilum CBS114.92 lysozyme was solved at a resolution of 1.3 Å as disclosed in WO 2013/076253. These atomic coordinates can be used to generate a three dimensional model depicting the structure of the Acremonium alcalophilum CBS114.92 lysozyme or homologous structures (such as the variants of the present invention). Using the x/ray structure, amino acid residues D95 and E97 (using SEQ ID NO: 1 for numbering) were identified as catalytic residues.

In one embodiment, the polypeptides having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15.

In one embodiment, the polypeptides having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 18.

In one embodiment, the polypeptides having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 21.

In one embodiment, the polypeptides having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 24.

In one embodiment, the polypeptides having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 27.

In one embodiment, the polypeptides having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 30.

Examples of amino acid changes, conservative substitutions and N- and/or C-terminal linkers are described above.

The administration of probiotics, defined by the World Health Organization as "live organisms which when administered in adequate amounts confer a benefit on the host" is a safe nutrition intervention in the generally healthy population. Probiotics are found in the human intestinal tract and commonly present in yogurt and other dietetic and/or food items (e.g., beverages, cereals and chocolate candy bars).

Composition:

Compositions prepared in accordance with the invention may be administered in the form of foods or of dietary supplements and may be in any liquid, solid or semi-solid form. They may, for example, be dairy products, such as e.g. fermented dairy products comprising at least said microbial lysozyme, optionally combined with other bacteria, for example with yogurt ferments or cheese, or other food products such as a snack bar, chocolate, or beverages such as juice. Non-limiting examples of food compositions include full cream, skim, modified, flavoured milk, yoghurt including natural, flavoured, frozen or drinking yoghurt, tonics, and sports drinks, other dairy products such as custards, cheese and cottage cheese formulations and ice creams. Semi-solid food compositions may be selected from pastes and spreads. Solid compositions may include food bars, biscuits, cereals, food fibres, or any other food.

The microbial lysozyme can also be provided as a dietary supplement in the form of a powder, tablet, such as a lozenge or effervescent tablet, in capsular form, as a component of an emulsion or a paste, or in any other suitable carrier determined by those of skill in the art to be an effective carrier for live microorganisms. Compositions comprising a microbial lysozyme can be in individual sachets, capsules, chewing gum, or in more general compositions such as oil drops.

In one embodiment, the food composition is an end product, which is ready for consumption by a consumer. It thus can be bought, or obtained otherwise, by the consumer. However, the food composition may also be a basic component for the production of other foods.

The food composition as described herein may comprise a carrier. The term "carrier" suggests that the microbial lysozyme is distributed throughout the carrier and is known to the person skilled in the art. Carriers for use in the invention include without limitation e.g. natural flour, pre-dried flour, starch, modified starch, vegetable proteins, milk proteins, denatured proteins and sugar alcohols such as e.g. mannitol, sorbitol, inositol, dulcitol, xylitol or arabitol. Thus the carrier is the main component of the food composition. Preferably, the total amount of microbial lysozyme in the carrier is below 5% (w/w), more preferably below 2% (w/w) or below 0.5% (w/w), based on the combined amount of carrier and microbial lysozyme. In a specific embodiment, the food composition consists of the microbial lysozyme and the carrier. However, the composition may comprise additives. Preferably, such additives are also distributed throughout the carrier.

Preferred Embodiments

1. A method of preventing, alleviating or treating Irritable Bowel Syndrome (IBS) or Inflammatory Bowel Disease (IBD) comprising administering a microbial lysozyme or a composition comprising a microbial lysozyme.
2. The method of embodiment 1, wherein a composition comprising a lysozyme is administered at a level of 0.1 to 1000 ppm enzyme protein per kg composition.
3. The method of embodiment 1 or 2, wherein a composition comprising a lysozyme is administered at a level of 1 to 200 mg enzyme protein per kg bodyweight, such as between between 1 to 150 mg, 2 to 100 mg, 2 to 90 mg, 2 to 80 mg or 10 to 70 mg enzyme protein per kg bodyweight.
4. The method of any one of embodiments 1 to 3, wherein a composition comprising a lysozyme is administered at a level of 0.04 to 11.0 µmol enzyme protein per kg bodyweight, such as between 0.1 to 6.0 µmol, 0.2 to 5.0 µmol, 0.3 to 4.0 µmol or 0.4 to 3.0 µmol enzyme protein per kg bodyweight.
5. The method of any one of embodiments 1 to 4, wherein the microbial lysozyme is obtained or obtainable from the kingdom Fungi.
6. The method of any one of embodiments 1 to 5, wherein the microbial lysozyme stabilizes the healthy microbiota in the GI tract and suppresses growth and/or intestinal colonization of bacterial pathogens.
7. The method of any one of embodiments 1 to 6, wherein the microbial lysozyme prevents, alleviates or treats inflammation.
8. The method of any one of embodiments 1 to 7, wherein the microbial lysozyme prevents, alleviates or treats inflammation in the GI tract.
9. The method of any one of embodiments 1 to 7, wherein the microbial lysozyme prevents, alleviates or treats inflammation in the upper GI tract.
10. The method of any one of embodiments 1 to 7, wherein the microbial lysozyme prevents, alleviates or treats inflammation in the lower GI tract.
11. The method of any one of embodiments 1 to 10, wherein the microbial lysozyme maintains remission of IBS and/or IBD.
12. The method of any one of embodiments 1 to 11, wherein the microbial lysozyme prevents, alleviates or treats post-surgery flare up.
13. The method of any one of embodiments 1 to 12, wherein the microbial lysozyme reduces ectopic lipid deposition associated with obesity such as e.g. diet induced obesity.
14. The method of embodiment 13, wherein the microbial lysozyme is a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1.
15. The method of any one of embodiments 1 to 14, wherein the microbial lysozyme improves glucose dysregulation associated with obesity such as e.g. diet induced obesity.
16. The method of embodiment 15, wherein the microbial lysozyme is a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1.
17. The method of any one of embodiments 1 to 16, wherein the composition increases the proportion of bacteria of genus *Faecalibacterium* in the microbiota of the GI tract 18. The method of embodiment 17, wherein the proportion of bacteria of genus *Faecalibacterium* is increased by at least 1%, such as at least 2%, at least 3%, at least 4%, at least 5%, at least 10%, at least 15% or at least 20%.

19. The method of embodiment 17, wherein the proportion of bacteria of genus *Faecalibacterium* is increased by a factor of at least 1.25, such as at least 1.50, at least 1.75, at least 2.0, at least 2.5 or at least 3.0.

20. The method of any one of embodiments 1 to 19, wherein the microbial lysozyme is obtained or obtainable from the phylum Ascomycota.

21. The method of any one of embodiments 1 to 19, wherein the microbial lysozyme is obtained or obtainable from the subphylum Pezizomycotina.

22. The method of any one of embodiments 1 to 21, wherein the microbial lysozyme comprises one or more domains selected from the list consisting of GH24 and GH25.

23. The method of any one of embodiments 1 to 21, wherein the microbial lysozyme comprises one or more domains from GH24.

24. The method of any one of embodiments 1 to 21, wherein the microbial lysozyme comprises one or more domains from GH25.

25. The method of any one of embodiments 1 to 24, wherein the microbial lysozyme is selected from the group consisting of:
   (a) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;
   (b) a variant of SEQ ID NO: 1 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
   (c) a fragment of the polypeptide of (a) or (b) that has lysozyme activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids;
   (d) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4;
   (e) a variant of SEQ ID NO: 4 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
   (f) a fragment of the polypeptide of (d) or (e) that has lysozyme activity wherein the fragment comprises at least 210 amino acids, such as at least 215 amino acids, at least 220 amino acids, at least 225 amino acids, at least 230 amino acids, at least 235 amino acids or at least 240 amino acids;
   (g) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15;
   (h) a variant of SEQ ID NO: 15 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and
   (i) a fragment of the polypeptide of (g) or (h) that has lysozyme activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids.

26. The method of any one of embodiments 1 to 24, wherein the microbial lysozyme is selected from the group consisting of:
   (a) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;
   (b) a variant of SEQ ID NO: 1 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
   (c) a fragment of the polypeptide of (a) or (b) that has lysozyme activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids;
   (d) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15;
   (e) a variant of SEQ ID NO: 15 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and
   (f) a fragment of the polypeptide of (d) or (e) that has lysozyme activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids.

27. The method of any one of embodiments 1 to 25, wherein the microbial lysozyme is selected from the group consisting of amino acids 1 to 208 of SEQ ID NO: 1, amino acids 1 to 245 of SEQ ID NO: 4 and amino acids 1 to 207 of SEQ ID NO: 15.

28. The method of any one of embodiments 1 to 26, wherein the microbial lysozyme is selected from the group consisting of amino acids 1 to 208 of SEQ ID NO: 1 and amino acids 1 to 207 of SEQ ID NO: 15.

29. The method of any one of embodiments 1 to 28 for use in the treatment of a human.

30. The method of any one of embodiments 1 to 29, wherein the composition is a liquid formulation.

31. The method of any one of embodiments 1 to 29, wherein the composition is a solid formulation.

32. The method of any one of embodiments 1 to 31, wherein the composition is a food or pharmaceutical composition or a medical device.

33. The method of any one of embodiments 1 to 32, wherein the composition is a food composition.

34. The method of any one of embodiments 1 to 32, wherein the composition is a pharmaceutical composition.

35. The method of any one of embodiments 1 to 32, wherein the composition is a medical device.

36. The method of any one of embodiments 1 to 35, wherein the composition is in the form of a powder, tablet, lozenge, effervescent tablet, capsule, emulsion, paste, individual sachet, chewing gum or oil drops.

37. The method of any one of embodiments 1 to 36, wherein the composition is administered by means of oral or rectal administration, to the extent possible.

38. A method of improving the intestinal health in humans comprising reducing the amount of dead *Lactobacillus johnsonii* cells in the digestive tract, comprising providing to said human an isolated GH25 polypeptide having lysozyme activity against *Lactobacillus johnsonii* as determined by Method for the Determination of Lysozyme Activity Against *Lactobacillus johnsonii*.

39. A method of improving the intestinal health in humans comprising reducing the amount of dead *Lactobacillus johnsonii* cells in the digestive tract, comprising providing to said human a polypeptide selected from the group consisting of a polpeptide having at least 90% sequence identity to the polypeptide of SEQ ID NO: 1, a polypeptide having at least 90% sequence identity to the polypeptide of SEQ ID NO: 15, a polypeptide having at least 90% sequence identity to the polypeptide of SEQ ID NO: 18, a polpypeptide having at least 90% sequence identity to the polypeptide of SEQ ID NO: 21, a polpypeptide having at least 90% sequence identity to the polypeptide of SEQ ID NO: 24, a polpypeptide having at least 90% sequence identity to the polypeptide of SEQ ID NO: 27, and a polpypeptide having at least 90% sequence identity to the polypeptide of SEQ ID NO: 30, preferably selected from the group consisting of a polpypeptide having at least 90% sequence identity to the polypeptide of SEQ ID NO: 1, a polypeptide having at least 90% sequence identity to the polypeptide of SEQ ID NO: 15, a polpypeptide having at least 90% sequence identity to the polypeptide of SEQ ID NO: 18, a polypeptide having at least 90% sequence identity to the polypeptide of SEQ ID NO: 21, a polpypeptide having at least 90% sequence identity to the polypeptide of SEQ ID NO: 27, and a polpypeptide having at least 90% sequence identity to the polypeptide of SEQ ID NO: 30, more preferably selected from the group consisting of a polpypeptide having at least 90% sequence identity to the polypeptide of SEQ ID NO: 18, a polpypeptide having at least 90% sequence identity to the polypeptide of SEQ ID NO: 21, a polpypeptide having at least 90% sequence identity to the polypeptide of SEQ ID NO: 27, and a polpypeptide having at least 90% sequence identity to the polypeptide of SEQ ID NO: 30, even more preferably a polpypeptide having at least 90% sequence identity to the polypeptide of SEQ ID NO: 21 or a polpypeptide having at least 90% sequence identity to the polypeptide of SEQ ID NO: 27.

40. A method of improving the intestinal health in humans comprising reducing the amount of dead *Lactobacillus johnsonii* cells, or cell wall debris therefrom, in the digestive tract, comprising providing to said human a polypeptide selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO: 1.

41. A method of improving the intestinal health in humans comprising reducing the amount of dead *Lactobacillus johnsonii* cells, or cell wall debris therefrom, in the digestive tract, comprising providing to said human a polypeptide selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO: 21.

42. A method of improving the intestinal health in humans comprising reducing the amount of dead *Lactobacillus johnsonii* cells, or cell wall debris therefrom, in the digestive tract, comprising providing to said human a polypeptide selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO: 27.

43. A method of promoting the elimination of dead *Lactobacillus johnsonii* cells, or cell wall debris therefrom, from the digestive tract of humans, comprising providing to said human an isolated GH25 polypeptide having lysozyme activity against *Lactobacillus johnsonii* as determined by Method for the Determination of Lysozyme Activity Against *Lactobacillus johnsonii*.

44. A method of promoting the elimination of dead *Lactobacillus johnsonii* cells, or cell wall debris therefrom, from the digestive tract of humans comprising providing to said humans a source of a polypeptide selected from the group consisting of a polypeptide having at least 90% sequence identity to the polypeptide of SEQ ID NO: 1, a polypeptide having at least 90% sequence identity to the polypeptide of SEQ ID NO: 15, a polypeptide having at least 90% sequence identity to the polypeptide of SEQ ID NO: 18, a polpypeptide having at least 90% sequence identity to the polypeptide of SEQ ID NO: 21, a polpypeptide having at least 90% sequence identity to the polypeptide of SEQ ID NO: 24, a polpypeptide having at least 90% sequence identity to the polypeptide of SEQ ID NO: 27, and a polpypeptide having at least 90% sequence identity to the polypeptide of SEQ ID NO: 30, preferably selected from the group consisting of a polypeptide having at least 90% sequence identity to the polypeptide of SEQ ID NO: 1, a polypeptide having at least 90% sequence identity to the polypeptide of SEQ ID NO: 15, a polypeptide having at least 90% sequence identity to the polypeptide of SEQ ID NO: 18, a polypeptide having at least 90% sequence identity to the polypeptide of SEQ ID NO: 21, a polpypeptide having at least 90% sequence identity to the polypeptide of SEQ ID NO: 27, and a polpypeptide having at least 90% sequence identity to the polypeptide of SEQ ID NO: 30, more preferably selected from the group consisting of a polpypeptide having at least 90% sequence identity to the polypeptide of SEQ ID NO: 18, a polpypeptide having at least 90% sequence identity to the polypeptide of SEQ ID NO: 21, a polpypeptide having at least 90% sequence identity to the polypeptide of SEQ ID NO: 27, and a polpypeptide having at least 90% sequence identity to the polypeptide of SEQ ID NO: 30, even more preferably a polpypeptide having at least 90% sequence identity to the polypeptide of SEQ ID NO: 21 or a polpypeptide having at least 90% sequence identity to the polypeptide of SEQ ID NO: 27.

45. A method of promoting the elimination of dead *Lactobacillus johnsonii* cells, or cell wall debris therefrom, from the digestive tract of humans comprising providing to said humans a source of a polypeptide selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO: 1.

46. A method of promoting the elimination of dead *Lactobacillus johnsonii* cells, or cell wall debris therefrom, from the digestive tract of humans comprising providing to said humans a source of a polypeptide selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO: 21.

47. A method of promoting the elimination of dead *Lactobacillus johnsonii* cells, or cell wall debris therefrom, from the digestive tract of humans comprising providing to said humans a source of a polypeptide selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO: 27.

48. The method of any one of embodiments 38 to 47 wherein the polypetide has a lysozyme activity against *Lactobacillus johnsonii* at 5 ppm that increases optical density (OD) measurement at 405 nm of at least 0.20 as determined by Method for the Determination of Lysozyme Activity Against *Lactobacillus johnsonii*.

49. The method of any one of embodiments 38 to 48, wherein the polypeptides having lysozyme activity prevents, alleviates or treats inflammation.

50. The method of any one of embodiments 38 to 48, wherein the polypeptides having lysozyme activity prevents, alleviate and treats inflammation in the GI tract.

51. The method of any one of embodiments 38 to 48, wherein the polypeptides having lysozyme activity prevents, alleviate and treats inflammation in the upper GI tract.

52. The method of any one of embodiments 38 to 48, wherein the polypeptides having lysozyme activity prevents, alleviate and treats inflammation in the lower GI tract.

53. A method of increasing the proportion of bacteria of genus *Faecalibacterium* in the microbiome of the GI tract comprising administering a microbial lysozyme or a composition comprising a microbial lysozyme to a patient.

54. The method of embodiment 53, wherein a composition comprising a lysozyme is administered at a level of 0.1 to 1000 ppm enzyme protein per kg composition.

55. The method of embodiment 53 or 54, wherein a composition comprising a lysozyme is administered at a level of 1 to 200 mg enzyme protein per kg bodyweight, such as between 1 to 150 mg, 2 to 100 mg, 2 to 90 mg, 2 to 80 mg or 10 to 70 mg enzyme protein per kg bodyweight.

56. The method of any one of embodiments 53 to 55, wherein a composition comprising a lysozyme is administered at a level of 0.04 to 11.0 μmol enzyme protein per kg bodyweight, such as between 0.1 to 6.0 μmol, 0.2 to 5.0 μmol, 0.3 to 4.0 μmol or 0.4 to 3.0 μmol enzyme protein per kg bodyweight.

57. The method of nay one of embodiments 53 to 56, wherein the microbial lysozyme is obtained or obtainable from the kingdom Fungi.

58. The method of any one of embodiments 53 to 57, wherein the microbial lysozyme stabilizes the healthy microbiota in the GI tract and suppresses growth and/or intestinal colonization of bacterial pathogens.

59. The method of any one of embodiments 53 to 58, wherein the microbial lysozyme prevents, alleviates or treats inflammation.

60. The method of any one of embodiments 53 to 58, wherein the microbial lysozyme prevents, alleviates or treats inflammation in the GI tract.

61. The method of any one of embodiments 53 to 58, wherein the microbial lysozyme prevents, alleviates or treats inflammation in the upper GI tract.

62. The method of any one of embodiments 53 to 58, wherein the microbial lysozyme prevents, alleviates or treats inflammation in the lower GI tract.

63. The method of any one of embodiments 53 to 62, wherein the microbial lysozyme maintains remission of IBS and/or IBD.

64. The method of any one of embodiments 53 to 63, wherein the microbial lysozyme prevents, alleviates or treats post-surgery flare up.

65. The method of any one of embodiments 53 to 64, wherein the microbial lysozyme reduces ectopic lipid deposition associated with obesity such as e.g. diet induced obesity.

66. The method of any one of embodiments 53 to 65, wherein the proportion of bacteria of genus *Faecalibacterium* is increased by a factor of at least 1.25, such as at least 1.50, at least 1.75, at least 2.0, at least 2.5 or at least 3.0.

67. The method of any one of embodiments 53 to 66, wherein the microbial lysozyme is obtained or obtainable from the phylum Ascomycota.

68. The method of any one of embodiments 53 to 66, wherein the microbial lysozyme is obtained or obtainable from the subphylum Pezizomycotina.

69. The method of any one of embodiments 53 to 68, wherein the microbial lysozyme comprises one or more domains selected from the list consisting of GH24 and GH25.

70. The method of any one of embodiments 53 to 68, wherein the microbial lysozyme comprises one or more domains from GH24.

71. The method of any one of embodiments 53 to 68, wherein the microbial lysozyme comprises one or more domains from GH25.

72. The method of any one of embodiments 53 to 71, wherein the microbial lysozyme is selected from the group consisting of:
   (a) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;
(b) a variant of SEQ ID NO: 1 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(c) a fragment of the polypeptide of (a) or (b) that has lysozyme activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids;
(d) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4;
(e) a variant of SEQ ID NO: 4 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(f) a fragment of the polypeptide of (d) or (e) that has lysozyme activity wherein the fragment comprises at least 210 amino acids, such as at least 215 amino acids, at least 220 amino acids, at least 225 amino acids, at least 230 amino acids, at least 235 amino acids or at least 240 amino acids;
(g) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15;
(h) a variant of SEQ ID NO: 15 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and
(i) a fragment of the polypeptide of (g) or (h) that has lysozyme activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids.

73. The method of any one of embodiments 53 to 71, wherein the microbial lysozyme is selected from the group consisting of:
(a) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;
(b) a variant of SEQ ID NO: 1 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(c) a fragment of the polypeptide of (a) or (b) that has lysozyme activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids;
(d) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15;
(e) a variant of SEQ ID NO: 15 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and
(f) a fragment of the polypeptide of (d) or (e) that has lysozyme activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids.

74. The method of any one of embodiments 53 to 72, wherein the microbial lysozyme is selected from the group consisting of amino acids 1 to 208 of SEQ ID NO: 1, amino acids 1 to 245 of SEQ ID NO: 4 and amino acids 1 to 207 of SEQ ID NO: 15.

75. The method of any one of embodiments 53 to 73, wherein the microbial lysozyme is selected from the group consisting of amino acids 1 to 208 of SEQ ID NO: 1 and amino acids 1 to 207 of SEQ ID NO: 15.

76. The method of any one of embodiments 53 to 75 for use in the treatment of a human.

77. The method of any one of embodiments 53 to 76, wherein the composition is a liquid formulation.

78. The method of any one of embodiments 53 to 76, wherein the composition is a solid formulation.

79. The method of any one of embodiments 53 to 78, wherein the composition is a food or pharmaceutical composition or a medical device.

80. The method of any one of embodiments 53 to 79, wherein the composition is a food composition.

81. The method of any one of embodiments 53 to 79, wherein the composition is a pharmaceutical composition.

82. The method of any one of embodiments 53 to 79, wherein the composition is a medical device.

83. The method of any one of embodiments 53 to 82, wherein the composition is in the form of a powder, tablet, lozenge, effervescent tablet, capsule, emulsion, paste, individual sachet, chewing gum or oil drops.

84. The method of any one of embodiments 53 to 83, wherein the composition is administered by means of oral or rectal administration, to the extent possible.

85. The method of any one of embodiments 1 to 84, wherein the method is used in the treatment of Crohn's disease and/or Ulcerative colitis.

86. Use of a microbial lysozyme or a composition comprising microbial lysozyme in the manufacture of a medicament for preventing, alleviating or treating Irritable Bowel Syndrome (IBS) or Inflammatory Bowel Disease (IBD).

87. The use of embodiment 86, wherein a composition comprising a lysozyme is administered at a level of 0.1 to 1000 ppm enzyme protein per kg composition.

88. The use of embodiment 86 or 87, wherein a composition comprising a lysozyme is administered at a level of 1 to 200 mg enzyme protein per kg bodyweight, such as between between 1 to 150 mg, 2 to 100 mg, 2 to 90 mg, 2 to 80 mg or 10 to 70 mg enzyme protein per kg bodyweight.

89. The use of any one of embodiments 86 to 88, wherein a composition comprising a lysozyme is administered at a level of 0.04 to 11.0 µmol enzyme protein per kg bodyweight, such as between 0.1 to 6.0 µmol, 0.2 to 5.0 µmol, 0.3 to 4.0 µmol or 0.4 to 3.0 µmol enzyme protein per kg bodyweight.

90. The use of any one of embodiments 86 to 89, wherein the microbial lysozyme is obtained or obtainable from the kingdom Fungi.

91. The use of any one of embodiments 86 to 90 wherein the microbial lysozyme stabilizes the healthy microbiota in the GI tract and suppresses growth and/or intestinal colonization of bacterial pathogens.

92. The use of any one of embodiments 86 to 91, wherein the microbial lysozyme prevents, alleviates or treats inflammation.

93. The use of any one of embodiments 86 to 92, wherein the microbial lysozyme prevents, alleviates or treats inflammation in the GI tract.

94. The use of any one of embodiments 86 to 92, wherein the microbial lysozyme prevents, alleviates or treats inflammation in the upper GI tract.

95. The use of any one of embodiments 86 to 92, wherein the microbial lysozyme prevents, alleviates or treats inflammation in the lower GI tract.

96. The use of any one of embodiments 86 to 95, wherein the microbial lysozyme maintains remission of IBS and/or IBD.

97. The use of any one of embodiments 86 to 96, wherein the microbial lysozyme prevents, alleviates or treats post-surgery flare up.

98. The use of any one of embodiments 86 to 97, wherein the microbial lysozyme reduces ectopic lipid deposition associated with obesity such as e.g. diet induced obesity.

99. The use of any one of embodiments 86 to 98, wherein the composition increases the proportion of bacteria of genus *Faecalibacterium* in the microbiota of the GI tract.

100. The use of embodiment 99, wherein the proportion of bacteria of genus *Faecalibacterium* is increased by at least 1%, such as at least 2%, at least 3%, at least 4%, at least 5%, at least 10%, at least 15% or at least 20%.

101. The use of embodiment 99, wherein the proportion of bacteria of genus *Faecalibacterium* is increased by a factor of at least 1.25, such as at least 1.50, at least 1.75, at least 2.0, at least 2.5 or at least 3.0.

102. The use of any one of embodiments 86 to 101, wherein the microbial lysozyme is obtained or obtainable from the phylum Ascomycota.

103. The use of any one of embodiments 86 to 101, wherein the microbial lysozyme is obtained or obtainable from the subphylum Pezizomycotina.

104. The use of any one of embodiments 86 to 103, wherein the microbial lysozyme comprises one or more domains selected from the list consisting of GH24 and GH25.

105. The use of any one of embodiments 86 to 103, wherein the microbial lysozyme comprises one or more domains from GH24.

106. The use of any one of embodiments 86 to 103, wherein the microbial lysozyme comprises one or more domains from GH25.

107. The use of any one of embodiments 86 to 106, wherein the microbial lysozyme is selected from the group consisting of:
(a) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;
(b) a variant of SEQ ID NO: 1 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(c) a fragment of the polypeptide of (a) or (b) that has lysozyme activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids;
(d) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4;
(e) a variant of SEQ ID NO: 4 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(f) a fragment of the polypeptide of (d) or (e) that has lysozyme activity wherein the fragment comprises at least 210 amino acids, such as at least 215 amino acids, at least 220 amino acids, at least 225 amino acids, at least 230 amino acids, at least 235 amino acids or at least 240 amino acids;
(g) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15;
(h) a variant of SEQ ID NO: 15 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and
(i) a fragment of the polypeptide of (g) or (h) that has lysozyme activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids.

108. The use of any one of embodiments 86 to 106, wherein the microbial lysozyme is selected from the group consisting of:
(a) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;
(b) a variant of SEQ ID NO: 1 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(c) a fragment of the polypeptide of (a) or (b) that has lysozyme activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids;
(d) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15;
(e) a variant of SEQ ID NO: 15 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and
(f) a fragment of the polypeptide of (d) or (e) that has lysozyme activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids.

109. The use of any one of embodiments 86 to 107, wherein the microbial lysozyme is selected from the group consisting of amino acids 1 to 208 of SEQ ID NO: 1, amino acids 1 to 245 of SEQ ID NO: 4 and amino acids 1 to 207 of SEQ ID NO: 15.

110. The use of any one of embodiments 86 to 108, wherein the microbial lysozyme is selected from the group consisting of amino acids 1 to 208 of SEQ ID NO: 1 and amino acids 1 to 207 of SEQ ID NO: 15.

111. The use of any one of embodiments 86 to 110 for use in the treatment of a human.

112. The use of any one of embodiments 86 to 111, wherein the composition is a liquid formulation.

113. The use of any one of embodiments 86 to 111, wherein the composition is a solid formulation.

114. The use of any one of embodiments 86 to 113, wherein the composition is a food or pharmaceutical composition or a medical device.

115. The use of any one of embodiments 86 to 114, wherein the composition is a food composition.

116. The use of any one of embodiments 86 to 114, wherein the composition is a pharmaceutical composition.

117. The use of any one of embodiments 86 to 114, wherein the composition is a medical device.

118. The use of any one of embodiments 86 to 117, wherein the composition is in the form of a powder, tablet, lozenge, effervescent tablet, capsule, emulsion, paste, individual sachet, chewing gum or oil drops.

119. The use of any one of embodiments 86 to 118, wherein the composition is administered by means of oral or rectal administration, to the extent possible.

120. Use of a microbial lysozyme or a composition comprising microbial lysozyme in the manufacture of a medicament for increasing the proportion of bacteria of genus *Faecalibacterium* in the microbiome of the GI tract.

121. The use of embodiment 120, wherein a composition comprising a lysozyme is administered at a level of 0.1 to 1000 ppm enzyme protein per kg composition.

122. The use of embodiment 120 or 121, wherein a composition comprising a lysozyme is administered at a level of 1 to 200 mg enzyme protein per kg bodyweight, such as between between 1 to 150 mg, 2 to 100 mg, 2 to 90 mg, 2 to 80 mg or 10 to 70 mg enzyme protein per kg bodyweight.

123. The use of any one of embodiments 120 to 122, wherein a composition comprising a lysozyme is administered at a level of 0.04 to 11.0 µmol enzyme protein per kg bodyweight, such as between 0.1 to 6.0 µmol, 0.2 to 5.0 µmol, 0.3 to 4.0 µmol or 0.4 to 3.0 µmol enzyme protein per kg bodyweight.

124. The use of any one of embodiments 120 to 123, wherein the microbial lysozyme is obtained or obtainable from the kingdom Fungi.

125. The use of any one of embodiments 120 to 124, wherein the microbial lysozyme stabilizes the healthy microbiota in the GI tract and suppresses growth and/or intestinal colonization of bacterial pathogens.

126. The use of any one of embodiments 120 to 125, wherein the microbial lysozyme prevents, alleviates or treats inflammation.

127. The use of any one of embodiments 120 to 126, wherein the microbial lysozyme prevents, alleviates or treats inflammation in the GI tract.

128. The use of any one of embodiments 120 to 126, wherein the microbial lysozyme prevents, alleviates or treats inflammation in the upper GI tract.

129. The use of any one of embodiments 120 to 126, wherein the microbial lysozyme prevents, alleviates or treats inflammation in the lower GI tract.

130. The use of any one of embodiments 120 to 129, wherein the microbial lysozyme maintains remission of IBS and/or IBD.

131. The use of any one of embodiments 120 to 130, wherein the microbial lysozyme prevents, alleviates or treats post-surgery flare up.

132. The use of any one of embodiments 120 to 131, wherein the microbial lysozyme reduces ectopic lipid deposition associated with obesity such as e.g. diet induced obesity.

133. The use of any one of embodiments 120 to 132, wherein the proportion of bacteria of genus *Faecalibacterium* is increased by at least 1%, such as at least 2%, at least 3%, at least 4%, at least 5%, at least 10%, at least 15% or at least 20%.

134. The use of any one of embodiments 120 to 132, wherein the proportion of bacteria of genus *Faecalibacterium* is increased by a factor of at least 1.25, such as at least 1.50, at least 1.75, at least 2.0, at least 2.5 or at least 3.0.

135. The use of any one of embodiments 120 to 134, wherein the microbial lysozyme is obtained or obtainable from the phylum Ascomycota.

136. The use of any one of embodiments 120 to 135, wherein the microbial lysozyme is obtained or obtainable from the subphylum Pezizomycotina.

137. The use of any one of embodiments 120 to 136, wherein the microbial lysozyme comprises one or more domains selected from the list consisting of GH24 and GH25.

138. The use of any one of embodiments 120 to 136, wherein the microbial lysozyme comprises one or more domains from GH24.

139. The use of any one of embodiments 120 to 136, wherein the microbial lysozyme comprises one or more domains from GH25.

140. The use of any one of embodiments 120 to 139, wherein the microbial lysozyme is selected from the group consisting of:
  (a) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;
  (b) a variant of SEQ ID NO: 1 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
  (c) a fragment of the polypeptide of (a) or (b) that has lysozyme activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids;
  (d) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4;
  (e) a variant of SEQ ID NO: 4 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
  (f) a fragment of the polypeptide of (d) or (e) that has lysozyme activity wherein the fragment comprises at least 210 amino acids, such as at least 215 amino acids, at least 220 amino acids, at least 225 amino acids, at least 230 amino acids, at least 235 amino acids or at least 240 amino acids;
  (g) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15;
  (h) a variant of SEQ ID NO: 15 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and
  (i) a fragment of the polypeptide of (g) or (h) that has lysozyme activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids.

141. The use of any one of embodiments 120 to 139, wherein the microbial lysozyme is selected from the group consisting of:
  (a) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;
  (b) a variant of SEQ ID NO: 1 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
  (c) a fragment of the polypeptide of (a) or (b) that has lysozyme activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids;
  (d) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15;
  (e) a variant of SEQ ID NO: 15 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and
  (f) a fragment of the polypeptide of (d) or (e) that has lysozyme activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids.

142. The use of any one of embodiments 120 to 140, wherein the microbial lysozyme is selected from the group consisting of amino acids 1 to 208 of SEQ ID NO: 1, amino acids 1 to 245 of SEQ ID NO: 4 and amino acids 1 to 207 of SEQ ID NO: 15.

143. The use of any one of embodiments 120 to 141, wherein the microbial lysozyme is selected from the group consisting of amino acids 1 to 208 of SEQ ID NO: 1 and amino acids 1 to 207 of SEQ ID NO: 15.

144. The use of any one of embodiments 120 to 143 for use in the treatment of a human.

145. The use of any one of embodiments 120 to 144, wherein the composition is a liquid formulation.

146. The use of any one of embodiments 120 to 144, wherein the composition is a solid formulation.

147. The use of any one of embodiments 120 to 146, wherein the composition is a food or pharmaceutical composition or a medical device.

148. The use of any one of embodiments 120 to 147, wherein the composition is a food composition.

149. The use of any one of embodiments 120 to 147, wherein the composition is a pharmaceutical composition.

150. The use of any one of embodiments 120 to 147, wherein the composition is a medical device.

151. The use of any one of embodiments 120 to 150, wherein the composition is in the form of a powder, tablet, lozenge, effervescent tablet, capsule, emulsion, paste, individual sachet, chewing gum or oil drops.

152. The use of any one of embodiments 120 to 151, wherein the composition is administered by means of oral or rectal administration, to the extent possible.

153. The use of any one of embodiments 86 to 152, wherein the use is used in the treatment of Crohn's disease and/or Ulcerative colitis.

154. Microbial lysozyme or a composition comprising microbial lysozyme for use in a method of preventing, alleviating or treating Irritable Bowel Syndrome (IBS) or Inflammatory Bowel Disease (IBD).

155. The microbial lysozyme or composition comprising such of embodiment 154, wherein a composition comprising a lysozyme is administered at a level of 0.1 to 1000 ppm enzyme protein per kg composition.

156. The microbial lysozyme or composition comprising such of embodiment 154 or 155, wherein a composition comprising a lysozyme is administered at a level of 1 to 200 mg enzyme protein per kg bodyweight, such as between between 1 to 150 mg, 2 to 100 mg, 2 to 90 mg, 2 to 80 mg or 10 to 70 mg enzyme protein per kg bodyweight.

157. The microbial lysozyme or composition comprising such of any one of embodiments 154 to 156, wherein a composition comprising a lysozyme is administered at a level of 0.04 to 11.0 µmol enzyme protein per kg bodyweight, such as between 0.1 to 6.0 µmol, 0.2 to 5.0 µmol, 0.3 to 4.0 µmol or 0.4 to 3.0 µmol enzyme protein per kg bodyweight.

158. The microbial lysozyme or composition comprising such of any one of embodiments 154 to 157, wherein the microbial lysozyme is obtained or obtainable from the kingdom Fungi.

159. The microbial lysozyme or composition comprising such of any one of embodiments 154 to 158, wherein the microbial lysozyme stabilizes the healthy microbiota in the GI tract and suppresses growth and/or intestinal colonization of bacterial pathogens.

160. The microbial lysozyme or composition comprising such of any one of embodiments 154 to 159, wherein the microbial lysozyme prevents, alleviates or treats inflammation.

161. The microbial lysozyme or composition comprising such of any one of embodiments 154 to 160, wherein the microbial lysozyme prevents, alleviates or treats inflammation in the GI tract.

162. The microbial lysozyme or composition comprising such of any one of embodiments 154 to 160, wherein the microbial lysozyme prevents, alleviates or treats inflammation in the upper GI tract.

163. The microbial lysozyme or composition comprising such of any one of embodiments 154 to 160, wherein the microbial lysozyme prevents, alleviates or treats inflammation in the lower GI tract.

164. The microbial lysozyme or composition comprising such of any one of embodiments 154 to 163, wherein the microbial lysozyme maintains remission of IBS and/or IBD.

165. The microbial lysozyme or composition comprising such of any one of embodiments 154 to 164, wherein the microbial lysozyme prevents, alleviates or treats post-surgery flare up.

166. The microbial lysozyme or composition comprising such of any one of embodiments 154 to 165, wherein the microbial lysozyme reduces ectopic lipid deposition associated with obesity such as e.g. diet induced obesity.

167. The microbial lysozyme or composition comprising such of any one of embodiments 154 to 166, wherein the composition increases the proportion of bacteria of genus *Faecalibacterium* in the microbiota of the GI tract.

168. The microbial lysozyme or composition comprising such of embodiment 167, wherein the proportion of bacteria of genus *Faecalibacterium* is increased by at least 1%, such as at least 2%, at least 3%, at least 4%, at least 5%, at least 10%, at least 15% or at least 20%.

169. The microbial lysozyme or composition comprising such of embodiment 167, wherein the proportion of bacteria of genus *Faecalibacterium* is increased by a factor of at least 1.25, such as at least 1.50, at least 1.75, at least 2.0, at least 2.5 or at least 3.0.

170. The microbial lysozyme or composition comprising such of any one of embodiments 154 to 169, wherein the microbial lysozyme is obtained or obtainable from the phylum Ascomycota.

171. The microbial lysozyme or composition comprising such of any one of embodiments 154 to 169, wherein the microbial lysozyme is obtained or obtainable from the subphylum Pezizomycotina.

172. The microbial lysozyme or composition comprising such of any one of embodiments 154 to 171, wherein the microbial lysozyme comprises one or more domains selected from the list consisting of GH24 and GH25.

173. The microbial lysozyme or composition comprising such of any one of embodiments 154 to 172, wherein the microbial lysozyme comprises one or more domains from GH24.

174. The microbial lysozyme or composition comprising such of any one of embodiments 154 to 172, wherein the microbial lysozyme comprises one or more domains from GH25.

175. The microbial lysozyme or composition comprising such of any one of embodiments 154 to 174, wherein the microbial lysozyme is selected from the group consisting of:
(a) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;
(b) a variant of SEQ ID NO: 1 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(c) a fragment of the polypeptide of (a) or (b) that has lysozyme activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids;
(d) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4;
(e) a variant of SEQ ID NO: 4 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(f) a fragment of the polypeptide of (d) or (e) that has lysozyme activity wherein the fragment comprises at least 210 amino acids, such as at least 215 amino acids, at least 220 amino acids, at least 225 amino acids, at least 230 amino acids, at least 235 amino acids or at least 240 amino acids;
(g) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15;
(h) a variant of SEQ ID NO: 15 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and
(i) a fragment of the polypeptide of (g) or (h) that has lysozyme activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids.
176. The microbial lysozyme or composition comprising such of any one of embodiments 154 to 174, wherein the microbial lysozyme is selected from the group consisting of:
(a) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;
(b) a variant of SEQ ID NO: 1 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(c) a fragment of the polypeptide of (a) or (b) that has lysozyme activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids;
(d) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15;
(e) a variant of SEQ ID NO: 15 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and
(f) a fragment of the polypeptide of (d) or (e) that has lysozyme activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids.
177. The microbial lysozyme or composition comprising such of any one of embodiments 154 to 175, wherein the microbial lysozyme is selected from the group consisting of amino acids 1 to 208 of SEQ ID NO: 1, amino acids 1 to 245 of SEQ ID NO: 4 and amino acids 1 to 207 of SEQ ID NO: 15.
178. The microbial lysozyme or composition comprising such of any one of embodiments 154 to 176, wherein the microbial lysozyme is selected from the group consisting of amino acids 1 to 208 of SEQ ID NO: 1 and amino acids 1 to 207 of SEQ ID NO: 15.
179. The microbial lysozyme or composition comprising such of any one of embodiments 154 to 178 for use in the treatment of a human.
180. The microbial lysozyme or composition comprising such of any one of embodiments 154 to 179, wherein the composition is a liquid formulation.
181. The microbial lysozyme or composition comprising such of any one of embodiments 154 to 179, wherein the composition is a solid formulation.
182. The microbial lysozyme or composition comprising such of any one of embodiments 154 to 181, wherein the composition is a food or pharmaceutical composition or a medical device.
183. The microbial lysozyme or composition comprising such of any one of embodiments 154 to 182, wherein the composition is a food composition.

184. The microbial lysozyme or composition comprising such of any one of embodiments 154 to 182, wherein the composition is a pharmaceutical composition.
185. The microbial lysozyme or composition comprising such of any one of embodiments 154 to 182, wherein the composition is a medical device.
186. The microbial lysozyme or composition comprising such of any one of embodiments 154 to 185, wherein the composition is in the form of a powder, tablet, lozenge, effervescent tablet, capsule, emulsion, paste, individual sachet, chewing gum or oil drops.
187. The microbial lysozyme or composition comprising such of any one of embodiments 154 to 186, wherein the composition is administered by means of oral or rectal administration, to the extent possible.
188. Microbial lysozyme or a composition comprising microbial lysozyme for use in a method of increasing the proportion of bacteria of genus *Faecalibacterium* in the microbiome of the GI tract.
189. The microbial lysozyme or composition comprising such of embodiment 188, wherein a composition comprising a lysozyme is administered at a level of 0.1 to 1000 ppm enzyme protein per kg composition.
190. The microbial lysozyme or composition comprising such of embodiment 188 or 189, wherein a composition comprising a lysozyme is administered at a level of 1 to 200 mg enzyme protein per kg bodyweight, such as between between 1 to 150 mg, 2 to 100 mg, 2 to 90 mg, 2 to 80 mg or 10 to 70 mg enzyme protein per kg bodyweight.
191. The microbial lysozyme or composition comprising such of any one of embodiments 188 to 190, wherein a composition comprising a lysozyme is administered at a level of 0.04 to 11.0 µmol enzyme protein per kg bodyweight, such as between 0.1 to 6.0 µmol, 0.2 to 5.0 µmol, 0.3 to 4.0 µmol or 0.4 to 3.0 µmol enzyme protein per kg bodyweight.
192. The microbial lysozyme or composition comprising such of any one of embodiments 188 to 191, wherein the microbial lysozyme is obtained or obtainable from the kingdom Fungi.
193. The microbial lysozyme or composition comprising such of any one of embodiments 188 to 192, wherein the microbial lysozyme stabilizes the healthy microbiota in the GI tract and suppresses growth and/or intestinal colonization of bacterial pathogens.
194. The microbial lysozyme or composition comprising such of any one of embodiments 188 to 193, wherein the microbial lysozyme prevents, alleviates or treats inflammation.
195. The microbial lysozyme or composition comprising such of any one of embodiments 188 to 194, wherein the microbial lysozyme prevents, alleviates or treats inflammation in the GI tract.
196. The microbial lysozyme or composition comprising such of any one of embodiments 188 to 194, wherein the microbial lysozyme prevents, alleviates or treats inflammation in the upper GI tract.
197. The microbial lysozyme or composition comprising such of any one of embodiments 188 to 194, wherein the microbial lysozyme prevents, alleviates or treats inflammation in the lower GI tract.
198. The microbial lysozyme or composition comprising such of any one of embodiments 188 to 197, wherein the microbial lysozyme maintains remission of IBS and/or IBD.
199. The microbial lysozyme or composition comprising such of any one of embodiments 188 to 198, wherein the microbial lysozyme prevents, alleviates or treats post-surgery flare up.
200. The microbial lysozyme or composition comprising such of any one of embodiments 188 to 199, wherein the microbial lysozyme reduces ectopic lipid deposition associated with obesity such as e.g. diet induced obesity.
201. The microbial lysozyme or composition comprising such of any one of embodiments 188 to 200, wherein the proportion of bacteria of genus *Faecalibacterium* is increased by at least 1%, such as at least 2%, at least 3%, at least 4%, at least 5%, at least 10%, at least 15% or at least 20%.
202. The microbial lysozyme or composition comprising such of any one of embodiments 188 to 200, wherein the proportion of bacteria of genus *Faecalibacterium* is increased by a factor of at least 1.25, such as at least 1.50, at least 1.75, at least 2.0, at least 2.5 or at least 3.0.
203. The microbial lysozyme or composition comprising such of any one of embodiments 188 to 202, wherein the microbial lysozyme is obtained or obtainable from the phylum Ascomycota.
204. The microbial lysozyme or composition comprising such of any one of embodiments 188 to 203, wherein the microbial lysozyme is obtained or obtainable from the subphylum Pezizomycotina.
205. The microbial lysozyme or composition comprising such of any one of embodiments 188 to 204, wherein the microbial lysozyme comprises one or more domains selected from the list consisting of GH24 and GH25.
206. The microbial lysozyme or composition comprising such of any one of embodiments 188 to 205, wherein the microbial lysozyme comprises one or more domains from GH24.
207. The microbial lysozyme or composition comprising such of any one of embodiments 188 to 205, wherein the microbial lysozyme comprises one or more domains from GH25.
208. The microbial lysozyme or composition comprising such of any one of embodiments 188 to 207, wherein the microbial lysozyme is selected from the group consisting of:
(a) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;
(b) a variant of SEQ ID NO: 1 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(c) a fragment of the polypeptide of (a) or (b) that has lysozyme activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids;
(d) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4;
(e) a variant of SEQ ID NO: 4 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(f) a fragment of the polypeptide of (d) or (e) that has lysozyme activity wherein the fragment comprises at least 210 amino acids, such as at least 215 amino acids, at least 220 amino acids, at least 225 amino acids, at least 230 amino acids, at least 235 amino acids or at least 240 amino acids;
(g) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15;
(h) a variant of SEQ ID NO: 15 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and
(i) a fragment of the polypeptide of (g) or (h) that has lysozyme activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids.

209. The microbial lysozyme or composition comprising such of any one of embodiments 188 to 207, wherein the microbial lysozyme is selected from the group consisting of:
(a) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;
(b) a variant of SEQ ID NO: 1 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(c) a fragment of the polypeptide of (a) or (b) that has lysozyme activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids;
(d) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15;
(e) a variant of SEQ ID NO: 15 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and
(f) a fragment of the polypeptide of (d) or (e) that has lysozyme activity wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids.

210. The microbial lysozyme or composition comprising such of any one of embodiments 188 to 208, wherein the microbial lysozyme is selected from the group consisting of amino acids 1 to 208 of SEQ ID NO: 1, amino acids 1 to 245 of SEQ ID NO: 4 and amino acids 1 to 207 of SEQ ID NO: 15.

211. The microbial lysozyme or composition comprising such of any one of embodiments 188 to 209, wherein the microbial lysozyme is selected from the group consisting of amino acids 1 to 208 of SEQ ID NO: 1 and amino acids 1 to 207 of SEQ ID NO: 15.

212. The microbial lysozyme or composition comprising such of any one of embodiments 188 to 211 for use in the treatment of a human.

213. The microbial lysozyme or composition comprising such of any one of embodiments 188 to 212, wherein the composition is a liquid formulation.

214. The microbial lysozyme or composition comprising such of any one of embodiments 188 to 212, wherein the composition is a solid formulation.

215. The microbial lysozyme or composition comprising such of any one of embodiments 188 to 214, wherein the composition is a food or pharmaceutical composition or a medical device.

216. The microbial lysozyme or composition comprising such of any one of embodiments 188 to 215, wherein the composition is a food composition and/or supplement.

217. The microbial lysozyme or composition comprising such of any one of embodiments 188 to 215, wherein the composition is a pharmaceutical composition.

218. The microbial lysozyme or composition comprising such of any one of embodiments 188 to 215, wherein the composition is a medical device.

219. The microbial lysozyme or composition comprising such of any one of embodiments 188 to 218, wherein the composition is in the form of a powder, tablet, lozenge, effervescent tablet, capsule, emulsion, paste, individual sachet, chewing gum or oil drops.

220. The microbial lysozyme or composition comprising such of any one of embodiments 188 to 219, wherein the composition is administered by means of oral or rectal administration, to the extent possible.

221. The microbial lysozyme or composition comprising such of any one of embodiments 154 to 220, wherein the microbial lysozyme or composition comprising such is used in the treatment of Crohn's disease and/or Ulcerative colitis.

222. The method or use of any one of embodiments 1 to 153, wherein the microbial lysozyme reduces the amount of dead *Lactobacillus johnsonii* cells, or cell wall debris therefrom, in the digestive tract.

223. The method or use of any one of embodiments 1 to 153, wherein the microbial lysozyme is promoting the elimination of dead *Lactobacillus johnsonii* cells, or cell wall debris therefrom, from the digestive tract of humans.

224. The method or use of any one of embodiments 1 to 153 or 222 to 223, wherein the microbial lysozyme has lysozyme activity against *Lactobacillus johnsonii* as determined by Method for the Determination of Lysozyme Activity Against *Lactobacillus johnsonii*.

225. The method or use of any one of embodiments 222 to 224, wherein the microbial lysozyme is selected from the group consisting of a polpypeptide having at least 90% sequence identity to the polypeptide of SEQ ID NO: 1, a polpypeptide having at least 90% sequence identity to the polypeptide of SEQ ID NO: 15, a polpypeptide having at least 90% sequence identity to the polypeptide of SEQ ID NO: 18, a polpypeptide having at least 90% sequence identity to the polypeptide of SEQ ID NO: 21, a polpypeptide having at least 90% sequence identity to the polypeptide of SEQ ID NO: 24, a polpypeptide having at least 90% sequence identity to the polypeptide of SEQ ID NO: 27, and a polpypeptide having at least 90% sequence identity to the polypeptide of SEQ ID NO: 30, preferably selected from the group consisting of a polpypeptide having at least 90% sequence identity to the polypeptide of SEQ ID NO: 1, a polpypeptide having at least 90% sequence identity to the polypeptide of SEQ ID NO: 15, a polpypeptide having at least 90% sequence identity to the polypeptide of SEQ ID NO: 18, a polpypeptide having at least 90% sequence identity to the polypeptide of SEQ ID NO: 21, a polpypeptide having at least 90% sequence identity to the polypeptide of SEQ ID NO: 27, and a polpypeptide having at least 90% sequence identity to the polypeptide of SEQ ID NO: 30, more preferably selected from the group consisting of a polpypeptide having at least 90% sequence identity to the polypeptide of SEQ ID NO: 18, a polpypeptide having at least 90% sequence identity to the polypeptide of SEQ ID NO: 21, a polpypeptide having at least 90% sequence identity to the polypeptide of SEQ ID NO: 27, and a polpypeptide having at least 90% sequence identity to the polypeptide of SEQ ID NO: 30, even more preferably a polpypeptide having at least 90% sequence identity to the polypeptide of SEQ ID NO: 21 or a polpypeptide having at least 90% sequence identity to the polypeptide of SEQ ID NO: 27.

226. The method or use of any one of embodiments 222 to 224, wherein the microbial lysozyme is selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO: 1.

227. The method or use of any one of embodiments 222 to 224, wherein the microbial lysozyme is selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO: 21.

228. The method or use of any one of embodiments 222 to 224, wherein the microbial lysozyme is selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO: 27.

229. The method or use of any one of embodiments 222 to 228 wherein the microbial lysozyme has a lysozyme activity against *Lactobacillus johnsonii* at 5 ppm that increases optical density (OD) measurement at 405 nm of at least 0.20 as determined by Method for the Determination of Lysozyme Activity Against *Lactobacillus johnsonii*.

230. The method or use of any one of embodiments 222 to 229, wherein the microbial lysozyme having lysozyme activity prevents, alleviates or treats inflammation.

231. The method or use of any one of embodiments 222 to 230, wherein the microbial lysozyme having lysozyme activity prevents, alleviate and treats inflammation in the GI tract.

232. The method or use of any one of embodiments 222 to 230, wherein the microbial lysozyme having lysozyme activity prevents, alleviate and treats inflammation in the upper GI tract.

233. The method or use of any one of embodiments 222 to 230, wherein the microbial lysozyme having lysozyme activity prevents, alleviate and treats inflammation in the lower GI tract.

234. The microbial lysozyme or composition comprising such of any one of embodiments 154 to 221, wherein the microbial lysozyme reduces the amount of dead *Lactobacillus johnsonii* cells, or cell wall debris therefrom, in the digestive tract.

235. The microbial lysozyme or composition comprising such of any one of embodiments 154 to 221, wherein the microbial lysozyme is promoting the elimination of dead *Lactobacillus johnsonii* cells, or cell wall debris therefrom, from the digestive tract of humans.

236. The microbial lysozyme or composition comprising such of any one of embodiments 154 to 221 or 234 to 235, wherein the microbial lysozyme has lysozyme activity against *Lactobacillus johnsonii* as determined by Method for the Determination of Lysozyme Activity Against *Lactobacillus johnsonii*.

237. The microbial lysozyme or composition comprising such of any one of embodiments 234 to 236, wherein the microbial lysozyme is selected from the group consisting of a polpypeptide having at least 90% sequence identity to the polypeptide of SEQ ID NO: 1, a polpypeptide having at least 90% sequence identity to the polypeptide of SEQ ID NO: 15, a polpypeptide having at least 90% sequence identity to the polypeptide of SEQ ID NO: 18, a polpypeptide having at least 90% sequence identity to the polypeptide of SEQ ID NO: 21, a polpypeptide having at least 90% sequence identity to the polypeptide of SEQ ID NO: 24, a polpypeptide having at least 90% sequence identity to the polypeptide of SEQ ID NO: 27, and a polpypeptide having at least 90% sequence identity to the polypeptide of SEQ ID NO: 30, preferably selected from the group consisting of a polpypeptide having at least 90% sequence identity to the polypeptide of SEQ ID NO: 1, a polpypeptide having at least 90% sequence identity to the polypeptide of SEQ ID NO: 15, a polpypeptide having at least 90% sequence identity to the polypeptide of SEQ ID NO: 18, a polpypeptide having at least 90% sequence identity to the polypeptide of SEQ ID NO: 21, a polpypeptide having at least 90% sequence identity to the polypeptide of SEQ ID NO: 27, and a polpypeptide having at least 90% sequence identity to the polypeptide of SEQ ID NO: 30, more preferably selected from the group consisting of a polpypeptide having at least 90% sequence identity to the polypeptide of SEQ ID NO: 18, a polpypeptide having at least 90% sequence identity to the polypeptide of SEQ ID NO: 21, a polpypeptide having at least 90% sequence identity to the polypeptide of SEQ ID NO: 27, and a polpypeptide having at least 90% sequence identity to the polypeptide of SEQ ID NO: 30, even more preferably a polpypeptide having at least 90% sequence identity to the polypeptide of SEQ ID NO: 21 or a polpypeptide having at least 90% sequence identity to the polypeptide of SEQ ID NO: 27.

238. The microbial lysozyme or composition comprising such of any one of embodiments 234 to 236, wherein the microbial lysozyme is selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO: 1.

239. The microbial lysozyme or composition comprising such of any one of embodiments 234 to 236, wherein the microbial lysozyme is selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO: 21.

240. The microbial lysozyme or composition comprising such of any one of embodiments 234 to 236, wherein the microbial lysozyme is selected from the group consisting of a polypeptide having at least 80%, at least 85%, at least 90%, at least 91%, at least 92%, at least 93%, at least 94%, at least 95%, at least 96%, at least 97%, at least 98%, at least 99% or 100% sequence identity to the polypeptide of SEQ ID NO: 27.

241. The microbial lysozyme or composition comprising such of any one of embodiments 234 to 240 wherein the microbial lysozyme has a lysozyme activity against *Lactobacillus johnsonii* at 5 ppm that increases optical density (OD) measurement at 405 nm of at least 0.20 as determined by Method for the Determination of Lysozyme Activity Against *Lactobacillus johnsonii*.

242. The microbial lysozyme or composition comprising such of any one of embodiments 234 to 241, wherein the microbial lysozyme having lysozyme activity prevents, alleviates or treats inflammation.

243. The microbial lysozyme or composition comprising such of any one of embodiments 234 to 242, wherein the microbial lysozyme having lysozyme activity prevents, alleviate and treats inflammation in the GI tract.

244. The microbial lysozyme or composition comprising such of any one of embodiments 234 to 242, wherein the microbial lysozyme having lysozyme activity prevents, alleviate and treats inflammation in the upper GI tract.

245. The microbial lysozyme or composition comprising such of any one of embodiments 234 to 242, wherein the microbial lysozyme having lysozyme activity prevents, alleviate and treats inflammation in the lower GI tract.

EXAMPLES

Strains

*Trichophaea saccata* CBS804.70 was purchased from the Centraalbureau voor Schimmelcultures (Utrecht, the Netherlands). According to Central Bureau vor Schnimmelkulture, *Trichophaea saccata* CBS804.70 was isolated from coal spoil tip soil from Staffordshire, England in May 1968.

According to Central Bureau vor Schnimmelkulture, *Acremonium alcalophilum* CBS 114.92 was isolated by A. Yoneda in 1984 from the sludge of pig faeces compost near Tsukui Lake, Japan.

Media and Solutions

YP+2% glucose medium was composed of 1% yeast extract, 2% peptone and 2% glucose.

YP+2% maltodextrin medium was composed of 1% yeast extract, 2% peptone and 2% maltodextrin.

PDA agar plates were composed of potato infusion (potato infusion was made by boiling 300 g of sliced (washed but unpeeled) potatoes in water for 30 minutes and then decanting or straining the broth through cheesecloth. Distilled water was then added until the total volume of the suspension was one liter, followed by 20 g of dextrose and 20 g of agar powder. The medium was sterilized by autoclaving at 15 psi for 15 minutes (Bacteriological Analytical Manual, 8th Edition, Revision A, 1998).

LB plates were composed of 10 g of Bacto-Tryptone, 5 g of yeast extract, 10 g of sodium chloride, 15 g of Bacto-agar, and deionized water to 1 liter.

LB medium was composed of 10 g of Bacto-Tryptone, 5 g of yeast extract, 10 g of sodium chloride, and deionized water to 1 liter.

COVE sucrose plates were composed of 342 g of sucrose, 20 g of agar powder, 20 ml of COVE salts solution, and deionized water to 1 liter. The medium was sterilized by autoclaving at 15 psi for 15 minutes (Bacteriological Analytical Manual, 8th Edition, Revision A, 1998). The medium was cooled to 60° C. and 10 mM acetamide, 15 mM CsCl, TRITON® X-100 (50 µl/500 ml) were added.

COVE salts solution was composed of 26 g of $MgSO_4.7H_2O$, 26 g of KCL, 26 g of $KH_2PO_4$, 50 ml of COVE trace metals solution, and deionized water to 1 liter.

COVE trace metals solution was composed of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_4.2H_2O$, 10 g of $ZnSO_4.7H_2O$, and deionized water to 1 liter.

Example 1: Cloning, Expression and Purification of the GH25 Lysozyme from *Acremonium alcalophilum* CBS 114.92

The GH25 lysozyme from *Acremonium alcalophilum* CBS 114.92 (SEQ ID NO: 1) was cloned and expressed as described in example 2 and purified as described in example 5 of WO 2013/076253.

Example 2: Expression of the GH24 Lysozyme from *Trichophaea saccata*

The fungal strain was cultivated in 100 ml of YP+2% glucose medium in 1000 ml Erlenmeyer shake flasks for 5 days at 20° C. Mycelia were harvested from the flasks by filtration of the medium through a Buchner vacuum funnel lined with MIRACLOTH® (EMD Millipore, Billerica, Mass., USA). Mycelia were frozen in liquid nitrogen and stored at −80° C. until further use. Genomic DNA was isolated using a DNEASY® Plant Maxi Kit (QIAGEN GMBH, Hilden Germany) according to the manufacturer's instructions.

Genomic sequence information was generated by Illumina MySeq (Illumina Inc., San Diego, Calif.). 5 µgs of the isolated *Trichophaea saccata* genomic DNA was used for library preparation and analysis according to the manufacturer's instructions. A 100 bp, paired end strategy was employed with a library insert size of 200-500 bp. One half of a HiSeq run was used for the total of 95,744,298, 100 bp raw reads obtained. The reads were subsequently fractionated to 25% followed by trimming (extracting longest subsequences having Phred-scores of 10 or more). These reads were assembled using Idba version 0.19. Contigs shorter than 400 bp were discarded, resulting in 8,954,791,030 bp with an N-50 of 10,035. Genes were called using GeneMark.hmm ES version 2.3c and identification of the catalytic domain was made using "Phage lysozyme PF00959" Hidden Markov Model provided by Pfam. The polypeptide coding sequence for the entire coding region was cloned from *Trichophaea saccata* CBS804.70 genomic DNA by PCR using the primers F-80470 and R-80470 (SEQ ID NO: 6 and SEQ ID NO: 7 respectively) as described below.

(SEQ ID NO: 6)
5'-ACACAACTGG<u>GGATCC</u>ACCATGCACGCTCTCACCCTTCT-3'

(SEQ ID NO: 7)
5'-CTAGATCTCGAG<u>AAGCTT</u>TTAGCACTTGGGAGGGTGGG-3'

Bold letters represent *Trichophaea saccata* enzyme coding sequence. Restriction sites are underlined. The sequence to the left of the restriction sites is homologous to the insertion sites of pDau109 (WO 2005/042735).

Extensor HIFI PCR mix, 2× concentration (Thermo Scientific cat no AB-0795) was used for experiment.

The amplification reaction (25 μl) was performed according to the manufacturer's instructions (Thermo Scientific cat no AB-0795) with the following final concentrations:
PCR mix:
0.5 μM Primer F-80470
0.5 μM Primer R-80470
12.5 μl Extensor HIFI PCR mix, 2× conc.
11.0 μl H2O
10 ng of *Trichophaea saccata* CBS804.70 genomic DNA.

The PCR reaction was incubated in a DYAD® Dual-Block Thermal Cycler (BioRad, USA) programmed for 1 cycle at 94° C. for 30 seconds; 30 cycles each at 94° C. for 30 seconds, 52° C. for 30 seconds and 68° C. for 60 seconds followed by 1 cycle at 68° C. for 6 minutes. Samples were cooled to 10° C. before removal and further processing.

Three μl of the PCR reaction were analyzed by 1% agarose gel electrophoresis using 40 mM Tris base, 20 mM sodium acetate, 1 mM disodium EDTA (TAE) buffer. A major band of about 946 bp was observed. The remaining PCR reaction was purified directly with an ILLUSTRA™ GFX™ PCR DNA and Gel Band Purification Kit (GE Healthcare, Piscataway, N.J., USA) according to the manufacturer's instructions.

Two μg of plasmid pDau109 was digested with Bam HI and Hind III and the digested plasmid was run on a 1% agarose gel using 50 mM Tris base-50 mM boric acid-1 mM disodium EDTA (TBE) buffer in order to remove the stuffer fragment from the restricted plasmid. The bands were visualized by the addition of SYBR® Safe DNA gel stain (Life Technologies Corporation, Grand Island, N.Y., USA) and use of a 470 nm wavelength transilluminator. The band corresponding to the restricted plasmid was excised and purified using an ILLUSTRA™ GFX™ PCR DNA and Gel Band Purification Kit. The plasmid was eluted into 10 mM Tris pH 8.0 and its concentration adjusted to 20 ng per μl. An IN-FUSION® PCR Cloning Kit (Clontech Laboratories, Inc., Mountain View, Calif., USA) was used to clone the 983 bp PCR fragment into pDau109 digested with Bam HI and Hind III (20 ng). The IN-FUSION® total reaction volume was 10 μl. The IN-FUSION® total reaction volume was 10 μl. The IN-FUSION® reaction was transformed into FUSION-BLUE™ *E. coli* cells (Clontech Laboratories, Inc., Mountain View, Calif., USA) according to the manufacturer's protocol and plated onto LB agar plates supplemented with 50 μg of ampicillin per ml. After incubation overnight at 37° C., transformant colonies were observed growing under selection on the LB plates supplemented with 50 μg of ampicillin per ml.

Several colonies were selected for analysis by colony PCR using the pDau109 vector primers described below. Four colonies were transferred from the LB plates supplemented with 50 μg of ampicillin per ml with a yellow inoculation pin (Nunc NS, Denmark) to new LB plates supplemented with 50 μg of ampicillin per ml and incubated overnight at 37° C.

(SEQ ID NO: 8)
Primer 8653: 5'-GCAAGGGATGCCATGCTTGG-3'

(SEQ ID NO: 9)
Primer 8654: 5'-CATATAACCAATTGCCCTC-3'

Each of the three colonies were transferred directly into 200 μl PCR tubes composed of 5 μl of 2× Extensor HIFI PCR mix, (Thermo Fisher Scientific, Rockford, Ill., USA), 0.5 μl of primer 8653 (10 pm/μl), 0.5 μl of primer 8654 (10 pm/μl), and 4 μl of deionized water. Each colony PCR was incubated in a DYAD® Dual-Block Thermal Cycler programmed for 1 cycle at 94° C. for 60 seconds; 30 cycles each at 95° C. for 30 seconds, 60° C. for 45 seconds, 72° C. for 60 seconds, 68° C. for 10 minutes, and 10° C. for 10 minutes.

Three μl of each completed PCR reaction were submitted to 1% agarose gel electrophoresis using TAE buffer. All four *E. coli* transformants showed a PCR band of about 980 bp. Plasmid DNA was isolated from each of the four colonies using a QIAprep Spin Miniprep Kit (QIAGEN GMBH, Hilden Germany). The resulting plasmid DNA was sequenced with primers 8653 and 8654 (SEQ ID NO: 8 and 9) using an Applied Biosystems Model 3730 Automated DNA Sequencer using version 3.1 BIG-DYE™ terminator chemistry (Applied Biosystems, Inc., Foster City, Calif., USA). One plasmid, designated pKKSC0312-2, was chosen for transforming *Aspergillus oryzae* MT3568. *A. oryzae* MT3568 is an amdS (acetamidase) disrupted gene derivative of *Aspergillus oryzae* JaL355 (WO 2002/40694) in which pyrG auxotrophy was restored by inactivating the *A. oryzae* amdS gene. Protoplasts of *A. oryzae* MT3568 were prepared according to the method described in European Patent, EP0238023, pages 14-15.

*E. coli* 3701 containing pKKSC0312-2 was grown overnight according to the manufacturer's instructions (Genomed) and plasmid DNA of pKKSC0312-2 was isolated using a Plasmid Midi Kit (Genomed JETquick kit, cat.nr. 400250, GENOMED GmbH, Germany) according to the manufacturer's instructions. The purified plasmid DNA was transformed into *Aspergillus oryzae* MT3568. *A. oryzae* MT3568 protoplasts were prepared according to the method of Christensen et al., 1988, Bio/Technology 6: 1419-1422. The selection plates consisted of COVE sucrose with +10 mM acetamide +15 mM CsCl+TRITON® X-100 (50 μl/500 ml). The plates were incubated at 37° C. Briefly, 8 μl of plasmid DNA representing 3 ugs of DNA was added to 100 μl MT3568 protoplasts. 250 μl of 60% PEG solution was added and the tubes were gently mixed and incubate at 37° for 30 minutes. The mix was added to 10 ml of pre melted Cove top agarose (The top agarose melted and then the temperature equilibrated to 40 C in a warm water bath before being added to the protoplast mixture). The combined mixture was then plated on two Cove-sucrose selection petri plates with 10 mM Acetamide. The plates were incubated at 37° C. for 4 days. Single *Aspergillus* transformed colonies were identified by growth on plates using the selection Acetimide as a carbon source. Each of the four *A. oryzae* transformants were inoculated into 750 µl of YP medium supplemented with 2% glucose and also 750 µl of 2% maltodextrin and also DAP4C in 96 well deep plates and incubated at 37° C. stationary for 4 days. At the same time the four transformants were restreaked on COVE-2 sucrose agar medium.

Culture broth from the *Aspergillus oryzae* transformants were then analyzed for production of the GH24 polypeptide by SDS-PAGE using NUPAGE® 10% Bis-Tris SDS gels (Invitrogen, Carlsbad, Calif., USA) according to the manufacturer's recommendations. A protein band at approximately 27 kDa was observed for each of the *Aspergillus oryzae* transformants. One *A. oryzae* transformant was cultivated in 1000 ml Erlenmeyer shake flasks containing 100 ml of DAP4C medium at 26° C. for 4 days with agitation at 85 rpm.

Example 3: Purification of the GH24 Lysozyme from *Trichophaea saccata*

The fermentation supernatant with the GH24 lysozyme from example 3 was filtered through a Fast PES Bottle top filter with a 0.22 µm cut-off. The resulting solution was diafiltrated with 5 mM Na-acetate, pH 4.5 and concentrated (volume reduced by a factor of 10) on an Ultra Filtration Unit (Sartorius) with a 10 kDa cut-off membrane.

After pretreatment about 275 mL of the lysozyme containing solution was purified by chromatography on SP Sepharose (approximately 60 mL) in a XK26 column eluting the bound lysozyme with 0 to 100% gradient of buffer A (50 mM Na-acetate pH 4.5) and buffer B (50 mM Na-acetate+1 M NaCl pH 4.5) over 10 column volumes. The fractions from the column were pooled based on the chromatogram (absorption at 280 and 254 nm) and SDS-PAGE analysis.

The molecular weight, as estimated from SDS-PAGE, was approximately 27 kDa and the purity was >90%.

Example 4: Other Characteristics for the GH24 Lysozyme from *Trichophaea saccata*

Determination of the N-terminal sequence was: YPVKTDL.

The calculated molecular weight from this mature sequence is 26205.5 Da $(M+H)^+$.

The molecular weight determined by intact molecular weight analysis was 26205.3 Da. $(M+H)^+$.

The mature sequence (from EDMAN N-terminal sequencing data, intact molecular weight analysis and proteomic analysis):

```
                                          (SEQ ID NO: 4)
YPVKTDLHCRSSPSTSASIVRTYSSGTEVQIQCQTT-GTSVQGSNVWDKTQ

HGCYVADYYVKTGHSGIFTTKCGSSSGGGSCKPPPINAAT-VALIKEFEGF

VPKPAPDPIGLPTVGYGHLCKTKGCKEVPYSFPLTQETATKLLQSDIK-TF

TSCVSNYVKDSVKLNDNQYGALASWAFNVGCGNVQTSS-LIKRLNAGENPN

TVAAQELPKWKYAGGKVMPGLVRRRNAEVALFKKPSSVQAHPPKC.
```

Example 5: Determination of Lysozyme Activity

Lysozyme activity was determined by measuring the decrease (drop) in absorbance/optical density of a solution of resuspended *Micrococcus lysodeikticus* ATTC No. 4698 (Sigma-Aldrich M3770) or *Exiguobacterium undea* (DSM14481) measured in a spectrophotometer at 540 nm.

Preparation of *Micrococcus lysodeikticus* Substrate

Before use the cells were resuspended in citric acid-phosphate buffer pH 6.5 to a concentration of 0.5 mg cells/mL and the optical density (OD) at 540 nm was measured. The cell suspension was then adjusted so that the cell concentration equalled an OD540=1.0. The adjusted cell suspension was then stored cold before use. Resuspended cells were used within 4 hours.

Preparation of Dried Cells of *Exiguobacterium undae* Substrate

A culture of *E. undae* (DSM14481) was grown in 100 mL LB medium (Fluka 51208, 25 g/L) in a 500 mL shake-flask at 30° C., 250 rpm overnight. The overnight culture was then centrifuged at 20° C. and 5000 g for 10 minutes, and the pellet was then washed twice with sterile milliQ water, and resuspended in Milli-Q water. The washed cells were centrifuged for 1 minute at 13000 rpm and as much as possible of the supernatant was decanted. The washed cells were dried in a vacuum centrifuge for 1 hour. The cell pellet was resuspended in citric acid-phosphate buffer pH 4, 5 or 6 so that the optical density (OD) at 540 nm=1.

Measurement of Lysozyme Antimicrobial Activity in the Turbidity Assay

The lysozyme sample to be measured was diluted to a concentration of 100-200 mg enzyme protein/L in citric acid-phosphate buffer pH 4, 5 or 6, and kept on ice until use. In a 96 well microtiterplate (Nunc) 200 µL of the substrate was added to each well, and the plate was incubated at 37° C. for 5 minutes in a VERSAmax microplate reader (Molecular Devices). Following incubation, the absorbance of each well was measured at 540 nm (start value). To start the activity measurement, 20 µL of the diluted lysozyme sample was added to each substrate (200 µL) and kinetic measurement of absorbance at 540 nm was initiated for minimum 30 minutes up to 24 hours at 37° C. The measured absorbance at 540 nm was monitored for each well and over time a drop in absorbance is seen if the lysozyme has lysozyme activity. The results are presented in table 1 below.

TABLE 1

Lysozyme Activity against *Micrococcus lysodeikticus* and *Exiguobacterium undea* as measured by Optical Density Drop

| Lysozyme | *Micrococcus lysodeikticus*[1] | *Exiguobacterium undae*[1] |
| --- | --- | --- |
| GH22 lysozyme from *Gallus gallus* (SEQ ID NO: 5) | +++ (pH 6) | + (pH 6) |
| GH24 lysozyme from *Trichophaea saccata* (SEQ ID NO: 4) | ++ (pH 6) | ++ (pH 6) |
| GH25 lysozyme from *A. alcalophilum* (SEQ ID NO: 1) | + (pH 4) | + (pH 5) |

[1]−Means no effect; + means small effect; ++ means medium effect; +++ means large effect. The pH value in the brackets lists the assay pH based on lysozyme-substrate combination.

The data confirms that the GH22 lysozyme from *Gallus gallus*, the GH24 lysozyme from *Trichophaea saccata* and the GH25 lysozyme from *A. alcalophilum* all have lysozyme activity.

Example 6 In Vivo Trial in Mice—Immunomodulatory Properties in Colitis Mouse Model Animals and Housing Female BalbC mice (6 weeks old on arrival, Charles Rivers UK Limited) were randomly housed in cages of 3 on arrival based on weight with a 12 hours light dark cycle.

An acclimatization period of 14 days was allowed, before start of experimental procedures.

Feeding and Treatment

Mice had access to standard chow (maintenance RM1P diet, Special Diet Services, UK) ad libitum. Water was available from bottles ad libitum.

The mice were grouped in numbers of 12. Animals were treated by oral gavage (<20 mL/Kg) once a day with test compounds or vehicle according to table 2. First administration was 2 days prior to dextran sulfate sodium (DSS) treatment and continued until the day before termination of the study (a total of 7 days of treatment).

TABLE 2

Study design

| Group | Treatment | DSS (+/−) | Daily dose (oral gavage) [mg] | Daily dose (oral gavage) [mmol] |
|---|---|---|---|---|
| 1 | Vehicle | − | — | — |
| 2 | Vehicle | + | — | — |
| 3 | SEQ ID NO: 1 (High) | − | 0.93 | 4.05E−05 |
| 4 | SEQ ID NO: 1 (High) | + | 0.93 | 4.05E−05 |
| 5 | SEQ ID NO: 1 (Medium) | + | 0.20 | 0.85E−05 |
| 6 | SEQ ID NO: 1 (Low) | + | 0.04 | 0.17E−05 |
| 7 | SEQ ID NO: 15 (High) | + | 1.00 | 4.18E−05 |
| 8 | SEQ ID NO: 15 (Medium) | + | 0.21 | 0.86E−05 |
| 9 | SEQ ID NO: 15 (Low) | + | 0.04 | 0.17E−05 |
| 10 | SEQ ID NO: 5 (High) | + | 1.07 | 7.47E−05 |
| 11 | SEQ ID NO: 5 (Medium) | + | 0.22 | 1.54E−05 |
| 12 | SEQ ID NO: 5 (Low) | + | 0.04 | 0.31E−05 |

Induction of Colitis with Dextran Sulfate Sodium (DSS)

To induce colitis, dextran sulfate sodium (DSS) was added to the drinking water (3% w/v). 5 days after DSS administration the animals were culled and endpoint analysis performed as detailed below. DSS was added to the drinking water immediately after dosing with test-compounds on day 0.

Experimental Parameters and Analyses

Careful clinical examinations were carried out daily and included observations of changes in skin, fur, eyes, mucous membranes, occurrence of secretions and excretions (e.g. diarrhoea) and autonomic activity (e.g. lacrimation, salivation, piloerection, pupil size, unusual respiratory pattern. Changes in gait, posture and response to handling, as well as the presence of bizarre behaviour, tremors, convulsions, sleep and coma were also noted. The weight of each animal was furthermore recorded daily.

Faeces sampling from all mice were taken at day −3 (before first treatment with test-compounds) and at day 0 (just before DSS being added to drinking water). Samples were collected freshly through natural defecation from individual mice. These were collected in sterile/DNAse free Eppendorf tubes and stored at −80° C.

5 days after DSS was added to the drinking water, the animals were euthanized and the endpoint procedures described below were carried out.

Colon was extracted, washed and opened. Inflammation grading of the colon was performed macroscopically using a light microscope and were conducted by 2 blinded observers based on the Wallace scoring method. Criteria for the scoring of colonic damage was:

0—no damage.
1—Hyperemia. No ulcers.
2—Hyperemia and thickening of bowel wall. No ulcers.
3—One ulcer without thickening of the bowel wall.
4—Two or more sites of ulceration or inflammation.
5—Two or more major sites of ulceration and inflammation or one site of ulceration/inflammation extending >1 cm along the length of the colon.
6-10—If damage covers >2 cm along the length of the colon, the score was increased by 1 for each additional centimetre.

The contents of the cecum and colon were removed at the time of culling, snap frozen in separate tubes and stored at −80° C. until being shipped.

The proximal half of the colon was removed following Wallace scoring and weighed. Each sample was placed in an Eppendorf tube and snap frozen before being stored at −80° C. until being used for cytokine analysis.

A section of the proximal colon was placed in a lysing tube containing lysing solution (protease inhibitor and tissue protein extraction reagent at a ratio of 1 g of colon tissue to 5 mL of lysing solution). The tissue was homogenised 3 times at 6800 rpm for 30 s. The homogenised samples where then centrifuged (1000 rpm for 5 min at 4° C.) to extract the protein and the resulting supernatant aliquoted for cytokine analysis.

Supernatant from homogenised colon sections were evaluated for cytokine levels using a multiplex assay (Merck Millipore) for a range of Th1 and Th17 specific cytokines (IL-10, TNF-α, IL-1β, IL-6, IL-12, IL-17a, IL-25) using a Magpix system (Luminex).

Results:

Treatment with DSS (3% w/v) in the drinking water for 5 days caused an inflammatory effect in the colon of mice when compared to the control animals exposed to normal drinking water, as indicated by an increase in the mean Wallace score (FIG. 1A).

Treatment with SEQ ID NO: 1 dose dependently inhibited the DSS induced inflammatory effect. A similar effect on Wallace score was seen after treatment with SEQ ID NO: 5. SEQ ID NO: 15 also inhibited the DSS induced inflammation although not as effective as SEQ ID NO: 1 and SEQ ID NO: 5 (FIG. 1A).

The length of the colon is an indicator of the severity of injury as colitis increases edema and shortens the overall colon length. In the current study the colon length in all groups were comparable, thus confirming that it was only a mild inflammation that were induced by DSS (FIG. 1B).

Due to the inflammation colon weights in animals exposed to DSS (3% w/v) and treated with vehicle buffer were increased when compared to control animals exposed to normal drinking water. Treatment with SEQ ID NO: 1 in DSS exposed animals, however, caused a dose dependent reduction to the increased colon wet weight that was seen in the disease control group. A dose dependent trend to reduce the colon weight was also seen after treatment with SEQ ID NO: 5, however this was not as pronounced as for SEQ ID NO: 1 indicating a better performance of SEQ ID NO: 1 compared to SEQ ID NO: 5. Treatment with SEQ ID NO: 15 did not effect the DSS induced increased colon wet weight (FIG. 1C).

The weight of the mice was monitored from day −3 where prophylactic treatment with either controls or SEQ ID NO: 1, SEQ ID NO: 15 or SEQ ID NO: 5 were started. The weight gain (day −3-0) was comparable between groups (FIGS. 2 and 3), the body weight continued to increase in all groups over this period as expected from mice of this age. From day 0, where DSS challenge was started there was an apparent mild reduction in body weight in all groups of animals receiving DSS in their drinking water of approximately 2 or 3 g body weight by day 4 (FIGS. 2 and 3). A dose dependent inhibition of this colitis associated weight loss can be seen following treatment with either SEQ ID NO: 1, SEQ ID NO: 15 or SEQ ID NO: 5 (FIG. 3), with SEQ ID NO: 1 being most effective off all at the highest dose tested (FIG. 5).

Tumor necrosis factor-α (TNF-α) is a multifunctional pro-inflammatory cytokine secreted by a wide variety cells including monocytes/macrophages, neutrophils and T-lymphocytes.

As expected the disease control group expresses high level of pro-inflammatory cytokines (TNF-α, IL-1β, IL-6, IL-17a and IL-25) in their colons compared to healthy control animals. In addition, the pro-inflammatory cytokine IL-12 as well as the regulatory cytokine IL-10 is induced although to a lesser degree following DSS challenge (FIG. 4).

Treatment with SEQ ID NO: 1, SEQ ID NO: 15 and SEQ ID NO: 5 reduces the DSS induced cytokine levels in a dose dependent manner. SEQ ID NO: 15 only had a small effect on cytokine levels in colon compared to SEQ ID NO: 1 and SEQ ID NO: 5. Surprisingly SEQ ID NO: 1 was overall most effective in reducing the cytokine levels. In particularly for the key drivers of inflammation TNF-α, IL-1b and IL-6 (FIG. 4).

The superiority of SEQ ID NO: 1 over SEQ ID NO: 5 is even more clearly seen when the different size of the proteins is taken into consideration, thus SEQ ID NO: 1, SEQ ID NO: 15 and SEQ ID NO: 5 has a molecule size of 23.0, 24.0 and 14.3 kDa respectively. In FIG. 5 the cytokine levels in colons are shown as a function of mol of test compounds/mouse/day. It can clearly be seen that SEQ ID NO: 1 overall reduces the cytokine levels more effective than SEQ ID NO: 5.

In the current study the mice were dosed with a similar concentration (mg/mouse/day) of each of the test compounds, however due to the different molecule size this mean that about 40% less molecules have been dosed with SEQ ID NO: 1 and SEQ ID NO: 15 compared to SEQ ID NO: 5, surprisingly despite of this, the immunomodulatory performance of SEQ ID NO: 1 was better than SEQ ID NO: 5.

In summary DSS (3% w/v.) added to the drinking water for 5 days caused an inflammatory effect in the colon as expected. This was both evident with respect to the Wallace scoring as an index of inflammation and the increase in the colon weight. The evaluated Th1 and Th17 cytokines also supported an inflammatory effect being induced by DSS.

Treatment (day-3 to day 5) with the SEQ ID NO: 1, SEQ ID NO: 15 or SEQ ID NO: 5 caused a consistent inhibitory effect at reducing the DSS induced inflammatory effect in the colon. This was observed with both a reduction in proinflammatory cytokine levels and the resulting inflammation observed (as indicated by Wallace scoring). SEQ ID NO: 1 were the most effective compound at reducing the inflammation and improving the health of the animals, indicating that treatment with SEQ ID NO: 1 have a potential protective effect in preventing colitis in man.

Example 7 In Vivo Trial in Mice—Efficacy of Gut Microbial Modulation on Diet Induced Obesity and Glucose Tolerance Animals and Housing 36 male C57BL/6J mice (Jackson Lab, Bar Harbor, Me., USA), 6 weeks of age upon arrival, were randomly assigned to experimental groups based on their body weight at time of enrolment ensuring equal standard deviation and average body weight in all groups. Mice were housed 3 per cage with 12 mice/4 cages per group and acclimatized on low fat reference diet (LFD) for 12 days prior to experiment start.
Feeding and Treatment Mice were fed pelleted non-dyed feed ad libitum changed thrice a week with feed intake measurement. Mice were fed a high-fat-high-sucrose diet (HFD, D12451, Research Diet) or a low-fat reference diet (LFD, D12450H, Research Diet). The feed was stored at 4° C. until use (according to the manufacturer's instructions).

Sterile water was available from bottles ad libitum and changed weekly.
Experimental Parameters and Analyses Test compounds or vehicle (PBS pH 7.4, Ref: 10010-023, Gibco) were administered by daily oral gavage (25 G needle) of 100 µL at 10 a.m. SEQ ID NO: 1 of ~5 mg/mL were stored at −20 degrees until use.

Body composition of individual mice was assessed by the average of three measures of magnetic resonance (MR) scans (Minispec LF90, Bruker, calibrated daily when in use) in week 0, 4, 8, and 12 of the experimental protocol. Fresh feces were collected at the same time as MR scans in the beginning of the light cycle (8 AM±1 hour) prior to daily gavage. The samples were immediately frozen on dry ice and stored at −80° C. until further processing An oral glucose tolerance test along with glucose stimulated insulin secretion and gut permeability was assessed in week 10 of the experimental protocol. Mice were fasted at 8 AM for 5 h and gavaged at 10 AM. 5 h fasted blood glucose measurement (OneTouch Vario Flex, LifeScan) and sampling of the blood from the tail vein were executed prior to oral gavage with 4 µL/g lean mass of 50% dextrose solution and 150 µL sulfonic acid solution. Sulfonic acid solution consisted of 1.5 mg fluorescein-5 (6)-sulfonic acid (Invitrogen) dissolved in 150 µL suspension of 0.5% Carboxymethylcellulose Sodium Salt (CMC) (Medium viscosity, Sigma) in distilled water. Blood glucose was measured from tail vein puncture at time points 0, 15, 30, 60, 90, and 120 min after dextrose challenge and blood samples for insulin and gut permeability were taken in EDTA prepared capillary tubes (Microvette CB300, Sarstedt) at time points 0, 15, 30, 60, and 120 min post challenge. Mice received 0.5 mL saline (0.9% Sodium Chloride, Hospira) after the procedure allowing the mice to rehydrate. Blood samples were centrifuged for 10 min at 1000 rcf at room temperature. For insulin measurements, the first 5 µL of plasma was transferred to 96-well PCR plates on dry ice and kept at −80° C. until downstream processing. The next 5 µL of plasma, used for gut permeability test, was transferred to black 96-well optical-button plates (Nunc) and kept on wet ice until addition of 150 µL of 0.5% CMC in distilled water and thoroughly mixed. The plate was read on Synergy HT Microplate reader (BioTek) at excitation/emission 485/528 nm wavelength. Insulin levels were measured by Mouse ultrasensitive Insulin ELISA (Ref: 80-INDMSU-E10, Lot: 06489, Alpco) following the manufacturer's protocol and quantified on EnSpire 2300 multilabel reader (PerkinElmer).

Necropsy was carried out in week 12 of the experimental protocol. Mice were fasted from 7.15 AM±15 min and gavaged at 10 AM. Euthanasia was done in alternating order. Mice were anesthetized with isoflurane (3% in 65% N2, 35% O2, Fresenius Kabi). The first and last mouse in each cage of 3 were injected intravenously by 2 µL/g body weight insulin (Humulin 100 mU/mL diluted to 1.9 mU/µL, Lilly) 5 min prior to euthanasia. One of three (second mouse) was injected 2 µL/g body weight saline (0.9% Sodium Chloride, Hospira). Cardiac puncture was done using a 25 G needle and 1 mL syringe coated with EDTA. Blood was transferred to Eppendorf tubes containing 1 µL of DPP IV inhibitor (Millipore) and 1 µL of a protease inhibitor cocktail (P8340, Sigma). The samples were centrifuged at 1000 rcf for 10 min and plasma were aliquoted in triplicates, placed on dry ice and transferred to −80° C. storage until further processing.

Tissue harvesting: The weight of the liver, pancreas, eWAT, iWAT, rpWAT, iBAT, heart, quadriceps, gastrocnemius, brain and colon were measured and the tissues immediately frozen in liquid nitrogen and stored at −80° C. Tissues were dissected by the same operator and taken in the same order for all mice. The brain was frozen in liquid nitrogen <60 sec. post mortem. The length of the small intestine (from stomach to cecum) and colon (from cecum to rectum) were measured and kept on Plexiglas plate cooled by underlying wet ice throughout the handling time. Duodenum was considered the first 5 cm of the small intestine and the remaining small intestine tissue was divided in 3 parts of equal length. The first 3 cm were discarded, and the remaining of the proximal ⅔ of the small intestine was categorized as jejunum. The first 3 cm of the distal ⅓ of the small intestine was discarded and the remaining tissue categorized as ileum. The most proximal cm of duodenum, jejunum, ileum and colon was saved for histology in Carnoy's solution (to preserve mucous layer integrity) consisting of 60% methanol, 30% chloroform, and 10% glacial acetic acid prior to emptying the intestinal tissues. Content of the small intestine, cecum, and colon were isolated by mechanical pressure, frozen on dry ice and subsequently stored at −80° C. Tissue from duodenum, jejunum, ileum, colon, and cecum were snap frozen in liquid nitrogen and stored at −80° C. Metabolic tissues for histology from liver, eWAT, iWAT, and iBAT were preserved in a 4% paraformaldehyde solution for 72 hours followed by preservation in 70% ethanol. Liver tissue was additionally preserved in Tissue-Tek O.C.T Compound (Sakura Finetek) to enable histological Oil Red O lipid staining.

Results

HFD feeding induced severe diet induced obesity from week 2 and throughout the experiment. Treatment with SEQ ID NO: 1 did not protect against increased body weight (FIG. 1A). However, when analyzing body composition by magnetic resonance scanning, SEQ ID NO: 1 treated mice appeared to have decreased fat mass at week 12, but not at any of the prior weeks (FIG. 1B), suggesting that SEQ ID NO: 1 treatment may improve fat accretion in diet induced obese mice (FIG. 1C) without affecting body weight development (FIG. 1A).

Impaired glucose regulation is tightly connected to a range of lifestyle mediated diseases. We therefore tested if treatment with SEQ ID NO: 1 could ameliorate HFD induced glucoregulatory abnormalities independent of diet induced obesity. Increased fasting insulin (hyperinsulinemia) and fasting blood glucose (hyperglycemia) are biological markers of insulin resistance and both parameters were improved in SEQ ID NO: 1 treated mice compared to HFD fed control mice (FIG. 2A-B). The enhanced glucose regulation was reinforced by the glucose tolerance test, where SEQ ID NO: 1 treated mice cleared the glucose challenge more efficiently than HFD fed control mice (FIG. 2C). The improved glucose tolerance was not explained by increased beta cell capacity of insulin secretion (FIG. 2D), hence suggesting improved insulin sensitivity in metabolic tissues of SEQ ID NO: 1 treated mice. Combined, these data indicate that SEQ ID NO: 1 protects against obesity-related insulin resistance; a common denominator of Type 2 diabetes and cardiovascular diseases.

HFD induced metabolic inflammation is most often caused by decreased gut barrier function (leaky gut) allowing for increased circulating levels of the bacterial cell wall component, lipopolysaccharide (LPS). To test the gut barrier function, we challenged mice orally with 150 µl of 0.5% Carboxymethylcellulose Sodium Salt (CMC), 1% fluorescein-5 (6)-sulfonic acid solution and measured the fluorescence in plasma samples withdrawn from the tail vein at 0, 15, 30, 60 and 120 minutes post challenge. SEQ ID NO: 1 treated mice exhibited increased barrier function, indicating that SEQ ID NO: 1 relieve HFD induced metabolic inflammation.

Example 8 Method for the Determination of Lysozyme Activity Against *Lactobacillus johnsonii* (A)

PGN Extraction:
Cultivation of *Lactobacillus johnsonii*:
Materials
MRS broth, product number BD 288130, pH 6.3-6.7.
MRS agar plates, BD 288130; Agar Oxoid LP0011; pH 6.3-6.7.
0.9% NaCl, Merck 106404, Cas no. 7647145
Jars, supplier Merck 116387, Anaerocult anaerobic jar 2.5 L
Anaerogen 2.5 L, ThermoScientific, catalogue no. AN0025A
*Lactobacillus johnsonii*, DSM10533
Procedure

*L. johnsonii* was streaked from freeze stock to MRS agar plate and incubated under anaerobic conditions for 2 days, anaerobic jar with Anaerogen 2.5 L, 30° C. Some colonies were inoculated into 500 ml MRS broth in a 500 ml blue cap bottle and placed in an anaerobic jar with Anaerogen 2.5 L for 72 hours at 30° C.

The culture was spun down (6000 rpm, 10 minutes) and the supernatant was poured off before another round of centrifugation was performed. The pellet was washed in 100 ml 0.9% NaCl and the suspension was mixed well and centrifuged at 6000 rpm for 10 minutes. The supernatant was poured off and the washing procedure in 0.9% NaCl was repeated to a total of three washes. Approximately 40 ml 0.9% NaCl was added to the pellet and the solution was transferred to a 50 ml falcon tube. The solution was centrifuged at 6000 rpm for 10 minutes and the supernatant was poured off. The pellet was stored at −18° C. until the extraction of the peptidoglycan was conducted.

Extraction Procedure:
Materials
Protease from *Streptomyces griseus*, Sigma-Aldrich P5147, CAS 9036-06-0
PBS pH 7.3:
  NaCl: 8 g, Sigma-Aldrich 31434, CAS 7647-14-5
  KCl: 0.2 g, Sigma-Aldrich P9333, CAS 7447-40-7
  KH2PO4: 0.24 g, Sigma-Aldrich P5655, CAS 7778-77-0
  Na2HPO4.2H2O: 1.44 g, Sigma-Aldrich 30412, CAS 10028-24-7
  Add Milli-Q water to 1000 mL
1% Triton-X 100 solution:
  1 mL Triton X100, Sigma-Aldrich X100, CAS 9002-93-1
  Add Milli Q water to 100 mL
500 mM sodium carbonate buffer, pH 9.3:
  500 mM sodium carbonate is made from 21 g Na2CO3 (Sigma-Aldrich S7795, CAS 497-19-8) in 500 mL MQ water 500 mM sodium bicarbonate is made from 72 g NaHCO3 (Sigma-Aldrich S6014, CAS 144-55-8) in 500 mL MW water
  The pH 9.3 buffer is made from 320 mL NaHCO3 and 80 mL Na2CO3 and adjusting pH with HCl
Phenol solution with 10 mM Tris HCl, pH 8.0, 1 mM EDTA, Sigma-Aldrich P4557, CAS 108-95-2
Acetone, Sigma-Aldrich 32201-M, CAS 67-64-1
Ethanol, 96%, CCS Healthcare 1680643, CAS 64-17-5

Procedure

L. johnsonii cell material was freeze dried. The freeze dried material (525 mg) was suspended in PBS (40 mL) in a 50 mL Falcon tube. The suspension was shaken for 2 h @ 700 rpm in a thermoshaker at room temperature. Streptomyces griseus protease (55 mg) was then added and the suspension was incubated 6 h @ 37 C in the thermoshaker. It was then centrifuged 20 min @ 1900 g at room temperature, and the supernatant was decanted. The pellet was re-suspended in 1% Triton X-100 (40 mL) and shaken overnight @ 37 C. After another centrifugation and decantation, the pellet was re-suspended in PBS (40 mL) and protease (55 mg) added again. The suspension was again incubated 6 h @ 37 C, centrifuged and decanted. The pellet was re-suspended in PBS (40 mL) and shaken overnight @ 37 C. This washing procedure was repeated once more with PBS (40 mL, 30 min agitation), then with 50% ethanol/water (40 mL, 30 min agitation). The pellet was then split into two Falcon tubes. To each tube was added phenol solution (15 mL) pre-heated to 40 C. The suspensions were shaken 10 min @ 40 C, and then added 96% ethanol (25 mL to each tube), centrifuged and decanted. The pellets were further washed with acetone (40 mL in each tube) and 96% ethanol (40 mL in each tube), before being freeze dried. Combining the pellets from the two tubes yielded 80 mg purified peptidoglycan as a white powder.

Reducing End Assay

The lysozyme was diluted in phosphate dilution buffer (5 mM citrate, 5 mM $K_2HPO_4$, 0.01% TritonX-100, pH 5.0) to 50 μg/mL in polypropylene tubes, dependent on the strength of available stock solutions. The diluted lysozyme was further diluted in a 96-well polypropylene microtiter plate by preparing a two-fold dilution series down to a concentration of 6.3 μg/mL in phosphate dilution buffer (5 mM citrate, 5 mM $K_2HPO_4$, 0.01% TritonX-100, pH 5.0). A 50 mg/ml stock solution of L. johnsonii substrate in MillQ was prepared and diluted in phosphate buffer (50 mM citrate, 50 mM $K_2HPO_4$, pH 5.0) to 250 μg/ml. In a polypropylene deepwell plate 50 μL of the lysozyme dilution was mixed with 450 μL L. johnsonii solution and incubated at 40° C. with shaking (500 rpm) for 45 min. After incubation, the deepwell plate was centrifuged (3200 rpm, 7 min) to pellet insoluble material and 100 μL of the supernatant was mixed with 50 μL 3.2M HCl in a 96-well PCR plate and incubated at 95° C. for 80 min. 50 μL of 3.5 M NaOH was added to each well of the PCR plate, and 150 μL of each sample was transferred to a new PCR plate containing 75 μL/well 4-hydroxybenzhydrazide (PAHBAH) solution in K-Na tartrate/NaOH buffer (50 g/L K-Na tartrate+20 g/L NaOH). The plate was incubated at 95° C. for 10 min before 100 μL/sample was transferred to a clear flat-bottomed microtiter plate for optical density (OD) measurement at 405 nm. OD measurements were performed on three times diluted samples (50 μL sample diluted in 100 μL in Milli-Q water). The OD measurement values represent the difference after the original (background) reading was subtracted and represent the average of two OD measurement values.

Results are shown in Table 3.

TABLE 3

Average OD405 measurements (background corrected) in Reducing End Assay

| Lysozyme | Concentration of lysozyme in μg/mL | | | | | |
|---|---|---|---|---|---|---|
| | 20 | 10 | 5 | 2.5 | 1.25 | 0.63 |
| SEQ ID NO: 18 | 1.10 | 0.98 | 0.86 | 0.53 | 0.40 | 0.20 |
| SEQ ID NO: 24 | 1.20 | 0.84 | 0.70 | 0.53 | 0.34 | 0.22 |
| SEQ ID NO: 30 | 1.23 | 1.05 | 0.84 | 0.75 | 0.59 | 0.27 |

TABLE 3-continued

Average OD405 measurements (background corrected) in Reducing End Assay

| Lysozyme | Concentration of lysozyme in μg/mL | | | | | |
|---|---|---|---|---|---|---|
| | 20 | 10 | 5 | 2.5 | 1.25 | 0.63 |
| SEQ ID NO: 21 | ND | ND | 1.14 | 0.96 | 0.69 | 0.56 |
| SEQ ID NO: 27 | ND | ND | 1.62 | 0.98 | 0.57 | 0.39 |
| SEQ ID NO: 1 | 1.21 | 1.09 | 0.90 | 0.72 | 0.49 | 0.32 |
| SEQ ID NO: 5 | −0.02 | −0.02 | 0.00 | −0.01 | 0.00 | −0.02 |

ND: not determined due to low concentration of enzyme stock solution

The results show that lysozymes SEQ ID NO: 1, 18, 21, 24, 27 and 30 have excellent lysozyme activity against the peptidoglycans found in the cell walls of Lactobacillus johnsonii, while no activity of the lysozyme with SEQ ID NO: 5 was shown towards this peptidoglycan.

Example 9 Method for the Determination of Lysozyme Activity Against Lactobacillus johnsonii (B)

PGN Extraction:

Cultivation of Lactobacillus johnsonii:

Materials

MRS broth, product number BD 288130, pH 6.3-6.7.
MRS agar plates, BD 288130; Agar Oxoid LP0011; pH 6.3-6.7.
0.9% NaCl, Merck 106404, Cas no. 7647145
jars, supplier Merck 116387, Anaerocult anaerobic jar 2.5 L
Anaerogen 2.5 L, ThermoScientific, catalogue no. AN0025A
Lactobacillus johnsonii, DSM10533

Procedure

L. johnsonii was streaked from freeze stock to MRS agar plate and incubated under anaerobic conditions for 2 days, anaerobic jar with Anaerogen 2.5 L, 30° C. Some colonies were inoculated into 500 mLMRS broth in a 500 mL blue cap bottle and placed in an anaerobic jar with Anaerogen 2.5 L for 72 hours at 30° C.

The culture was spun down (6000 rpm, 10 minutes) and the supernatant was poured off before another round of centrifugation was performed. The pellet was washed in 100 mL 0.9% NaCl and the suspension was mixed well and centrifuged at 6000 rpm for 10 minutes. The supernatant was poured off and the washing procedure in 0.9% NaCl was repeated to a total of three washes. Approximately 40 mL 0.9% NaCl was added to the pellet and the solution was transferred to a 50 mL falcon tube. The solution was centrifuged at 6000 rpm for 10 minutes and the supernatant was poured off. The pellet was stored at −18° C. until the extraction of the peptidoglycan was conducted.

Extraction Procedure:

Materials

Protease from Streptomyces griseus, Sigma-Aldrich P5147, CAS 9036-06-0

PBS pH 7.3:
  NaCl: 8 g, Sigma-Aldrich 31434, CAS 7647-14-5
  KCl: 0.2 g, Sigma-Aldrich P9333, CAS 7447-40-7
  $KH_2PO_4$: 0.24 g, Sigma-Aldrich P5655, CAS 7778-77-0
  $Na_2HPO_4$. 2 $H_2O$: 1.44 g, Sigma-Aldrich 30412, CAS 10028-24-7
  Add Milli-Q water to 1000 mL 1% Triton-X 100 solution:
  1 mL Triton X100, Sigma-Aldrich X100, CAS 9002-93-1
  Add Milli Q water to 100 mL 500 mM sodium carbonate buffer, pH 9.3:
  500 mM sodium carbonate is made from 21 g $Na_2CO_3$ (Sigma-Aldrich S7795, CAS 497-19-8) in 500 mL MQ water 500 mM sodium bicarbonate is made from 72 g NaHCO$_3$ (Sigma-Aldrich S6014, CAS 144-55-8) in 500 mL MW water The pH 9.3 buffer is made from 320 mL NaHCO$_3$ and 80 mL Na$_2$CO$_3$ and adjusting pH with HCl Phenol solution with 10 mM Tris HCl, pH 8.0, 1 mM EDTA, Sigma-Aldrich P4557, CAS 108-95-2

Acetone, Sigma-Aldrich 32201-M, CAS 67-64-1

Ethanol, 96%, CCS Healthcare 1680643, CAS 64-17-5

Procedure

L. johnsonii cell material was freeze dried. The freeze dried material (525 mg) was suspended in PBS (40 mL) in a 50 mL Falcon tube. The suspension was shaken for 2 h @ 700 rpm in a thermoshaker at room temperature. Streptomyces griseus protease (55 mg) was then added and the suspension was incubated 6 h @ 37 C in the thermoshaker. It was then centrifuged 20 min @ 1900 g at room temperature, and the supernatant was decanted. The pellet was re-suspended in 1% Triton X-100 (40 mL) and shaken overnight @ 37 C. After another centrifugation and decantation, the pellet was re-suspended in PBS (40 mL) and protease (55 mg) added again. The suspension was again incubated 6 h @ 37 C, centrifuged and decanted. The pellet was re-suspended in PBS (40 mL) and shaken overnight @ 37 C. This washing procedure was repeated once more with PBS (40 mL, 30 min agitation), then with 50% ethanol/water (40 mL, 30 min agitation). The pellet was then split into two Falcon tubes. To each tube was added phenol solution (15 mL) pre-heated to 40 C. The suspensions were shaken 10 min @ 40 C, and then added 96% ethanol (25 mL to each tube), centrifuged and decanted. The pellets were further washed with acetone (40 mL in each tube) and 96% ethanol (40 mL in each tube), before being freeze dried. Combining the pellets from the two tubes yielded 80 mg purified peptidoglycan as a white powder.

Reducing End Assay

The lysozyme was diluted in phosphate dilution buffer (5 mM citrate, 5 mM K$_2$HPO$_4$, 0.01% TritonX-100, pH 5.0) to 200 µg/mL in polypropylene tubes. The diluted lysozyme was further diluted in a 96-well polypropylene microtiter plate by preparing a two-fold dilution series down to a concentration of 6.3 µg/mL in phosphate dilution buffer (5 mM citrate, 5 mM K$_2$HPO$_4$, 0.01% TritonX-100, pH 5.0). A 50 mg/ml stock solution of L. johnsonii substrate in MilIQ was prepared and diluted in phosphate buffer (50 mM citrate, 50 mM K$_2$HPO$_4$, pH 5.0) to 250 µg/ml. In a polypropylene deepwell plate 50 µL of the lysozyme dilution was mixed with 450 µL L. johnsonii solution and incubated at 40° C. with shaking (500 rpm) for 45 min. After incubation, the deepwell plate was centrifuged (3200 rpm, 7 min) to pellet insoluble material and 100 µL of the supernatant was mixed with 50 µL 3.2M HCl in a 96-well PCR plate and incubated at 95° C. for 80 min. 50 µL of 3.5 M NaOH was added to each well of the PCR plate, and 150 µL of each sample was transferred to a new PCR plate containing 75 µL/well 4-hydroxybenzhydrazide (PAHBAH) solution in K-Na tartrate/NaOH buffer (50 g/L K-Na tartrate+20 g/L NaOH). The plate was incubated at 95° C. for 10 min before 100 µL/sample was transferred to a clear flat-bottomed microtiter plate for optical density (OD) measurement at 405 nm. OD measurements were performed on three times diluted samples (50 µL sample diluted in 100 µL in Milli-Q water). The OD measurement values represent the difference after the original (background) reading was subtracted and represent the average of two OD measurement values.

Results are shown in Table 4.

TABLE 4

| Average OD405 measurements (background corrected) in Reducing End Assay | | | | | | |
|---|---|---|---|---|---|---|
| | Concentration of lysozyme in µg/mL | | | | | |
| Lysozyme | 20 | 10 | 5 | 2.5 | 1.25 | 0.63 |
| SEQ ID NO: 1 | 1.26 | 1.18 | 0.97 | 0.63 | 0.40 | 0.37 |
| SEQ ID NO: 15 | 0.98 | 0.67 | 0.47 | 0.37 | 0.21 | 0.15 |
| SEQ ID NO: 5 | −0.01 | −0.01 | 0.01 | −0.00 | 0.01 | −0.01 |

The results illustrate that two lysozymes (SEQ ID NO: 1 and 15) have excellent lysozyme activity against the peptidoglycans found in the cell walls of *Lactobacillus johnsonii*, while no activity of the lysozyme with SEQ ID NO: 5 was shown towards this peptidoglycan.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A method of stopping, hindering, alleviating or treating Irritable Bowel Syndrome (IBS) or Inflammatory Bowel Disease (IBD), the method comprising administering to a human a composition comprising a microbial lysozyme, wherein the microbial lysozyme has activity against *Lactobacillus johnsonii*, and wherein the method reduces the amount of dead *Lactobacillus johnsonii* cells in the digestive tract of said human.

2. The method of claim 1, wherein the microbial lysozyme stabilizes the healthy microbiota in the GI tract of the human and suppresses growth and/or intestinal colonization of bacterial pathogens in the human.

3. The method of claim 1, wherein the composition comprising the microbial lysozyme is administered at a level of 0.1 ppm to 1000 ppm enzyme protein per kg of said composition.

4. The method of claim 1, wherein the composition comprising the lysozyme is administered at a level of 1 to 200 mg enzyme protein per kg bodyweight of said human.

5. The method of claim 1, wherein the microbial lysozyme comprises one or more domains selected from a GH24 domain and a GH25 domain.

6. The method of claim 1, wherein the microbial lysozyme is selected from at least one of:
 (a) a polypeptide having at least 50% sequence identity to SEQ ID NO: 1;
 (b) a variant of SEQ ID NO: 1 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13 ,14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
 (c) a fragment of the polypeptide of (a) or (b) that has lysozyme activity wherein the fragment comprises at least 170 amino acids;
 (d) a polypeptide having at least 50% sequence identity to SEQ ID NO: 4;
 (e) a variant of SEQ ID NO: 4 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13 ,14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
 (f) a fragment of the polypeptide of (d) or (e) that has lysozyme activity wherein the fragment comprises at least 210 amino acids;
 (g) a polypeptide having at least 50% sequence identity to SEQ ID NO: 15;
 (h) a variant of SEQ ID NO: 15 wherein the variant has lysozyme activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13 ,14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(i) a fragment of the polypeptide of (g) or (h) that has lysozyme activity wherein the fragment comprises at least 170 amino acids;
and combinations thereof.

7. The method of claim 1, wherein the microbial lysozyme comprises an amino acid sequence selected from amino acids 1 to 208 of SEQ ID NO: 1, amino acids 1 to 245 of SEQ ID NO: 4, and amino acids 1 to 207 of SEQ ID NO: 15.

8. The method of claim 1, wherein the composition comprising the microbial lysozyme is a food composition or pharmaceutical composition.

9. The method of claim 1, wherein the composition comprising the microbial lysozyme is in the form of a powder, tablet, lozenge, effervescent tablet, capsule, emulsion, paste, individual sachet, chewing gum or oil drops.

10. The method of claim 1, wherein the Irritable Bowel Syndrome (IBS) or Inflammatory Bowel Disease (IBD) is Crohn's disease and/or Ulcerative colitis.

11. The method of claim 1, wherein said administering the composition comprising the microbial lysozyme increases the proportion of bacteria of genus *Faecalibacterium* in the microbiota of the GI tract.

12. The method of claim 1, wherein the microbial lysozyme is a polypeptide having at least 90% sequence identity to the polypeptide of SEQ ID NO: 1.

13. The method of claim 1, wherein the microbial lysozyme is a polypeptide having at least 90% sequence identity to the polypeptide of SEQ ID NO: 4.

14. The method of claim 1, wherein the microbial lysozyme is a polypeptide having at least 90% sequence identity to the polypeptide of SEQ ID NO: 15.

15. The method of claim 1, wherein the microbial lysozyme has a lysozyme activity against *Lactobacillus johnsonii* at 5 ppm that increases optical density (OD) measurement at 405 nm of at least 0.20 as determined by Method for the Determination of Lysozyme Activity Against *Lactobacillus johnsonii*.

* * * * *

SEQUENCE LISTING

```
<160> NUMBER OF SEQ ID NOS: 30

<210> SEQ ID NO 1
<211> LENGTH: 208
<212> TYPE: PRT
<213> ORGANISM: Acremonium alcalophilum
<220> FEATURE:
<221> NAME/KEY: mat_peptide
<222> LOCATION: (1)..(208)

<400> SEQUENCE: 1

Arg Ile Pro Gly Phe Asp Ile Ser Gly Trp Gln Pro Thr Thr Asp Phe
1               5                   10                  15

Ala Arg Ala Tyr Ala Asn Gly Asp Arg Phe Val Tyr Ile Lys Ala Thr
            20                  25                  30
```

```
Glu Gly Thr Thr Phe Lys Ser Ser Ala Phe Ser Arg Gln Tyr Thr Gly
             35                  40                  45

Ala Thr Gln Asn Gly Phe Ile Arg Gly Ala Tyr His Phe Ala Gln Pro
 50                  55                  60

Ala Ala Ser Ser Gly Ala Ala Gln Ala Arg Tyr Phe Ala Ser Asn Gly
 65                  70                  75                  80

Gly Gly Trp Ser Lys Asp Gly Ile Thr Leu Pro Gly Ala Leu Asp Ile
                 85                  90                  95

Glu Tyr Asn Pro Asn Gly Ala Thr Cys Tyr Gly Leu Ser Gln Ser Ala
                100                 105                 110

Met Val Asn Trp Ile Glu Asp Phe Val Thr Thr Tyr His Gly Ile Thr
            115                 120                 125

Ser Arg Trp Pro Val Ile Tyr Thr Thr Thr Asp Trp Thr Gln Cys
        130                 135                 140

Thr Gly Asn Ser Asn Arg Phe Ala Asn Arg Cys Pro Leu Trp Ile Ala
145                 150                 155                 160

Arg Tyr Ala Ser Ser Val Gly Thr Leu Pro Asn Gly Trp Gly Phe Tyr
                165                 170                 175

Thr Phe Trp Gln Tyr Asn Asp Lys Tyr Pro Gln Gly Gly Asp Ser Asn
            180                 185                 190

Trp Phe Asn Gly Asp Ala Ser Arg Leu Arg Ala Leu Ala Asn Gly Asp
        195                 200                 205

<210> SEQ ID NO 2
<211> LENGTH: 946
<212> TYPE: DNA
<213> ORGANISM: Trichophaea saccata
<220> FEATURE:
<221> NAME/KEY: CDS
<222> LOCATION: (1)..(347)
<220> FEATURE:
<221> NAME/KEY: sig_peptide
<222> LOCATION: (1)..(51)
<220> FEATURE:
<221> NAME/KEY: mat_peptide
<222> LOCATION: (52)..(943)
<220> FEATURE:
<221> NAME/KEY: CDS
<222> LOCATION: (401)..(615)
<220> FEATURE:
<221> NAME/KEY: CDS
<222> LOCATION: (668)..(772)
<220> FEATURE:
<221> NAME/KEY: CDS
<222> LOCATION: (825)..(943)

<400> SEQUENCE: 2 atg cac gct ctc acc ctt ctc acc gca acc ctc ttc ggt ctc gca gcg    48
Met His Ala Leu Thr Leu Leu Thr Ala Thr Leu Phe Gly Leu Ala Ala
        -15                 -10                  -5 gcc tac cca gtg aag acc gac ctt cac tgc cgc tcc tct ccc agc act    96
Ala Tyr Pro Val Lys Thr Asp Leu His Cys Arg Ser Ser Pro Ser Thr
 -1  1               5                  10                  15 tcc gcc agc atc gtc cgc acc tac tcc agt gga acg gaa gtc cag atc   144
Ser Ala Ser Ile Val Arg Thr Tyr Ser Ser Gly Thr Glu Val Gln Ile
                 20                  25                  30 cag tgc cag acc acg ggc act tcg gtc caa gga tcc aat gtc tgg gac   192
Gln Cys Gln Thr Thr Gly Thr Ser Val Gln Gly Ser Asn Val Trp Asp
             35                  40                  45 aag acc cag cac ggt tgc tac gtc gca gac tac tac gtc aag acc ggg   240
Lys Thr Gln His Gly Cys Tyr Val Ala Asp Tyr Tyr Val Lys Thr Gly
         50                  55                  60
```

| | |
|---|---|
| cat tct ggg att ttc acc acc aag tgc ggt agc agc tcg ggt gga ggt<br>His Ser Gly Ile Phe Thr Thr Lys Cys Gly Ser Ser Ser Gly Gly Gly<br>65                         70                       75 | 288 |
| tcc tgc aag cct ccc ccg atc aat gct gct act gtc gca ttg atc aag<br>Ser Cys Lys Pro Pro Pro Ile Asn Ala Ala Thr Val Ala Leu Ile Lys<br>80                         85                     90                 95 | 336 |
| gag ttt gag gg   gtaagtgaca gctctgagtg aggtggtatg aggattaaga<br>Glu Phe Glu Gly | 387 |
| ctgacgagga tag a ttc gtt cct aag ccc gcc ccg gat cct att gga ttg<br>                      Phe Val Pro Lys Pro Ala Pro Asp Pro Ile Gly Leu<br>                            100                105               110 | 437 |
| ccg acc gtg gga tac ggg cat ctt tgc aag act aag ggc tgc aaa gaa<br>Pro Thr Val Gly Tyr Gly His Leu Cys Lys Thr Lys Gly Cys Lys Glu<br>               115                    120                125 | 485 |
| gtg cct tac agc ttc cct ctc acc cag gag act gcc acc aag ttg ctt<br>Val Pro Tyr Ser Phe Pro Leu Thr Gln Glu Thr Ala Thr Lys Leu Leu<br>           130                    135                140 | 533 |
| cag agc gat atc aag act ttc acc tct tgc gtt agc aac tac gtc aag<br>Gln Ser Asp Ile Lys Thr Phe Thr Ser Cys Val Ser Asn Tyr Val Lys<br>145                       150                    155 | 581 |
| gac tct gtt aag ctc aac gat aac cag tac gga g   gtgagttcca<br>Asp Ser Val Lys Leu Asn Asp Asn Gln Tyr Gly<br>160                     165                    170 | 625 |
| gtgtaacagt gaatttattg atgatattct aagtaatttt ag ct   ctg gcg tct<br>                                                                               Ala Leu Ala Ser | 678 |
| tgg gct ttc aac gtc ggc tgc gga aac gtc cag act tct tcg ctg atc<br>Trp Ala Phe Asn Val Gly Cys Gly Asn Val Gln Thr Ser Ser Leu Ile<br>175                       180                    185                190 | 726 |
| aag aga ttg aac gct ggg gag aac cct aac act gtc gct gct cag g<br>Lys Arg Leu Asn Ala Gly Glu Asn Pro Asn Thr Val Ala Ala Gln<br>               195                    200                205 | 772 |
| gtaagatatt tatcccggat ttgctcttga cacatggctg aaaaagttgc ag aa   ctc<br>                                                                                Glu Leu | 829 |
| ccc aag tgg aag tac gct ggt gga aag gtt atg cct ggc ttg gtc cgc<br>Pro Lys Trp Lys Tyr Ala Gly Gly Lys Val Met Pro Gly Leu Val Arg<br>           210                    215                    220 | 877 |
| cgc cgc aat gct gag gtc gcg ctc ttc aag aag ccc agc agc gtt cag<br>Arg Arg Asn Ala Glu Val Ala Leu Phe Lys Lys Pro Ser Ser Val Gln<br>225                       230                    235 | 925 |
| gcc cac cct ccc aag tgc taa<br>Ala His Pro Pro Lys Cys<br>240                     245 | 946 |

<210> SEQ ID NO 3
<211> LENGTH: 262
<212> TYPE: PRT
<213> ORGANISM: Trichophaea saccata

<400> SEQUENCE: 3

Met His Ala Leu Thr Leu Leu Thr Ala Thr Leu Phe Gly Leu Ala Ala
         -15                  -10                  -5

Ala Tyr Pro Val Lys Thr Asp Leu His Cys Arg Ser Ser Pro Ser Thr
-1  1              5                   10                  15

Ser Ala Ser Ile Val Arg Thr Tyr Ser Ser Gly Thr Glu Val Gln Ile
          20                  25                  30

Gln Cys Gln Thr Thr Gly Thr Ser Val Gln Gly Ser Asn Val Trp Asp
          35                  40                  45

Lys Thr Gln His Gly Cys Tyr Val Ala Asp Tyr Tyr Val Lys Thr Gly
          50                  55                  60

```
His Ser Gly Ile Phe Thr Thr Lys Cys Gly Ser Ser Ser Gly Gly Gly
 65                  70                  75

Ser Cys Lys Pro Pro Pro Ile Asn Ala Ala Thr Val Ala Leu Ile Lys
 80                  85                  90                  95

Glu Phe Glu Gly Phe Val Pro Lys Pro Ala Pro Asp Pro Ile Gly Leu
                100                 105                 110

Pro Thr Val Gly Tyr Gly His Leu Cys Lys Thr Lys Gly Cys Lys Glu
            115                 120                 125

Val Pro Tyr Ser Phe Pro Leu Thr Gln Glu Thr Ala Thr Lys Leu Leu
        130                 135                 140

Gln Ser Asp Ile Lys Thr Phe Thr Ser Cys Val Ser Asn Tyr Val Lys
145                 150                 155

Asp Ser Val Lys Leu Asn Asp Asn Gln Tyr Gly Ala Leu Ala Ser Trp
160                 165                 170                 175

Ala Phe Asn Val Gly Cys Gly Asn Val Gln Thr Ser Ser Leu Ile Lys
                180                 185                 190

Arg Leu Asn Ala Gly Glu Asn Pro Asn Thr Val Ala Ala Gln Glu Leu
            195                 200                 205

Pro Lys Trp Lys Tyr Ala Gly Gly Lys Val Met Pro Gly Leu Val Arg
        210                 215                 220

Arg Arg Asn Ala Glu Val Ala Leu Phe Lys Lys Pro Ser Ser Val Gln
225                 230                 235

Ala His Pro Pro Lys Cys
240                 245

<210> SEQ ID NO 4
<211> LENGTH: 245
<212> TYPE: PRT
<213> ORGANISM: Trichophaea saccata
<220> FEATURE:
<221> NAME/KEY: mat_peptide
<222> LOCATION: (1)..(245)

<400> SEQUENCE: 4

Tyr Pro Val Lys Thr Asp Leu His Cys Arg Ser Ser Pro Ser Thr Ser
 1               5                  10                  15

Ala Ser Ile Val Arg Thr Tyr Ser Ser Gly Thr Glu Val Gln Ile Gln
                20                  25                  30

Cys Gln Thr Thr Gly Thr Ser Val Gln Gly Ser Asn Val Trp Asp Lys
            35                  40                  45

Thr Gln His Gly Cys Tyr Val Ala Asp Tyr Tyr Val Lys Thr Gly His
        50                  55                  60

Ser Gly Ile Phe Thr Thr Lys Cys Gly Ser Ser Ser Gly Gly Gly Ser
 65                  70                  75                  80

Cys Lys Pro Pro Pro Ile Asn Ala Ala Thr Val Ala Leu Ile Lys Glu
                85                  90                  95

Phe Glu Gly Phe Val Pro Lys Pro Ala Pro Asp Pro Ile Gly Leu Pro
            100                 105                 110

Thr Val Gly Tyr Gly His Leu Cys Lys Thr Lys Gly Cys Lys Glu Val
        115                 120                 125

Pro Tyr Ser Phe Pro Leu Thr Gln Glu Thr Ala Thr Lys Leu Leu Gln
    130                 135                 140

Ser Asp Ile Lys Thr Phe Thr Ser Cys Val Ser Asn Tyr Val Lys Asp
145                 150                 155                 160

Ser Val Lys Leu Asn Asp Asn Gln Tyr Gly Ala Leu Ala Ser Trp Ala
                165                 170                 175
```

```
Phe Asn Val Gly Cys Gly Asn Val Gln Thr Ser Ser Leu Ile Lys Arg
                180                 185                 190

Leu Asn Ala Gly Glu Asn Pro Asn Thr Val Ala Ala Gln Glu Leu Pro
            195                 200                 205

Lys Trp Lys Tyr Ala Gly Gly Lys Val Met Pro Gly Leu Val Arg Arg
        210                 215                 220

Arg Asn Ala Glu Val Ala Leu Phe Lys Lys Pro Ser Ser Val Gln Ala
225                 230                 235                 240

His Pro Pro Lys Cys
                245

<210> SEQ ID NO 5
<211> LENGTH: 129
<212> TYPE: PRT
<213> ORGANISM: Gallus gallus

<400> SEQUENCE: 5

Lys Val Phe Gly Arg Cys Glu Leu Ala Ala Ala Met Lys Arg His Gly
1               5                   10                  15

Leu Asp Asn Tyr Arg Gly Tyr Ser Leu Gly Asn Trp Val Cys Ala Ala
            20                  25                  30

Lys Phe Glu Ser Asn Phe Asn Thr Gln Ala Thr Asn Arg Asn Thr Asp
        35                  40                  45

Gly Ser Thr Asp Tyr Gly Ile Leu Gln Ile Asn Ser Arg Trp Trp Cys
    50                  55                  60

Asn Asp Gly Arg Thr Pro Gly Ser Arg Asn Leu Cys Asn Ile Pro Cys
65                  70                  75                  80

Ser Ala Leu Leu Ser Ser Asp Ile Thr Ala Ser Val Asn Cys Ala Lys
                85                  90                  95

Lys Ile Val Ser Asp Gly Asn Gly Met Asn Ala Trp Val Ala Trp Arg
            100                 105                 110

Asn Arg Cys Lys Gly Thr Asp Val Gln Ala Trp Ile Arg Gly Cys Arg
        115                 120                 125

Leu

<210> SEQ ID NO 6
<211> LENGTH: 39
<212> TYPE: DNA
<213> ORGANISM: Artificial Sequence
<220> FEATURE:
<223> OTHER INFORMATION: Primer F-80470

<400> SEQUENCE: 6
acacaactgg ggatccacca tgcacgctct caccctttct                      39

<210> SEQ ID NO 7
<211> LENGTH: 38
<212> TYPE: DNA
<213> ORGANISM: Artificial Sequence
<220> FEATURE:
<223> OTHER INFORMATION: Primer R-80470.

<400> SEQUENCE: 7
ctagatctcg agaagctttt agcacttggg agggtggg                       38

<210> SEQ ID NO 8
<211> LENGTH: 20
<212> TYPE: DNA
<213> ORGANISM: Artificial Sequence
```

```
<220> FEATURE:
<223> OTHER INFORMATION: Primer 8643.

<400> SEQUENCE: 8
gcaagggatg ccatgcttgg                                                    20

<210> SEQ ID NO 9
<211> LENGTH: 19
<212> TYPE: DNA
<213> ORGANISM: Artificial Sequence
<220> FEATURE:
<223> OTHER INFORMATION: Primer 8654.

<400> SEQUENCE: 9
catataacca attgccctc                                                     19

<210> SEQ ID NO 10
<211> LENGTH: 20
<212> TYPE: DNA
<213> ORGANISM: Artificial Sequence
<220> FEATURE:
<223> OTHER INFORMATION: Forward primer 27F.

<400> SEQUENCE: 10
agagtttgat cctggctcag                                                    20

<210> SEQ ID NO 11
<211> LENGTH: 17
<212> TYPE: DNA
<213> ORGANISM: Artificial Sequence
<220> FEATURE:
<223> OTHER INFORMATION: Reverse primer 534R.

<400> SEQUENCE: 11
attaccgcgg ctgctgg                                                       17

<210> SEQ ID NO 12
<211> LENGTH: 1462
<212> TYPE: DNA
<213> ORGANISM: Faecalibacterium prausnitzii

<400> SEQUENCE: 12
gatcctggct caggcgaacg ctggcggcgc gcctaacaca tgcaagtcga acgagcgaga         60
gagagcttgc tttctcaagc gagtggcgaa cgggtgagta acgcgtgagg aacctgcctc        120
aaagaggggg acaacagttg gaaacgactg ctaataccgc ataagcccac gacccggcat        180
cgggtagagg gaaaaggagc aatccgcttt gagatggcct cgcgtccgat tagctagttg        240
gtgaggtaac ggcccaccaa ggcgacgatc ggtagccgga ctgagaggtt gaacggccac        300
attgggactg agacacggcc cagactccta cgggaggcag cagtggggaa tattgcacaa        360
tgggggaaac cctgatgcag cgacgccgcg tggaggaaga aggtcttcgg attgtaaact        420
cctgttgttg aggaagataa tgacggtact caacaaggaa gtgacggcta actacgtgcc        480
agcagccgcg gtaaaacgta ggtcacaagc gttgtccgga attactgggt gtaaagggag        540
cgcaggcggg aaggcaagtt ggaagtgaaa tccatgggct caacccatga actgctttca        600
aaactgtttt tcttgagtag tgcagaggta ggcggaattc ccggtgtagc ggtggaatgc        660
gtagatatcg ggaggaacac cagtggcgaa ggcggcctac tgggcaccaa ctgacgctga        720
ggctcgaaag tgtgggtagc aaacaggatt agataccctg gtagtccaca ctgtggccga        780
tgtttactag gtgttggagg attgaccccc tcagtgccgc agttaacaca ataagtaatc        840
```

-continued

```
cacctgggga gtacgaccgc aaggttgaaa ctcaaaggaa ttgacggggg cccgcacaag    900
cagtggagta tgtggtttaa ttcgacgcaa cgcgaagaac cttaccaagt cttgacatcc    960
tgcgacgcac atagaaatat gtgtttcctt cgggacgcag agacaggtgg tgcatggttg   1020
tcgtcagctc gtgtcgtgag atgttgggtt aagtcccgca acgagcgcaa cccttatggt   1080
cagttactac gcaagaggac tctggccaga ctgccgttga caaaacggag gaaggtgggg   1140
atgacgtcaa atcatcatgc cctttatgac ttgggctaca cacgtactac aatgcgtta    1200 aacaaagaga agcaagaccg cgaggtggag caaaactcag aaacaacgtc ccagttcgga   1260
ctgcaggctg caactcgcct gcacgaagtc ggaattgcta gtaatcgcag atcagcatgc   1320
tgcggtgaat acgttccgg gccttgtaca caccgcccgt cacaccatga gagccggggg    1380
gacccgaagt cggtagtcta accgcaagga ggacgccgcc aaggtaaaa ctggtgattg     1440 gggtgaagtc gtaacaaggt ac                                            1462
```

<210> SEQ ID NO 13
<211> LENGTH: 909
<212> TYPE: DNA
<213> ORGANISM: Myceliophthora fergusii
<220> FEATURE:
<221> NAME/KEY: CDS
<222> LOCATION: (1)..(144)
<220> FEATURE:
<221> NAME/KEY: sig_peptide
<222> LOCATION: (1)..(54)
<220> FEATURE:
<221> NAME/KEY: mat_peptide
<222> LOCATION: (55)..(906)
<220> FEATURE:
<221> NAME/KEY: CDS
<222> LOCATION: (376)..(906)

<400> SEQUENCE: 13

```
atg aaa gct gct ctc ctc gct acc gtc tcc gcc ctc gcg gcc ggc gtg       48
Met Lys Ala Ala Leu Leu Ala Thr Val Ser Ala Leu Ala Ala Gly Val
        -15                 -10                 -5 caa gcc gcc gtc caa ggc ttt gac att tcc cac tgg cag tcc agc gtg       96
Gln Ala Ala Val Gln Gly Phe Asp Ile Ser His Trp Gln Ser Ser Val
 -1   1               5                   10 gac ttt aag gcg gcc tac aac tcg ggc gcc cgc ttc gtc atc atc aag      144
Asp Phe Lys Ala Ala Tyr Asn Ser Gly Ala Arg Phe Val Ile Ile Lys
 15                  20                  25                  30 gtaggtatta aggcctctct gtcgagcgag gcggcgtgtt tcaaccatca ttggattctc    204
ctgccttaaa tttgctcccct ctgtccaaag aggaggaaag aggaggggag aataacggaa    264
gatgcataat gggcaaaaaa aaaagaaaa ccaagaaaaa aaaacactg ggaactactg      324 atgaatagtc tcgtgagaga gccgacgtgc taaccccaac acctctatta g gcg acc     381
                                                         Ala Thr gag ggc acg tcg ttc atc gac ccc aag ttc tcg tcg cac tac acg ggc      429
Glu Gly Thr Ser Phe Ile Asp Pro Lys Phe Ser Ser His Tyr Thr Gly
                35                  40                  45 gcg acc aac gcc ggc ttc atc cgg ggc gcg tac cac ttc gcg cac ccg      477
Ala Thr Asn Ala Gly Phe Ile Arg Gly Ala Tyr His Phe Ala His Pro
     50                  55                  60 ggc cag tcg tcg ggc gag gcg cag gcc gac tac ttc ctc gcg cac ggc      525
Gly Gln Ser Ser Gly Glu Ala Gln Ala Asp Tyr Phe Leu Ala His Gly
 65                  70                  75                  80 ggc ggc tgg acg ccc gac ggc atc acg ctg ccc ggc atg ctg gac ctc      573
Gly Gly Trp Thr Pro Asp Gly Ile Thr Leu Pro Gly Met Leu Asp Leu
                 85                  90                  95
```

```
gag gcc tac aac gcg ggc gag tgc tgg ggc ctg tcc cag agc gcc atg      621
Glu Ala Tyr Asn Ala Gly Glu Cys Trp Gly Leu Ser Gln Ser Ala Met
                100                 105                 110 gtc gcg tgg atc aag gcc ttc agc gac cgc tac cac gcc cgc acc ggc      669
Val Ala Trp Ile Lys Ala Phe Ser Asp Arg Tyr His Ala Arg Thr Gly
        115                 120                 125 gtg tac ccg atg ctc tac acc aac ctg tcg tgg tgg aag acc tgc acc      717
Val Tyr Pro Met Leu Tyr Thr Asn Leu Ser Trp Trp Lys Thr Cys Thr
    130                 135                 140 ggc aac tcc aag gcc ttc gtc aac acc aac ccg ctc gtc ctc gcc cgc      765
Gly Asn Ser Lys Ala Phe Val Asn Thr Asn Pro Leu Val Leu Ala Arg
145                 150                 155                 160 tgg gcc agc tcg ccc ggc gag atc ccc ggc ggc tgg ccg tgg cag acc      813
Trp Ala Ser Ser Pro Gly Glu Ile Pro Gly Gly Trp Pro Trp Gln Thr
                165                 170                 175 atc tgg cag aac tcg gac tcg tac cgc tac ggc ggc gac tcg gac atc      861
Ile Trp Gln Asn Ser Asp Ser Tyr Arg Tyr Gly Gly Asp Ser Asp Ile
        180                 185                 190 ttc aac ggc gac atg aac cag ctc agg agg ctg gcc acc gcc gcc taa      909
Phe Asn Gly Asp Met Asn Gln Leu Arg Arg Leu Ala Thr Ala Ala
    195                 200                 205

<210> SEQ ID NO 14
<211> LENGTH: 225
<212> TYPE: PRT
<213> ORGANISM: Myceliophthora fergusii

<400> SEQUENCE: 14

Met Lys Ala Ala Leu Leu Ala Thr Val Ser Ala Leu Ala Ala Gly Val
            -15                 -10                  -5

Gln Ala Ala Val Gln Gly Phe Asp Ile Ser His Trp Gln Ser Ser Val
 -1  1               5                  10

Asp Phe Lys Ala Ala Tyr Asn Ser Gly Ala Arg Phe Val Ile Ile Lys
 15                  20                  25                  30

Ala Thr Glu Gly Thr Ser Phe Ile Asp Pro Lys Phe Ser Ser His Tyr
                 35                  40                  45

Thr Gly Ala Thr Asn Ala Gly Phe Ile Arg Gly Ala Tyr His Phe Ala
             50                  55                  60

His Pro Gly Gln Ser Ser Gly Glu Ala Gln Ala Asp Tyr Phe Leu Ala
         65                  70                  75

His Gly Gly Gly Trp Thr Pro Asp Gly Ile Thr Leu Pro Gly Met Leu
     80                  85                  90

Asp Leu Glu Ala Tyr Asn Ala Gly Glu Cys Trp Gly Leu Ser Gln Ser
 95                 100                 105                 110

Ala Met Val Ala Trp Ile Lys Ala Phe Ser Asp Arg Tyr His Ala Arg
                115                 120                 125

Thr Gly Val Tyr Pro Met Leu Tyr Thr Asn Leu Ser Trp Trp Lys Thr
            130                 135                 140

Cys Thr Gly Asn Ser Lys Ala Phe Val Asn Thr Asn Pro Leu Val Leu
        145                 150                 155

Ala Arg Trp Ala Ser Ser Pro Gly Glu Ile Pro Gly Gly Trp Pro Trp
    160                 165                 170

Gln Thr Ile Trp Gln Asn Ser Asp Ser Tyr Arg Tyr Gly Gly Asp Ser
175                 180                 185                 190

Asp Ile Phe Asn Gly Asp Met Asn Gln Leu Arg Arg Leu Ala Thr Ala
                195                 200                 205

Ala
```

```
<210> SEQ ID NO 15
<211> LENGTH: 207
<212> TYPE: PRT
<213> ORGANISM: Myceliophthora fergusii
<220> FEATURE:
<221> NAME/KEY: mat_peptide
<222> LOCATION: (1)..(207)

<400> SEQUENCE: 15

Ala Val Gln Gly Phe Asp Ile Ser His Trp Gln Ser Ser Val Asp Phe
1               5                   10                  15

Lys Ala Ala Tyr Asn Ser Gly Ala Arg Phe Val Ile Ile Lys Ala Thr
            20                  25                  30

Glu Gly Thr Ser Phe Ile Asp Pro Lys Phe Ser Ser His Tyr Thr Gly
        35                  40                  45

Ala Thr Asn Ala Gly Phe Ile Arg Gly Ala Tyr His Phe Ala His Pro
    50                  55                  60

Gly Gln Ser Ser Gly Glu Ala Gln Ala Asp Tyr Phe Leu Ala His Gly
65                  70                  75                  80

Gly Gly Trp Thr Pro Asp Gly Ile Thr Leu Pro Gly Met Leu Asp Leu
                85                  90                  95

Glu Ala Tyr Asn Ala Gly Glu Cys Trp Gly Leu Ser Gln Ser Ala Met
            100                 105                 110

Val Ala Trp Ile Lys Ala Phe Ser Asp Arg Tyr His Ala Arg Thr Gly
        115                 120                 125

Val Tyr Pro Met Leu Tyr Thr Asn Leu Ser Trp Trp Lys Thr Cys Thr
    130                 135                 140

Gly Asn Ser Lys Ala Phe Val Asn Thr Asn Pro Leu Val Leu Ala Arg
145                 150                 155                 160

Trp Ala Ser Ser Pro Gly Glu Ile Pro Gly Gly Trp Pro Trp Gln Thr
                165                 170                 175

Ile Trp Gln Asn Ser Asp Ser Tyr Arg Tyr Gly Gly Asp Ser Asp Ile
            180                 185                 190

Phe Asn Gly Asp Met Asn Gln Leu Arg Arg Leu Ala Thr Ala Ala
        195                 200                 205

<210> SEQ ID NO 16
<211> LENGTH: 796
<212> TYPE: DNA
<213> ORGANISM: Lecanicillium sp. WMM742
<220> FEATURE:
<221> NAME/KEY: CDS
<222> LOCATION: (1)..(150)
<220> FEATURE:
<221> NAME/KEY: sig_peptide
<222> LOCATION: (1)..(60)
<220> FEATURE:
<221> NAME/KEY: mat_peptide
<222> LOCATION: (61)..(793)
<220> FEATURE:
<221> NAME/KEY: CDS
<222> LOCATION: (199)..(381)
<220> FEATURE:
<221> NAME/KEY: CDS
<222> LOCATION: (443)..(793)

<400> SEQUENCE: 16 atg aag tca ttc tca tcc att atc gcc ggc atc gcc ggc ctt gcc tct      48
Met Lys Ser Phe Ser Ser Ile Ile Ala Gly Ile Ala Gly Leu Ala Ser
-20             -15                 -10                 -5 gtc gct tct gcc acg gtg cag ggc ttc gat gtc tct ggc tac cag ccc      96
Val Ala Ser Ala Thr Val Gln Gly Phe Asp Val Ser Gly Tyr Gln Pro
        -1  1               5                   10
```

```
act gtc aac tgg ggt gcg gcc tac agc agc ggt gct cgc ttc gtc atg    144
Thr Val Asn Trp Gly Ala Ala Tyr Ser Ser Gly Ala Arg Phe Val Met
         15                  20                  25 atc aag gtatgctgca gcggacggtt cgaatcacag atgatgctga caggctag gcc    201
Ile Lys                                                      Ala
 30 acc gag gga act ggt tac atc tcg tcc agc ttc ggc tcg cag tac cct    249
Thr Glu Gly Thr Gly Tyr Ile Ser Ser Ser Phe Gly Ser Gln Tyr Pro
             35                  40                  45 ggt gcc acc aat gcg ggc ttt atc cgc ggc ggc tac cac ttt gcg ctg    297
Gly Ala Thr Asn Ala Gly Phe Ile Arg Gly Gly Tyr His Phe Ala Leu
         50                  55                  60 ccc gac cgg tcc tct ggc tcc gca cag gcc gac tac ttt ctg gcc cac    345
Pro Asp Arg Ser Ser Gly Ser Ala Gln Ala Asp Tyr Phe Leu Ala His
         65                  70                  75 ggc ggc ggc tgg agc ggc gat ggc atc act cta ccg gtaagtccca           391
Gly Gly Gly Trp Ser Gly Asp Gly Ile Thr Leu Pro
 80              85                  90 tcaccttcct tgaatcgaag cgccatggta gtgctagtct gacgcatcca g ggc atg    448
                                                        Gly Met ctg gac att gag tat aac ccg tac ggc gcc acc tgc tac ggc ctc tcg    496
Leu Asp Ile Glu Tyr Asn Pro Tyr Gly Ala Thr Cys Tyr Gly Leu Ser
         95                 100                 105 cag ggc gcc atg gtc aac tgg atc agc gac ttt gtc gag cac tac aag    544
Gln Gly Ala Met Val Asn Trp Ile Ser Asp Phe Val Glu His Tyr Lys
110                 115                 120                 125 gcc agg acg acg cag tac ccc atc atc tac acg acc gac tgg tgg        592
Ala Arg Thr Thr Gln Tyr Pro Ile Ile Tyr Thr Thr Asp Trp Trp
                130                 135                 140 aag acg tgc acg ggc aac agc cct gcc ttt ggc caa aag tgc ccg ctg    640
Lys Thr Cys Thr Gly Asn Ser Pro Ala Phe Gly Gln Lys Cys Pro Leu
             145                 150                 155 agc ctg gcc cgg tac tcg agc agc gtg ggc gag atc ccc aac ggc tgg    688
Ser Leu Ala Arg Tyr Ser Ser Ser Val Gly Glu Ile Pro Asn Gly Trp
         160                 165                 170 ccg ttc cag act ttc tgg cag aac agc gac aag tat gcg tac ggt ggc    736
Pro Phe Gln Thr Phe Trp Gln Asn Ser Asp Lys Tyr Ala Tyr Gly Gly
         175                 180                 185 gat tcg cag att ttc aac ggc gcg tac tct cag ctg cag aag att gct    784
Asp Ser Gln Ile Phe Asn Gly Ala Tyr Ser Gln Leu Gln Lys Ile Ala
190                 195                 200                 205 cgc ggt ggt tag                                                    796
Arg Gly Gly <210> SEQ ID NO 17
<211> LENGTH: 228
<212> TYPE: PRT
<213> ORGANISM: Lecanicillium sp. WMM742

<400> SEQUENCE: 17

Met Lys Ser Phe Ser Ser Ile Ile Ala Gly Ile Ala Gly Leu Ala Ser
-20             -15                 -10                  -5

Val Ala Ser Ala Thr Val Gln Gly Phe Asp Val Ser Gly Tyr Gln Pro
         -1  1              5                  10

Thr Val Asn Trp Gly Ala Ala Tyr Ser Ser Gly Ala Arg Phe Val Met
             15                  20                  25

Ile Lys Ala Thr Glu Gly Thr Gly Tyr Ile Ser Ser Ser Phe Gly Ser
 30                  35                  40
```

```
Gln Tyr Pro Gly Ala Thr Asn Ala Gly Phe Ile Arg Gly Gly Tyr His
 45                  50                  55                  60

Phe Ala Leu Pro Asp Arg Ser Ser Gly Ser Ala Gln Ala Asp Tyr Phe
                 65                  70                  75

Leu Ala His Gly Gly Gly Trp Ser Gly Asp Gly Ile Thr Leu Pro Gly
             80                  85                  90

Met Leu Asp Ile Glu Tyr Asn Pro Tyr Gly Ala Thr Cys Tyr Gly Leu
         95                 100                 105

Ser Gln Gly Ala Met Val Asn Trp Ile Ser Asp Phe Val Glu His Tyr
     110                 115                 120

Lys Ala Arg Thr Thr Gln Tyr Pro Ile Ile Tyr Thr Thr Thr Asp Trp
125                 130                 135                 140

Trp Lys Thr Cys Thr Gly Asn Ser Pro Ala Phe Gly Gln Lys Cys Pro
                145                 150                 155

Leu Ser Leu Ala Arg Tyr Ser Ser Val Gly Glu Ile Pro Asn Gly
                160                 165                 170

Trp Pro Phe Gln Thr Phe Trp Gln Asn Ser Asp Lys Tyr Ala Tyr Gly
            175                 180                 185

Gly Asp Ser Gln Ile Phe Asn Gly Ala Tyr Ser Gln Leu Gln Lys Ile
        190                 195                 200

Ala Arg Gly Gly
205

<210> SEQ ID NO 18
<211> LENGTH: 208
<212> TYPE: PRT
<213> ORGANISM: Lecanicillium sp. WMM742
<220> FEATURE:
<221> NAME/KEY: mat_peptide
<222> LOCATION: (1)..(208)

<400> SEQUENCE: 18

Thr Val Gln Gly Phe Asp Val Ser Gly Tyr Gln Pro Thr Val Asn Trp
  1               5                  10                  15

Gly Ala Ala Tyr Ser Ser Gly Ala Arg Phe Val Met Ile Lys Ala Thr
                 20                  25                  30

Glu Gly Thr Gly Tyr Ile Ser Ser Phe Gly Ser Gln Tyr Pro Gly
             35                  40                  45

Ala Thr Asn Ala Gly Phe Ile Arg Gly Gly Tyr His Phe Ala Leu Pro
 50                  55                  60

Asp Arg Ser Ser Gly Ser Ala Gln Ala Asp Tyr Phe Leu Ala His Gly
 65                  70                  75                  80

Gly Gly Trp Ser Gly Asp Gly Ile Thr Leu Pro Gly Met Leu Asp Ile
                 85                  90                  95

Glu Tyr Asn Pro Tyr Gly Ala Thr Cys Tyr Gly Leu Ser Gln Gly Ala
                100                 105                 110

Met Val Asn Trp Ile Ser Asp Phe Val Glu His Tyr Lys Ala Arg Thr
            115                 120                 125

Thr Gln Tyr Pro Ile Ile Tyr Thr Thr Thr Asp Trp Trp Lys Thr Cys
        130                 135                 140

Thr Gly Asn Ser Pro Ala Phe Gly Gln Lys Cys Pro Leu Ser Leu Ala
145                 150                 155                 160

Arg Tyr Ser Ser Val Gly Glu Ile Pro Asn Gly Trp Pro Phe Gln
                165                 170                 175
```

```
Thr Phe Trp Gln Asn Ser Asp Lys Tyr Ala Tyr Gly Gly Asp Ser Gln
        180                 185                 190

Ile Phe Asn Gly Ala Tyr Ser Gln Leu Gln Lys Ile Ala Arg Gly Gly
        195                 200                 205

<210> SEQ ID NO 19
<211> LENGTH: 684
<212> TYPE: DNA
<213> ORGANISM: Zygomycetes sp. XZ2655
<220> FEATURE:
<221> NAME/KEY: CDS
<222> LOCATION: (1)..(681)
<220> FEATURE:
<221> NAME/KEY: sig_peptide
<222> LOCATION: (1)..(57)
<220> FEATURE:
<221> NAME/KEY: mat_peptide
<222> LOCATION: (58)..(681)

<400> SEQUENCE: 19 atg aaa gca atc gta aca gca tta gca tta tcc ttg tta tgg gcg ggt    48
Met Lys Ala Ile Val Thr Ala Leu Ala Leu Ser Leu Leu Trp Ala Gly
        -15                 -10                  -5 gcc cat gca act ttg ccc ggc tta gac gtc agc agc tac caa ggt aac    96
Ala His Ala Thr Leu Pro Gly Leu Asp Val Ser Ser Tyr Gln Gly Asn
        -1   1               5                  10 gtc aat tgg gga aca gtg gcg agt caa gga gca aaa ttt gct tac gtc   144
Val Asn Trp Gly Thr Val Ala Ser Gln Gly Ala Lys Phe Ala Tyr Val
         15                  20                  25 aag gct acc gag ggt acg acc tac acg aat ccc tat ttt gcg tcc caa   192
Lys Ala Thr Glu Gly Thr Thr Tyr Thr Asn Pro Tyr Phe Ala Ser Gln
 30                  35                  40                  45 tac gac gga tcc tac aac gcg ggc cta att cgc ggt gcc tat cac ttt   240
Tyr Asp Gly Ser Tyr Asn Ala Gly Leu Ile Arg Gly Ala Tyr His Phe
                 50                  55                  60 gcc cat ccc gat tct tcc tct gga gct acc caa gca aac tat ttc ctt   288
Ala His Pro Asp Ser Ser Ser Gly Ala Thr Gln Ala Asn Tyr Phe Leu
             65                  70                  75 gct cat ggt ggc ggc tgg tcc gct gac gga aag acc tta cct ggt gcg   336
Ala His Gly Gly Gly Trp Ser Ala Asp Gly Lys Thr Leu Pro Gly Ala
         80                  85                  90 cta gat att gag tac aat cct aac ggc gct gaa tgc tac ggc ttg tct   384
Leu Asp Ile Glu Tyr Asn Pro Asn Gly Ala Glu Cys Tyr Gly Leu Ser
 95                 100                 105 caa ttg gcc atg att agc tgg att caa gac ttc agc aac acc tat cac   432
Gln Leu Ala Met Ile Ser Trp Ile Gln Asp Phe Ser Asn Thr Tyr His
110                 115                 120                 125 tcc cac acg ggc aga tat ccg gtc att tac acg act acg gac tgg tgg   480
Ser His Thr Gly Arg Tyr Pro Val Ile Tyr Thr Thr Thr Asp Trp Trp
                130                 135                 140 acc acc tgc acg ggt aac agc gca gcc ttt gga acc aac aac cct ctc   528
Thr Thr Cys Thr Gly Asn Ser Ala Ala Phe Gly Thr Asn Asn Pro Leu
            145                 150                 155 tgg att gct cgg tat tcg tct tcg gtg ggc acc ctg cct gca ggt tgg   576
Trp Ile Ala Arg Tyr Ser Ser Ser Val Gly Thr Leu Pro Ala Gly Trp
        160                 165                 170 ggc tac gag agc ttc tgg cag aag gca tct tcg ggt acg ttc cct gga   624
Gly Tyr Glu Ser Phe Trp Gln Lys Ala Ser Ser Gly Thr Phe Pro Gly
    175                 180                 185
```

```
gac caa gat atc tgg aat ggc gat gct gct gga ctc tcc aga ttc gcc    672
Asp Gln Asp Ile Trp Asn Gly Asp Ala Ala Gly Leu Ser Arg Phe Ala
190             195                 200                 205 acc ggc aaa tga                                                     684
Thr Gly Lys
```

<210> SEQ ID NO 20
<211> LENGTH: 227
<212> TYPE: PRT
<213> ORGANISM: Zygomycetes sp. XZ2655

<400> SEQUENCE: 20

```
Met Lys Ala Ile Val Thr Ala Leu Ala Leu Ser Leu Leu Trp Ala Gly
            -15                 -10                 -5

Ala His Ala Thr Leu Pro Gly Leu Asp Val Ser Ser Tyr Gln Gly Asn
        -1  1               5                   10

Val Asn Trp Gly Thr Val Ala Ser Gln Gly Ala Lys Phe Ala Tyr Val
        15                  20                  25

Lys Ala Thr Glu Gly Thr Thr Tyr Thr Asn Pro Tyr Phe Ala Ser Gln
30                  35                  40                  45

Tyr Asp Gly Ser Tyr Asn Ala Gly Leu Ile Arg Gly Ala Tyr His Phe
                50                  55                  60

Ala His Pro Asp Ser Ser Gly Ala Thr Gln Ala Asn Tyr Phe Leu
        65                  70                  75

Ala His Gly Gly Gly Trp Ser Ala Asp Gly Lys Thr Leu Pro Gly Ala
        80                  85                  90

Leu Asp Ile Glu Tyr Asn Pro Asn Gly Ala Glu Cys Tyr Gly Leu Ser
        95                  100                 105

Gln Leu Ala Met Ile Ser Trp Ile Gln Asp Phe Ser Asn Thr Tyr His
110                 115                 120                 125

Ser His Thr Gly Arg Tyr Pro Val Ile Tyr Thr Thr Asp Trp Trp
                130                 135                 140

Thr Thr Cys Thr Gly Asn Ser Ala Ala Phe Gly Thr Asn Asn Pro Leu
                145                 150                 155

Trp Ile Ala Arg Tyr Ser Ser Ser Val Gly Thr Leu Pro Ala Gly Trp
                160                 165                 170

Gly Tyr Glu Ser Phe Trp Gln Lys Ala Ser Ser Gly Thr Phe Pro Gly
        175                 180                 185

Asp Gln Asp Ile Trp Asn Gly Asp Ala Ala Gly Leu Ser Arg Phe Ala
190                 195                 200                 205

Thr Gly Lys
```

<210> SEQ ID NO 21
<211> LENGTH: 208
<212> TYPE: PRT
<213> ORGANISM: Zygomycetes sp. XZ2655
<220> FEATURE:
<221> NAME/KEY: mat_peptide
<222> LOCATION: (1)..(208)

<400> SEQUENCE: 21

```
Thr Leu Pro Gly Leu Asp Val Ser Ser Tyr Gln Gly Asn Val Asn Trp
1               5                   10                  15

Gly Thr Val Ala Ser Gln Gly Ala Lys Phe Ala Tyr Val Lys Ala Thr
            20                  25                  30

Glu Gly Thr Thr Tyr Thr Asn Pro Tyr Phe Ala Ser Gln Tyr Asp Gly
        35                  40                  45
```

```
Ser Tyr Asn Ala Gly Leu Ile Arg Gly Ala Tyr His Phe Ala His Pro
    50              55                  60
Asp Ser Ser Ser Gly Ala Thr Gln Ala Asn Tyr Phe Leu Ala His Gly
 65              70                  75                  80
Gly Gly Trp Ser Ala Asp Gly Lys Thr Leu Pro Gly Ala Leu Asp Ile
                 85                  90                  95
Glu Tyr Asn Pro Asn Gly Ala Glu Cys Tyr Gly Leu Ser Gln Leu Ala
                100                 105                 110
Met Ile Ser Trp Ile Gln Asp Phe Ser Asn Thr Tyr His Ser His Thr
            115                 120                 125
Gly Arg Tyr Pro Val Ile Tyr Thr Thr Thr Asp Trp Trp Thr Thr Cys
130                 135                 140
Thr Gly Asn Ser Ala Ala Phe Gly Thr Asn Asn Pro Leu Trp Ile Ala
145                 150                 155                 160
Arg Tyr Ser Ser Ser Val Gly Thr Leu Pro Ala Gly Trp Gly Tyr Glu
                165                 170                 175
Ser Phe Trp Gln Lys Ala Ser Gly Thr Phe Pro Gly Asp Gln Asp
            180                 185                 190
Ile Trp Asn Gly Asp Ala Ala Gly Leu Ser Arg Phe Ala Thr Gly Lys
        195                 200                 205

<210> SEQ ID NO 22
<211> LENGTH: 767
<212> TYPE: DNA
<213> ORGANISM: Malbranchea flava
<220> FEATURE:
<221> NAME/KEY: CDS
<222> LOCATION: (1)..(174)
<220> FEATURE:
<221> NAME/KEY: sig_peptide
<222> LOCATION: (1)..(54)
<220> FEATURE:
<221> NAME/KEY: mat_peptide
<222> LOCATION: (55)..(764)
<220> FEATURE:
<221> NAME/KEY: CDS
<222> LOCATION: (234)..(764)

<400> SEQUENCE: 22 atg aag ctg tct ctc ctc ctt att gtt gct gca tca ctg gcc gtg gcc     48
Met Lys Leu Ser Leu Leu Leu Ile Val Ala Ala Ser Leu Ala Val Ala
        -15                 -10                  -5 agt gca ggc ccc aag gag ttc gag tca cgc gcg tcg ggc gtc cag ggc     96
Ser Ala Gly Pro Lys Glu Phe Glu Ser Arg Ala Ser Gly Val Gln Gly
 -1  1               5                  10 ttt gac atc tct ggt tgg cag tcc aac gtc aat ttt gca ggt gca tac    144
Phe Asp Ile Ser Gly Trp Gln Ser Asn Val Asn Phe Ala Gly Ala Tyr
 15                  20                  25                  30 aat tct ggc gca cgc ttc gtc atg atc aag gtacatttga gtgaattcgt      194
Asn Ser Gly Ala Arg Phe Val Met Ile Lys
                 35                  40 ttctcctggt ataatacccct gactaatgta aagatccag gct agc gag ggt acc    248
                                            Ala Ser Glu Gly Thr
                                                             45 acc ttc aag gac cgt caa ttc agc aat cat tac att ggc gcc acc aag    296
Thr Phe Lys Asp Arg Gln Phe Ser Asn His Tyr Ile Gly Ala Thr Lys
                 50                  55                  60 gct ggc ttt atc cgt ggc ggc tac cac ttt gcg ttg cca gac gtc agc    344
Ala Gly Phe Ile Arg Gly Gly Tyr His Phe Ala Leu Pro Asp Val Ser
                 65                  70                  75
```

```
agc gcc act gcc caa gtg aac cat ttc ctg gcc agc ggt ggt ggc tgg    392
Ser Ala Thr Ala Gln Val Asn His Phe Leu Ala Ser Gly Gly Gly Trp
         80                  85                  90 agc aga gac ggc atc acg ctg ccg ggc atg ctg gac atc gag agc aac    440
Ser Arg Asp Gly Ile Thr Leu Pro Gly Met Leu Asp Ile Glu Ser Asn
     95                 100                 105 ccg tat ggc gcc cag tgc tac ggc ctt gac gct ggt cgt atg gtt gcc    488
Pro Tyr Gly Ala Gln Cys Tyr Gly Leu Asp Ala Gly Arg Met Val Ala
110                 115                 120                 125 tgg atc cgg gag ttt gtt gac gcg tac aag cgc gca act gga cgg tat    536
Trp Ile Arg Glu Phe Val Asp Ala Tyr Lys Arg Ala Thr Gly Arg Tyr
                130                 135                 140 cct ctg atc tac acg tct ccc agc tgg tgg cag act tgc acg ggc aat    584
Pro Leu Ile Tyr Thr Ser Pro Ser Trp Trp Gln Thr Cys Thr Gly Asn
            145                 150                 155 agc aat gcc ttt ata gac aag tgc ccg ctt gtg ttg gca cgg tgg gcg    632
Ser Asn Ala Phe Ile Asp Lys Cys Pro Leu Val Leu Ala Arg Trp Ala
        160                 165                 170 agt agc cct ggc act ccg cct ggt ggg tgg ccg ttc cac agt ttt tgg    680
Ser Ser Pro Gly Thr Pro Pro Gly Gly Trp Pro Phe His Ser Phe Trp
175                 180                 185 cag tac gcc gat tcc tat caa ttc ggt ggt gac gcc cag gta ttc aat    728
Gln Tyr Ala Asp Ser Tyr Gln Phe Gly Gly Asp Ala Gln Val Phe Asn
190                 195                 200                 205 ggc gat gag gct ggg ttg aag aga atg gcc cta ggt taa                767
Gly Asp Glu Ala Gly Leu Lys Arg Met Ala Leu Gly
                210                 215

<210> SEQ ID NO 23
<211> LENGTH: 235
<212> TYPE: PRT
<213> ORGANISM: Malbranchea flava

<400> SEQUENCE: 23

Met Lys Leu Ser Leu Leu Leu Ile Val Ala Ala Ser Leu Ala Val Ala
                -15                 -10                  -5

Ser Ala Gly Pro Lys Glu Phe Glu Ser Arg Ala Ser Gly Val Gln Gly
     -1   1               5                  10

Phe Asp Ile Ser Gly Trp Gln Ser Asn Val Asn Phe Ala Gly Ala Tyr
 15                  20                  25                  30

Asn Ser Gly Ala Arg Phe Val Met Ile Lys Ala Ser Glu Gly Thr Thr
                 35                  40                  45

Phe Lys Asp Arg Gln Phe Ser Asn His Tyr Ile Gly Ala Thr Lys Ala
             50                  55                  60

Gly Phe Ile Arg Gly Gly Tyr His Phe Ala Leu Pro Asp Val Ser Ser
         65                  70                  75

Ala Thr Ala Gln Val Asn His Phe Leu Ala Ser Gly Gly Gly Trp Ser
     80                  85                  90

Arg Asp Gly Ile Thr Leu Pro Gly Met Leu Asp Ile Glu Ser Asn Pro
 95                 100                 105                 110

Tyr Gly Ala Gln Cys Tyr Gly Leu Asp Ala Gly Arg Met Val Ala Trp
                115                 120                 125

Ile Arg Glu Phe Val Asp Ala Tyr Lys Arg Ala Thr Gly Arg Tyr Pro
            130                 135                 140

Leu Ile Tyr Thr Ser Pro Ser Trp Trp Gln Thr Cys Thr Gly Asn Ser
        145                 150                 155

Asn Ala Phe Ile Asp Lys Cys Pro Leu Val Leu Ala Arg Trp Ala Ser
    160                 165                 170
```

```
Ser Pro Gly Thr Pro Pro Gly Gly Trp Pro Phe His Ser Phe Trp Gln
175                 180                 185                 190

Tyr Ala Asp Ser Tyr Gln Phe Gly Gly Asp Ala Gln Val Phe Asn Gly
                195                 200                 205

Asp Glu Ala Gly Leu Lys Arg Met Ala Leu Gly
            210                 215

<210> SEQ ID NO 24
<211> LENGTH: 217
<212> TYPE: PRT
<213> ORGANISM: Malbranchea flava
<220> FEATURE:
<221> NAME/KEY: mat_peptide
<222> LOCATION: (1)..(217)

<400> SEQUENCE: 24

Gly Pro Lys Glu Phe Glu Ser Arg Ala Ser Gly Val Gln Gly Phe Asp
1               5                   10                  15

Ile Ser Gly Trp Gln Ser Asn Val Asn Phe Ala Gly Ala Tyr Asn Ser
                20                  25                  30

Gly Ala Arg Phe Val Met Ile Lys Ala Ser Glu Gly Thr Thr Phe Lys
            35                  40                  45

Asp Arg Gln Phe Ser Asn His Tyr Ile Gly Ala Thr Lys Ala Gly Phe
    50                  55                  60

Ile Arg Gly Gly Tyr His Phe Ala Leu Pro Asp Val Ser Ala Thr
65                  70                  75                  80

Ala Gln Val Asn His Phe Leu Ala Ser Gly Gly Trp Ser Arg Asp
                85                  90                  95

Gly Ile Thr Leu Pro Gly Met Leu Asp Ile Glu Ser Asn Pro Tyr Gly
            100                 105                 110

Ala Gln Cys Tyr Gly Leu Asp Ala Gly Arg Met Val Ala Trp Ile Arg
        115                 120                 125

Glu Phe Val Asp Ala Tyr Lys Arg Ala Thr Gly Arg Tyr Pro Leu Ile
130                 135                 140

Tyr Thr Ser Pro Ser Trp Trp Gln Thr Cys Thr Gly Asn Ser Asn Ala
145                 150                 155                 160

Phe Ile Asp Lys Cys Pro Leu Val Leu Ala Arg Trp Ala Ser Ser Pro
                165                 170                 175

Gly Thr Pro Pro Gly Gly Trp Pro Phe His Ser Phe Trp Gln Tyr Ala
            180                 185                 190

Asp Ser Tyr Gln Phe Gly Gly Asp Ala Gln Val Phe Asn Gly Asp Glu
        195                 200                 205

Ala Gly Leu Lys Arg Met Ala Leu Gly
    210                 215

<210> SEQ ID NO 25
<211> LENGTH: 687
<212> TYPE: DNA
<213> ORGANISM: Hypholoma polytrichi
<220> FEATURE:
<221> NAME/KEY: CDS
<222> LOCATION: (1)..(684)
<220> FEATURE:
<221> NAME/KEY: sig_peptide
<222> LOCATION: (1)..(60)
<220> FEATURE:
<221> NAME/KEY: mat_peptide
<222> LOCATION: (61)..(684)
```

<400> SEQUENCE: 25

```
atg gca aag ctc ctc aag cag ttg gtg ttg ctc ccg ttc ctc gcg ttg      48
Met Ala Lys Leu Leu Lys Gln Leu Val Leu Leu Pro Phe Leu Ala Leu
-20              -15                 -10                  -5 gca gca cac gca ttg gtc tac gga gtc gat tcg tcc tcg ttg gtc cct      96
Ala Ala His Ala Leu Val Tyr Gly Val Asp Ser Ser Ser Leu Val Pro
         -1  1                   5                  10 gtg gcg acg tat cag aag gca ttg gga gaa ggc ttc aca aag gcc gtc     144
Val Ala Thr Tyr Gln Lys Ala Leu Gly Glu Gly Phe Thr Lys Ala Val
         15                  20                  25 att agg ggc tac gaa gag gcc tgt gga gtc gga gga gag gtc gat ccc     192
Ile Arg Gly Tyr Glu Glu Ala Cys Gly Val Gly Gly Glu Val Asp Pro
         30                  35                  40 aac ttc gtc ccc tcc tac aaa aac gca cga gcg gca gga tac aca gac     240
Asn Phe Val Pro Ser Tyr Lys Asn Ala Arg Ala Ala Gly Tyr Thr Asp
45                  50                  55                  60 atc gat atg tac tgg ttc ccc tgt aac ggc tcc act cat tcg tgt aaa     288
Ile Asp Met Tyr Trp Phe Pro Cys Asn Gly Ser Thr His Ser Cys Lys
                 65                  70                  75 tcg tat gcc gca cag ttg gca gcc att gcc gca gcc ttc tcg gcg aac     336
Ser Tyr Ala Ala Gln Leu Ala Ala Ile Ala Ala Ala Phe Ser Ala Asn
             80                  85                  90 gcc atg aag atc ggt act att tgg atc gac atc gaa aaa gat gca gcc     384
Ala Met Lys Ile Gly Thr Ile Trp Ile Asp Ile Glu Lys Asp Ala Ala
         95                 100                 105 atc tgt aac aac tgg gat tac ggc act gca ggt aac ttg gcc cag gcg     432
Ile Cys Asn Asn Trp Asp Tyr Gly Thr Ala Gly Asn Leu Ala Gln Ala
     110                 115                 120 aag gca ttg att gcc gca gcg aag gca tcc ggt ttc aac ttc ggc atc     480
Lys Ala Leu Ile Ala Ala Ala Lys Ala Ser Gly Phe Asn Phe Gly Ile
125                 130                 135                 140 tac tcg tcg cct gga gag tgg tcg acc atc ttc ggc tcg acc tcg gtc     528
Tyr Ser Ser Pro Gly Glu Trp Ser Thr Ile Phe Gly Ser Thr Ser Val
                145                 150                 155 gtc gtc gac aac tcc gca ccg ctc tgg ttc gcg acc tat aac aac gtc     576
Val Val Asp Asn Ser Ala Pro Leu Trp Phe Ala Thr Tyr Asn Asn Val
            160                 165                 170 cag acc ctc acg ctc ggc act cct ttc gga ggc tgg tcg aca gcc gtc     624
Gln Thr Leu Thr Leu Gly Thr Pro Phe Gly Gly Trp Ser Thr Ala Val
        175                 180                 185 ggt cat cag tat acc gat gtg tcc gcc tcc gga ctc ttc gac ctc aac     672
Gly His Gln Tyr Thr Asp Val Ser Ala Ser Gly Leu Phe Asp Leu Asn
    190                 195                 200 gtc ttc gcc cac taa                                                  687
Val Phe Ala His
205
```

<210> SEQ ID NO 26
<211> LENGTH: 228
<212> TYPE: PRT
<213> ORGANISM: Hypholoma polytrichi

<400> SEQUENCE: 26

```
Met Ala Lys Leu Leu Lys Gln Leu Val Leu Leu Pro Phe Leu Ala Leu
-20              -15                 -10                  -5

Ala Ala His Ala Leu Val Tyr Gly Val Asp Ser Ser Ser Leu Val Pro
         -1  1                   5                  10

Val Ala Thr Tyr Gln Lys Ala Leu Gly Glu Gly Phe Thr Lys Ala Val
         15                  20                  25
```

Ile Arg Gly Tyr Glu Glu Ala Cys Gly Val Gly Glu Val Asp Pro
    30                  35                  40

Asn Phe Val Pro Ser Tyr Lys Asn Ala Arg Ala Ala Gly Tyr Thr Asp
45                  50                  55                  60

Ile Asp Met Tyr Trp Phe Pro Cys Asn Gly Ser Thr His Ser Cys Lys
                65                  70                  75

Ser Tyr Ala Ala Gln Leu Ala Ala Ile Ala Ala Phe Ser Ala Asn
            80                  85                  90

Ala Met Lys Ile Gly Thr Ile Trp Ile Asp Ile Glu Lys Asp Ala Ala
            95                  100                 105

Ile Cys Asn Asn Trp Asp Tyr Gly Thr Ala Gly Asn Leu Ala Gln Ala
110                 115                 120

Lys Ala Leu Ile Ala Ala Lys Ala Ser Gly Phe Asn Phe Gly Ile
125                 130                 135                 140

Tyr Ser Ser Pro Gly Glu Trp Ser Thr Ile Phe Gly Ser Thr Ser Val
                145                 150                 155

Val Val Asp Asn Ser Ala Pro Leu Trp Phe Ala Thr Tyr Asn Asn Val
            160                 165                 170

Gln Thr Leu Thr Leu Gly Thr Pro Phe Gly Gly Trp Ser Thr Ala Val
            175                 180                 185

Gly His Gln Tyr Thr Asp Val Ser Ala Ser Gly Leu Phe Asp Leu Asn
190                 195                 200

Val Phe Ala His
205

<210> SEQ ID NO 27
<211> LENGTH: 208
<212> TYPE: PRT
<213> ORGANISM: Hypholoma polytrichid
<220> FEATURE:
<221> NAME/KEY: mat_peptide
<222> LOCATION: (1)..(208)

<400> SEQUENCE: 27

Leu Val Tyr Gly Val Asp Ser Ser Leu Val Pro Val Ala Thr Tyr
1               5                   10                  15

Gln Lys Ala Leu Gly Glu Gly Phe Thr Lys Ala Val Ile Arg Gly Tyr
                20                  25                  30

Glu Glu Ala Cys Gly Val Gly Gly Glu Val Asp Pro Asn Phe Val Pro
            35                  40                  45

Ser Tyr Lys Asn Ala Arg Ala Ala Gly Tyr Thr Asp Ile Asp Met Tyr
50                  55                  60

Trp Phe Pro Cys Asn Gly Ser Thr His Ser Cys Lys Ser Tyr Ala Ala
65                  70                  75                  80

Gln Leu Ala Ala Ile Ala Ala Phe Ser Ala Asn Ala Met Lys Ile
            85                  90                  95

Gly Thr Ile Trp Ile Asp Ile Glu Lys Asp Ala Ala Ile Cys Asn Asn
                100                 105                 110

Trp Asp Tyr Gly Thr Ala Gly Asn Leu Ala Gln Ala Lys Ala Leu Ile
            115                 120                 125

Ala Ala Ala Lys Ala Ser Gly Phe Asn Phe Gly Ile Tyr Ser Ser Pro
130                 135                 140

Gly Glu Trp Ser Thr Ile Phe Gly Ser Thr Ser Val Val Val Asp Asn
145                 150                 155                 160

Ser Ala Pro Leu Trp Phe Ala Thr Tyr Asn Asn Val Gln Thr Leu Thr
                165                 170                 175

```
Leu Gly Thr Pro Phe Gly Gly Trp Ser Thr Ala Val Gly His Gln Tyr
        180                 185                 190

Thr Asp Val Ser Ala Ser Gly Leu Phe Asp Leu Asn Val Phe Ala His
        195                 200                 205

<210> SEQ ID NO 28
<211> LENGTH: 782
<212> TYPE: DNA
<213> ORGANISM: Engyodontium album
<220> FEATURE:
<221> NAME/KEY: CDS
<222> LOCATION: (1)..(150)
<220> FEATURE:
<221> NAME/KEY: sig_peptide
<222> LOCATION: (1)..(60)
<220> FEATURE:
<221> NAME/KEY: mat_peptide
<222> LOCATION: (61)..(779)
<220> FEATURE:
<221> NAME/KEY: CDS
<222> LOCATION: (200)..(383)
<220> FEATURE:
<221> NAME/KEY: CDS
<222> LOCATION: (433)..(779)

<400> SEQUENCE: 28 atg aag tct ttt ggt gtt att gct acc ggt ttg gcc acc ctt gtg ggt     48
Met Lys Ser Phe Gly Val Ile Ala Thr Gly Leu Ala Thr Leu Val Gly
-20             -15                 -10                 -5 gtt gcc tct gcc aga gtc caa ggt ttc gac atc tcc cac tat cag ccc     96
Val Ala Ser Ala Arg Val Gln Gly Phe Asp Ile Ser His Tyr Gln Pro
            -1  1               5                   10 agc gtc gac ttc aat gcg gcc tat gct gac gga gct cgc ttt gtg atc    144
Ser Val Asp Phe Asn Ala Ala Tyr Ala Asp Gly Ala Arg Phe Val Ile
        15                  20                  25 atc aag gtataacaaa ccataacttg gcttatgaac accatctaat gtattgcag gca  202
Ile Lys                                                        Ala
    30 acc gag ggt acc acc tac aaa gat ccc aag ttc agc cag cac tac atc    250
Thr Glu Gly Thr Thr Tyr Lys Asp Pro Lys Phe Ser Gln His Tyr Ile
        35                  40                  45 ggt gct acc aac gcc gga ttc atc cgc ggt ggc tac cac ttt gct cag    298
Gly Ala Thr Asn Ala Gly Phe Ile Arg Gly Gly Tyr His Phe Ala Gln
        50                  55                  60 cct gct tcc tct tct ggt gca gcg cag gca gac tat ttc ctc aag aac    346
Pro Ala Ser Ser Ser Gly Ala Ala Gln Ala Asp Tyr Phe Leu Lys Asn
        65                  70                  75 gga ggt ggt tgg tct agc gat gga att act ctc cca g gtgagcaaag        393
Gly Gly Gly Trp Ser Ser Asp Gly Ile Thr Leu Pro
80                  85                  90 tcacaaacgt tcgagggcag ttcactaata tcgtggcag gt atg ctt gat atg       446
                                             Gly Met Leu Asp Met
                                                             95 gag tac aac ccc aat ggc agt gct tgc tac ggt ctt tcc cag gct tcc    494
Glu Tyr Asn Pro Asn Gly Ser Ala Cys Tyr Gly Leu Ser Gln Ala Ser
            100                 105                 110 atg cgc aac tgg atc aac gac ttt gtc aac acc tac cac tcc cgc acg    542
Met Arg Asn Trp Ile Asn Asp Phe Val Asn Thr Tyr His Ser Arg Thr
        115                 120                 125 ggt gtc tac cct ctc ctt tac acc acc acc agc tgg tgg aaa acc tgc    590
Gly Val Tyr Pro Leu Leu Tyr Thr Thr Thr Ser Trp Trp Lys Thr Cys
        130                 135                 140
```

```
acg ggt aac act gcc atg ttt gcc gac aag tgc cct ctc gtc atc gct    638
Thr Gly Asn Thr Ala Met Phe Ala Asp Lys Cys Pro Leu Val Ile Ala
145                 150                 155                 160 cgc tac aac agc gta gtc gga gag ctc ccc gct ggt tgg tct ttc tgg    686
Arg Tyr Asn Ser Val Val Gly Glu Leu Pro Ala Gly Trp Ser Phe Trp
                165                 170                 175 aca att tgg cag tac aac gac cac tac aag cat ggt ggt gac tca gac    734
Thr Ile Trp Gln Tyr Asn Asp His Tyr Lys His Gly Gly Asp Ser Asp
            180                 185                 190 gct ttt aac gga gac tac tct cag ctt cag aga atc gcc aga ggc taa    782
Ala Phe Asn Gly Asp Tyr Ser Gln Leu Gln Arg Ile Ala Arg Gly
        195                 200                 205
```

<210> SEQ ID NO 29
<211> LENGTH: 227
<212> TYPE: PRT
<213> ORGANISM: Engyodontium album

<400> SEQUENCE: 29

```
Met Lys Ser Phe Gly Val Ile Ala Thr Gly Leu Ala Thr Leu Val Gly
-20                 -15                 -10                 -5

Val Ala Ser Ala Arg Val Gln Gly Phe Asp Ile Ser His Tyr Gln Pro
            -1  1                   5                  10

Ser Val Asp Phe Asn Ala Ala Tyr Ala Asp Gly Ala Arg Phe Val Ile
                15                  20                  25

Ile Lys Ala Thr Glu Gly Thr Thr Tyr Lys Asp Pro Lys Phe Ser Gln
            30                  35                  40

His Tyr Ile Gly Ala Thr Asn Ala Gly Phe Ile Arg Gly Gly Tyr His
45                  50                  55                  60

Phe Ala Gln Pro Ala Ser Ser Gly Ala Gln Ala Asp Tyr Phe
                65                  70                  75

Leu Lys Asn Gly Gly Gly Trp Ser Ser Asp Gly Ile Thr Leu Pro Gly
            80                  85                  90

Met Leu Asp Met Glu Tyr Asn Pro Asn Gly Ser Ala Cys Tyr Gly Leu
        95                 100                 105

Ser Gln Ala Ser Met Arg Asn Trp Ile Asn Asp Phe Val Asn Thr Tyr
    110                 115                 120

His Ser Arg Thr Gly Val Tyr Pro Leu Leu Tyr Thr Thr Thr Ser Trp
125                 130                 135                 140

Trp Lys Thr Cys Thr Gly Asn Thr Ala Met Phe Ala Asp Lys Cys Pro
                145                 150                 155

Leu Val Ile Ala Arg Tyr Asn Ser Val Val Gly Glu Leu Pro Ala Gly
            160                 165                 170

Trp Ser Phe Trp Thr Ile Trp Gln Tyr Asn Asp His Tyr Lys His Gly
        175                 180                 185

Gly Asp Ser Asp Ala Phe Asn Gly Asp Tyr Ser Gln Leu Gln Arg Ile
    190                 195                 200

Ala Arg Gly
205
```

<210> SEQ ID NO 30
<211> LENGTH: 207
<212> TYPE: PRT
<213> ORGANISM: Engyodontium album
<220> FEATURE:
<221> NAME/KEY: mat_peptide
<222> LOCATION: (1)..(207)

```
<400> SEQUENCE: 30

Arg Val Gln Gly Phe Asp Ile Ser His Tyr Gln Pro Ser Val Asp Phe
1               5                  10                 15

Asn Ala Ala Tyr Ala Asp Gly Ala Arg Phe Val Ile Ile Lys Ala Thr
            20                  25                 30

Glu Gly Thr Thr Tyr Lys Asp Pro Lys Phe Ser Gln His Tyr Ile Gly
        35                  40                 45

Ala Thr Asn Ala Gly Phe Ile Arg Gly Gly Tyr His Phe Ala Gln Pro
    50                  55                 60

Ala Ser Ser Ser Gly Ala Ala Gln Ala Asp Tyr Phe Leu Lys Asn Gly
65              70                  75                 80

Gly Gly Trp Ser Ser Asp Gly Ile Thr Leu Pro Gly Met Leu Asp Met
                85                  90                 95

Glu Tyr Asn Pro Asn Gly Ser Ala Cys Tyr Gly Leu Ser Gln Ala Ser
                100                 105                110

Met Arg Asn Trp Ile Asn Asp Phe Val Asn Thr Tyr His Ser Arg Thr
            115                 120                125

Gly Val Tyr Pro Leu Leu Tyr Thr Thr Thr Ser Trp Trp Lys Thr Cys
        130                 135                 140

Thr Gly Asn Thr Ala Met Phe Ala Asp Lys Cys Pro Leu Val Ile Ala
145                 150                 155                160

Arg Tyr Asn Ser Val Val Gly Glu Leu Pro Ala Gly Trp Ser Phe Trp
                165                 170                 175

Thr Ile Trp Gln Tyr Asn Asp His Tyr Lys His Gly Gly Asp Ser Asp
            180                 185                 190

Ala Phe Asn Gly Asp Tyr Ser Gln Leu Gln Arg Ile Ala Arg Gly
            195                 200                 205
```